United States Patent
Kawaue et al.

(10) Patent No.: US 11,022,880 B2
(45) Date of Patent: Jun. 1, 2021

(54) CHEMICALLY AMPLIFIED POSITIVE-TYPE PHOTOSENSITIVE RESIN COMPOSITION, PHOTOSENSITIVE DRY FILM, METHOD OF MANUFACTURING PHOTOSENSITIVE DRY FILM, METHOD OF MANUFACTURING PATTERNED RESIST FILM, METHOD OF MANUFACTURING SUBSTRATE WITH TEMPLATE, METHOD OF MANUFACTURING PLATED ARTICLE, AND MERCAPTO COMPOUND

(71) Applicant: TOKYO OHKA KOGYO CO., LTD., Kawasaki (JP)

(72) Inventors: Akiya Kawaue, Kawasaki (JP); Yuta Yamamoto, Kawasaki (JP); Kazuaki Ebisawa, Kawasaki (JP); Yasushi Kuroiwa, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 138 days.

(21) Appl. No.: 16/160,297

(22) Filed: Oct. 15, 2018

(65) Prior Publication Data

US 2019/0121233 A1 Apr. 25, 2019

(30) Foreign Application Priority Data

Oct. 25, 2017 (JP) .............................. JP2017-206609
Apr. 4, 2018 (JP) .............................. JP2018-072719

(51) Int. Cl.
| | | |
|---|---|---|
| *G03F 7/004* | (2006.01) |
| *G03F 7/039* | (2006.01) |
| *G03F 7/38* | (2006.01) |
| *G03F 7/16* | (2006.01) |
| *G03F 7/32* | (2006.01) |
| *C07D 493/08* | (2006.01) |
| *C07C 323/61* | (2006.01) |
| *G03F 7/20* | (2006.01) |
| *G03F 7/40* | (2006.01) |
| *C07D 307/93* | (2006.01) |
| *C07D 249/12* | (2006.01) |
| *C07C 323/62* | (2006.01) |
| *C07D 249/10* | (2006.01) |
| *C07D 249/06* | (2006.01) |
| *C07C 321/22* | (2006.01) |
| *C07D 495/08* | (2006.01) |
| *C07C 321/24* | (2006.01) |

(52) U.S. Cl.
CPC .......... *G03F 7/0045* (2013.01); *C07C 323/61* (2013.01); *C07C 323/62* (2013.01); *C07D 249/06* (2013.01); *C07D 249/10* (2013.01); *C07D 249/12* (2013.01); *C07D 307/93* (2013.01); *C07D 493/08* (2013.01); *G03F 7/0392* (2013.01); *G03F 7/0397* (2013.01); *G03F 7/16* (2013.01); *G03F 7/168* (2013.01); *G03F 7/2008* (2013.01); *G03F 7/322* (2013.01); *G03F 7/38* (2013.01); *G03F 7/40* (2013.01); *C07C 321/22* (2013.01); *C07C 321/24* (2013.01); *C07C 2601/14* (2017.05); *C07C 2602/42* (2017.05); *C07D 495/08* (2013.01)

(58) Field of Classification Search
CPC .... G03F 7/0045; G03F 7/0392; G03F 7/0397; C07D 249/06; C07D 249/10; C07D 249/12; C07D 493/08; C07D 495/08; C07C 321/22; C07C 321/24; C07C 323/61; C07C 323/62
See application file for complete search history.

(56) References Cited

U.S. PATENT DOCUMENTS

| | | | | |
|---|---|---|---|---|
| 6,664,281 B1* | 12/2003 | Tajima | ................. | C07D 413/04 514/374 |
| 2003/0039916 A1* | 2/2003 | Adegawa | .............. | G03F 7/0045 430/270.1 |
| 2014/0154624 A1* | 6/2014 | Liu | ....................... | G03F 7/0397 430/270.1 |

(Continued)

FOREIGN PATENT DOCUMENTS

| | | |
|---|---|---|
| JP | H09-176112 | 7/1997 |
| JP | H11-052562 | 2/1999 |

OTHER PUBLICATIONS

AK Scientific, Inc Compound 8878AC 2-(5-Thioxo-4,5-dihydro-1H-1,2,4-triazol-3-yl)-benzoic acid https://aksci.com/item_detail.php?cat=8878AC or http://www.chemspider.com/Chemical-Structure.15377610.html?rid=c0dbad3e-fcf2-4cd3-bf75-d5300e8508a3 [retrieved on Feb. 11, 2021].*

*Primary Examiner* — John S Chu
(74) *Attorney, Agent, or Firm* — Knobbe Martens Olson & Bear LLP

(57) ABSTRACT

A chemically amplified positive-type photosensitive resin composition capable of suppressing the occurrence of "footing" in which the width of the bottom (the side proximal to the surface of a support) becomes narrower than that of the top (the side proximal to the surface of a resist layer) in the nonresist portion; and the generation of development residue when a resist pattern serving as a template for a plated article is formed on a metal surface of a substrate using the photosensitive resin composition. A mercapto compound having a specific structure is included in the photosensitive resin composition, and includes an acid generator which generates acid upon exposure to an irradiated active ray or radiation, and a resin whose solubility in alkali increases under the action of acid.

14 Claims, 1 Drawing Sheet

(56) References Cited

U.S. PATENT DOCUMENTS

| | | | |
|---|---|---|---|
| 2015/0268553 A1* | 9/2015 | Katayama | G03F 7/0045 430/285.1 |
| 2016/0024025 A1* | 1/2016 | Kumar | C07D 249/08 544/92 |

* cited by examiner

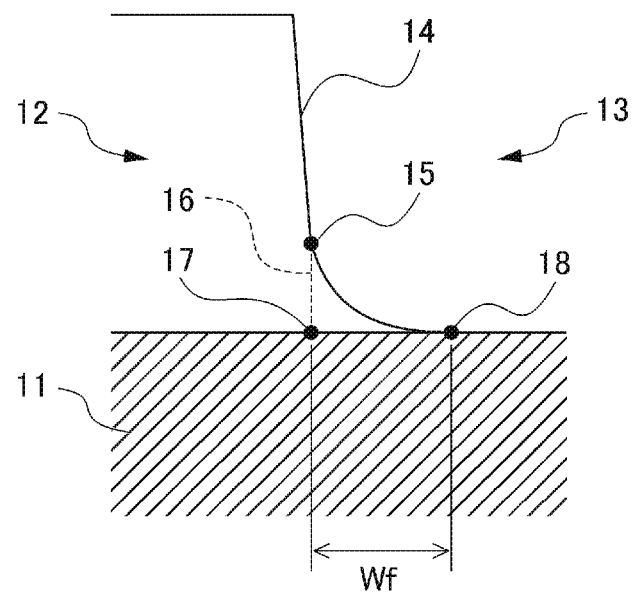

CHEMICALLY AMPLIFIED POSITIVE-TYPE PHOTOSENSITIVE RESIN COMPOSITION, PHOTOSENSITIVE DRY FILM, METHOD OF MANUFACTURING PHOTOSENSITIVE DRY FILM, METHOD OF MANUFACTURING PATTERNED RESIST FILM, METHOD OF MANUFACTURING SUBSTRATE WITH TEMPLATE, METHOD OF MANUFACTURING PLATED ARTICLE, AND MERCAPTO COMPOUND

RELATED APPLICATIONS

This application claims priority to Japanese Patent Application No. 2017-206609, filed Oct. 25, 2017, and Japanese Patent Application No. 2018-072719, filed Apr. 4, 2018, the entire contents of which are incorporated herein by reference.

BACKGROUND OF THE INVENTION

Field of the Invention

The present invention relates to a chemically amplified positive-type photosensitive resin composition, a photosensitive dry film having a photosensitive resin layer formed by the chemically amplified positive-type photosensitive resin composition, a method of manufacturing the photosensitive dry film, a method of manufacturing a patterned resist film using the above-mentioned chemically amplified positive-type photosensitive resin composition, a method of manufacturing a substrate with a template using the above-mentioned chemically amplified positive-type photosensitive resin composition, and a method of manufacturing a plated article using the substrate with a template.

Related Art

Photofabrication is now the mainstream of a microfabrication technique. Photofabrication is a generic term describing the technology used for manufacturing a wide variety of precision components such as semiconductor packages. The manufacturing is carried out by applying a photoresist composition to the surface of a processing target to form a photoresist layer, patterning this photoresist layer using photolithographic techniques, and then conducting chemical etching, electrolytic etching, or electroforming based mainly on electroplating, using the patterned photoresist layer (photoresist pattern) as a mask.

In recent years, high density packaging technologies have progressed in semiconductor packages along with downsizing electronics devices, and the increase in package density has been developed on the basis of mounting multi-pin thin film in packages, miniaturizing of package size, two-dimensional packaging technologies in flip-tip systems or three-dimensional packaging technologies. In these types of high density packaging techniques, connection terminals, for example, protruding electrodes (mounting terminals) known as bumps that protrude above the package or metal posts that extend from peripheral terminals on the wafer and connect rewiring with the mounting terminals, are disposed on the surface of the substrate with high precision.

In the photofabrication as described above, a photoresist composition is used, and chemically amplified photoresist compositions containing an acid generator have been known as such a photoresist composition (see Patent Documents 1, 2 and the like). According to the chemically amplified photoresist composition, an acid is generated from the acid generator upon irradiation with radiation (exposure) and diffusion of the acid is promoted through heat treatment, to cause an acid catalytic reaction with a base resin and the like in the composition resulting in a change to the alkali-solubility of the same.

Such chemically amplified positive-type photoresist compositions are used, for example, in formation of plated articles such as bumps and metal posts by a plating step. Specifically, a photoresist layer having a desired film thickness is formed on a support such as a metal substrate using a chemically amplified photoresist composition, and the photoresist layer is exposed through a predetermined mask pattern and is developed. Thereby, a photoresist pattern used as a template in which portions for forming bumps or metal posts have been selectively removed (stripped) is formed. Then, bumps or metal posts can be formed by embedding a conductor such as copper into the removed portions (nonresist portions) using plating, and then removing the surrounding photoresist pattern.

Patent Document 1: Japanese Unexamined Patent Application, Publication No. H09-176112

Patent Document 2: Japanese Unexamined Patent Application, Publication No. H11-52562

SUMMARY OF THE INVENTION

In formation of connection terminals such as bumps or metal posts by plating step mentioned above, with respect to the nonresist portion of the resist pattern as a template, width of the bottom (surface side of the support) is desired to be larger than width of the top (front surface side of the resist layer). Thus, the contact area between the bottom surface of the connection terminals such as bumps or metal posts and the support is increased, and thereby adhesiveness between the connection terminals and the support is improved.

However, in a case where a resist pattern serving as a template for forming a bump, a metal post, and the like, is formed on a metal substrate with a conventionally known chemically amplified positive-type photoresist composition as disclosed in Patent Documents 1, 2 and the like, a phenomenon called "footing" tends to occur in which the width of the bottom becomes narrower than that of the top in a nonresist portion due to protrusion of a resist portion toward the nonresist portion at the contacting surface between the substrate surface and the resist pattern. For this reason, in a case where a conventionally known chemically amplified positive-type photoresist composition as disclosed in Patent Documents 1, 2 and the like is used, it is difficult to form a resist pattern having a nonresist portion in which the width of the bottom is wider than that of the top on a metal substrate.

When a resist pattern serving as a template for plating is formed on a metal substrate using a chemically amplified positive-type photoresist composition, it is desired that development residue is not easily generated.

The present invention has been made in view of the above problem. An object of the present invention is to provide a chemically amplified positive-type photosensitive resin composition capable of suppressing the occurrence of "footing" in which the width of the bottom (surface side of the support) becomes narrower than that of the top (front surface side of the resist layer) in the nonresist portion and the generation of development residue when a resist pattern serving as a template for a plated article is formed on a metal surface of a substrate having a metal surface by using the chemically amplified positive-type photosensitive resin composition; a photosensitive dry film having a photosensitive resin layer including the chemically amplified positive-type photosensitive resin; a method of producing the photosensitive dry film; a method of producing a patterned resist film using the above-mentioned chemically amplified positive-type photosensitive resin composition; a method of producing a substrate with a template using the above-mentioned photosensitive resin; and a method of producing a plated article using the substrate with a template.

After conducting extensive studies in order to achieve the above objects, the present inventors have found that the above problem can be solved by including a mercapto compound with a specific structure in a chemically amplified positive-type photosensitive resin composition, and have completed the present invention. Specifically, the present invention provides the following.

A first aspect of the present invention is a chemically amplified positive-type photosensitive resin composition including an acid generator (A) which generates acid upon exposure to an irradiated active ray or radiation, a resin (B) whose solubility in alkali increases under the action of acid, and a mercapto compound (C) represented by the following formula (C1).

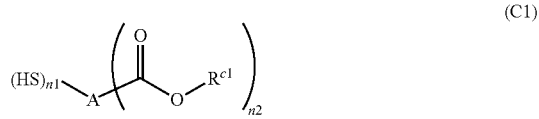

(C1)

(In the formula (C1), A is an (n1+n2)-valent linking group including a cyclic group which optionally has one or more substituents and optionally includes one or more heteroatoms, A and a mercapto group are bonded to each other by a C—S bond, A and a group represented by —CO—O—$R^{c1}$ are bonded to each other by a C—C bond, $R^{c1}$s each independently represent a hydrogen atom, a hydrocarbon group or an acid dissociable group, n1 is an integer of 1 or more and 4 or less, n2 is 1 or 2, and at least one of $R^{c1}$ is a hydrogen atom or an acid dissociable group.)

A second aspect of the present invention is a photosensitive dry film comprising a substrate film, and a photosensitive resin layer formed on a surface of the substrate film, wherein the photosensitive resin layer includes the chemically amplified positive-type photosensitive resin composition according to the first aspect.

A third aspect of the present invention is a method of manufacturing a photosensitive dry film. The method includes applying the chemically amplified positive-type photosensitive resin composition according to the first aspect on a substrate film to form a photosensitive resin layer.

A fourth aspect of the present invention is a method of manufacturing a patterned resist film. The method includes:
laminating a photosensitive resin layer on a substrate having a metal surface, the layer comprising the chemically amplified positive-type photosensitive resin composition of the first aspect,
exposing the photosensitive resin layer through irradiation with an active ray or radiation in a position-selective manner, and
developing the exposed photosensitive resin layer.

A fifth aspect of the present invention is a method of manufacturing a substrate with a template. The method includes:
laminating a photosensitive resin layer on a substrate having a metal surface, the layer comprising the chemically amplified positive-type photosensitive resin composition of the first aspect,
exposing the photosensitive resin layer through irradiation with an active ray or radiation in a position-selective manner, and
developing the exposed photosensitive resin layer to prepare a template for plated article.

A sixth aspect of the present invention is a method of manufacturing a plated article, and the method comprising plating the substrate with the template manufactured by the method of the fifth aspect to form the plated article in the template.

A seventh aspect of the present invention is a mercapto compound represented by the following formula (C1-1).

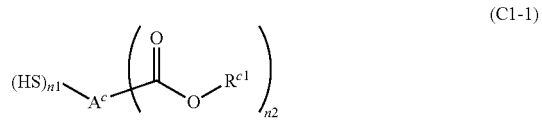

(C1-1)

(In the formula (C1-1), $A^c$ is a (n1+n2)-valent aliphatic cyclic group which optionally has one or more substituents and optionally includes one or more heteroatoms, $R^{c1}$s each independently represent a hydrogen atom, a hydrocarbon group or an acid dissociable group, n1 is an integer of 1 or more and 4 or less, n2 is 2, and at least one of $R^{c1}$s is a hydrogen atom or an acid dissociable group.)

An eighth aspect of the present invention is a mercapto compound represented by the following formula (C1-5).

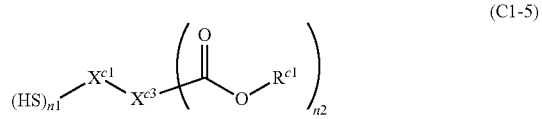

(C1-5)

(In the formula (C1-5), $R^{c1}$ each independently represent a hydrogen atom, a hydrocarbon group or an acid dissociable group, n1 is an integer of 1 or more and 4 or less, n2 is 1 or 2, at least one of $R^{c1}$ is a hydrogen atom or an acid dissociable group, $X^{c1}$ is an (n1+1)-valent nitrogen-containing heterocyclic group, and $X^{c3}$ is an (n2+1)-valent aromatic hydrocarbon group substituted with one or more electron withdrawing groups.)

The present invention can provide a chemically amplified positive-type photosensitive resin composition capable of suppressing the occurrence of "footing" in which the width of the bottom (surface side of the support) becomes narrower than that of the top (front surface side of the resist layer) in the nonresist portion and the generation of development residue when a resist pattern serving as a template for a plated article is formed on a metal surface of a substrate having a metal surface by using the chemically amplified positive-type photosensitive resin composition; a photosensitive dry film having a photosensitive resin layer including the chemically amplified positive-type photosensitive resin composition, a method of producing the photosensitive dry film, a method of producing a patterned resist film using the above-mentioned chemically amplified positive-type photosensitive resin composition, a method of producing a substrate with a template using the above-mentioned photosensitive resin composition, and a method of producing a plated article using the substrate with a template.

BRIEF DESCRIPTION OF THE DRAWINGS

FIG. 1 is a view schematically showing a cross section of a resist pattern when a footing amount in a nonresist portion in the resist pattern is observed in Examples and Comparative Examples.

DETAILED DESCRIPTION OF THE INVENTION

<<Chemically Amplified Positive-Type Photosensitive Resin Composition>>

The chemically amplified positive-type photosensitive resin composition (hereinafter also referred to as the "photosensitive resin composition") includes an acid generator (A) capable of producing an acid when irradiated with an active ray or radiation (hereinafter also referred to as the acid generator (A)), a resin (B) the solubility of which in alkali increases under the action of acid (hereinafter also referred to as the resin (B)), and a mercapto compound (C) having a predetermined structure. The photosensitive resin composition may include components such as an alkali-soluble resin (D), an acid diffusion suppressing agent (E), and an organic solvent (S), if desired.

The film thickness of the resist pattern formed using the photosensitive resin composition is not particularly limited. The photosensitive resin composition is preferably used for the formation of a thick resist pattern. Specifically, the film thickness of a resist pattern formed using the photosensitive resin composition is preferably 0.5 µm or more, more preferably 0.5 µm or more and 300 µm or less, particularly preferably 1 µm or more and 150 µm or less, and most preferably 3 µm or more and 100 µm or less.

Hereinafter, described are essential or optional components in the photosensitive resin composition, and a method for manufacturing the photosensitive resin composition.

<Acid Generator (A)>

The acid generator (A) is a compound capable of producing an acid when irradiated with an active ray or radiation, and is not particularly limited as long as it is a compound which directly or indirectly produces an acid under the action of light. The acid generator (A) is preferably any one of the acid generators of the first to fifth aspects that will be described below. Hereinafter, suitable aspects of the acid generator (A) that are suitably used in photosensitive resin compositions will be described as the first to fifth aspects.

The first aspect of the acid generator (A) may be a compound represented by the following formula (a1).

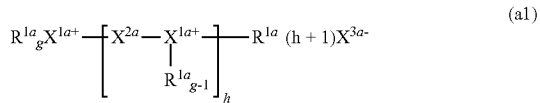
(a1)

In the formula (a1), $X^{1a}$ represents a sulfur atom or iodine atom respectively having a valence of g; g represents 1 or 2. h represents the number of repeating units in the structure within parentheses. $R^{1a}$ represents an organic group that is bonded to $X^{1a}$, and represents an aryl group having 6 or more and 30 or less carbon atoms, a heterocyclic group having 4 or more and 30 or less carbon atoms, an alkyl group having 1 or more and 30 or less carbon atoms, an alkenyl group having 2 or more and 30 or less carbon atoms, or an alkynyl group having 2 or more and 30 or less carbon atoms, and Rid may be substituted with at least one selected from the group consisting of an alkyl group, a hydroxyl group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic group, an aryloxy group, an alkylsulfinyl group, an arylsulfinyl group, an alkylsulfonyl group, an arylsulfonyl group, an alkyleneoxy group, an amino group, a cyano group, a nitro group, and halogen atoms. The number of $R^{1a}$s is g+h(g−1)+1, and the $R^{1a}$s may be respectively identical to or different from each other.

Furthermore, two or more $R^{1a}$s may be bonded to each other directly or via —O—, —S—, —SO—, —SO$_2$—, —NH—, —NR$^{2a}$—, —CO—, —COO—, —CONH—, an alkylene group having 1 or more and 3 or less carbon atoms, or a phenylene group, and may form a ring structure including $X^{1a}$. $R^{2a}$ represents an alkyl group having 1 or more and 5 or less carbon atoms, or an aryl group having 6 or more and 10 or less carbon atoms.

$X^{2a}$ represents a structure represented by the following formula (a2).

(a2)

In the above formula (a2), $X^{4a}$ represents an alkylene group having 1 or more and 8 or less carbon atoms, an arylene group having 6 or more and 20 or less carbon atoms, or a divalent group of a heterocyclic compound having 8 or more and 20 or less carbon atoms, and $X^{4a}$ may be substituted with at least one selected from the group consisting of an alkyl group having 1 or more and 8 or less carbon atoms, an alkoxy group having 1 or more and 8 or less carbon atoms, an aryl group having 6 or more and 10 or less carbon atoms, a hydroxyl group, a cyano group, a nitro group, and halogen atoms. $X^{5a}$ represents —O—, —S—, —SO—, —SO$_2$—, —NH—, —NR$^{2a}$—, —CO—, —COO—, —CONH—, an alkylene group having 1 or more and 3 or less carbon atoms, or a phenylene group. h represents the number of repeating units of the structure in parentheses. $X^{4a}$s in the number of h+1 and $X^{5a}$s in the number of h may be identical to or different from each other. $R^{2a}$ has the same definition as described above.

$X^{3a-}$ represents a counterion of an onium, and examples thereof include a fluorinated alkylfluorophosphoric acid anion represented by the following formula (a17) or a borate anion represented by the following formula (a18).

(a17)

In the formula (a17), $R^{3a}$ represents an alkyl group having 80% or more of the hydrogen atoms substituted with fluorine atoms. j represents the number of $R^{3a}$s and is an integer of 1 or more and 5 or less. $R^{3a}$s in the number of j may be respectively identical to or different from each other.

(a18)

In the formula (a18) $R^{4a}$ to $R^{7a}$ each independently represents a fluorine atom or a phenyl group, and a part or all of the hydrogen atoms of the phenyl group may be substituted with at least one selected from the group consisting of a fluorine atom and a trifluoromethyl group.

Examples of the onium ion in the compound represented by the above formula (a1) include triphenylsulfonium, tri-p-tolylsulfonium, 4-(phenylthio)phenyldiphenylsulfonium, bis[4-(diphenylsulfonio)phenyl]sulfide, bis[4-{bis[4-(2-hydroxyethoxy)phenyl]sulfonio}phenyl] sulfide, bis{4-[bis(4-fluorophenyl)sulfonio]phenyl} sulfide, 4-(4-benzoyl-2-chlorophenylthio)phenylbis(4-fluorophenyl)sulfonium, 7-isopropyl-9-oxo-10-thia-9,10-dihydroanthracen-2-yldi-p-tolylsulfonium, 7-isopropyl-9-oxo-10-thia-9,10-dihydroanthracen-2-yldiphenylsulfonium, 2-[(diphenyl)sulfonio]thioxanthone, 4-[4-(4-tert-butylbenzoyl)phenylthio]phenyldi-p-tolylsulfonium, 4-(4-benzoylphenylthio)phenyldiphenylsulfonium, diphenylphenacylsulfonium, 4-hydroxyphenylmethylbenzylsulfo-nium, 2-naphthylmethyl(1-ethoxycarbonyl)ethylsulfonium, 4-hydroxyphenylmethylphenacylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio)phenyl]diphenylsulfonium, octadecylmethylphenacylsulfonium, diphenyliodonium, di-p-tolyliodonium, bis(4-dodecylphenyl)iodonium, bis(4-methoxyphenyl)iodonium, (4-octyloxyphenyl)phenyliodonium, bis(4-decyloxy)phenyliodonium, 4-(2-hydroxytetradecyloxy)phenylphenyliodonium, 4-isopropylphenyl(p-tolyl)iodonium, 4-isobutylphenyl(p-tolyl)iodonium, or the like.

Among the onium ions in the compound represented by the above formula (a1), a preferred onium ion may be a sulfonium ion represented by the following formula (a19).

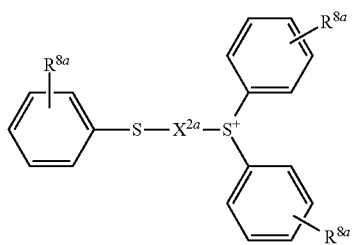

(a19)

In the above formula (a19), $R^{8a}$s each independently represents a hydrogen atom or a group selected from the group consisting of alkyl, hydroxyl, alkoxy, alkylcarbonyl, alkylcarbonyloxy, alkyloxycarbonyl, a halogen atom, an aryl, which may be substituted, and arylcarbonyl. $X^{2a}$ has the same definition as $X^{2a}$ in the above formula (a1).

Specific examples of the sulfonium ion represented by the above formula (a19) include 4-(phenylthio)phenyldiphenylsulfonium, 4-(4-benzoyl-2-chlorophenylthio)phenylbis(4-fluorophenyl)sulfonium, 4-(4-benzoylphenylthio)phenyldiphenylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio)phenyl]diphenylsulfonium, and diphenyl[4-(p-terphenylthio)phenyl]diphenylsulfonium.

In regard to the fluorinated alkylfluorophosphoric acid anion represented by the above formula (a17), $R^{3a}$ represents an alkyl group substituted with a fluorine atom, and a preferred number of carbon atoms is 1 or more and 8 or less, while a more preferred number of carbon atoms is 1 or more and 4 or less. Specific examples of the alkyl group include linear alkyl groups such as methyl, ethyl, propyl, butyl, pentyl and octyl; branched alkyl groups such as isopropyl, isobutyl, sec-butyl and tert-butyl; and cycloalkyl groups such as cyclopropyl, cyclobutyl, cyclopentyl, and cyclohexyl. The proportion of hydrogen atoms substituted with fluorine atoms in the alkyl groups is usually 80% or more, preferably 90% or more, and even more preferably 100%. If the substitution ratio of fluorine atoms is less than 80%, the acid strength of the onium fluorinated alkylfluorophosphate represented by the above formula (a1) decreases.

A particularly preferred example of $R^{3a}$ is a linear or branched perfluoroalkyl group having 1 or more and 4 or less carbon atoms and a substitution ratio of fluorine atoms of 100%. Specific examples thereof include $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$, and $(CF_3)_3C$. j which is the number of $R^{3a}$s represents an integer of 1 or more and 5 or less, and is preferably 2 or more and 4 or less, and particularly preferably 2 or 3.

Preferred specific examples of the fluorinated alkylfluorophosphoric acid anion include $[(CF_3CF_2)_2PF_4]^-$, $[(CF_3CF_2)_3PF_3]^-$, $[((CF_3)_2CF)_2PF_4]^-$, $[((CF_3)_2CF)_3PF_3]^-$, $[(CF_3CF_2CF_2)_2PF_4]^-$, $[(CF_3CF_2CF_2)_3PF_3]^-$, $[((CF_3)_2CFCF_2)_2PF_4]^-$, $[((CF_3)_2CFCF_2)_3PF_3]^-$, $[(CF_3CF_2CF_2CF_2)_2PF_4]^-$, or $[(CF_3CF_2CF_2)_3PF_3]^-$. Among these, $[(CF_3CF_2)_3PF_3]$, $[(CF_3CF_2CF_2)_3PF_3]$, $[((CF_3)_2CF)_3PF_3]^-$, $[((CF_3)_2CF)_2PF_4]^-$, $[((CF_3)_2CFCF_2)_3PF_3]^-$, or $[((CF_3)_2CFCF_2)_2PF_4]^-$ are particularly preferred.

Preferred specific examples of the borate anion represented by the above formula (a18) include tetrakis(pentafluorophenyl)borate ($[B(C_6F_5)_4]^-$), tetrakis[(trifluoromethyl)phenyl]borate ($[B(C_6H_4CF_3)_4]^-$), difluorobis(pentafluorophenyl)borate ($[(C_6F_5)_2BF_2]^-$), trifluoro(pentafluorophenyl)borate ($[(C_6F_5)BF_3]^-$), and tetrakis(difluorophenyl)borate ($[B(C_6H_3F_2)_4]^-$). Among these, tetrakis(pentafluorophenyl)borate ($[B(C_6F_5)_4]^-$) is particularly preferred.

The second aspect of the acid generator (A) include halogen-containing triazine compounds such as 2,4-bis(trichloromethyl)-6-piperonyl-1,3,5-triazine, 2,4-bis(trichloromethyl)-6-[2-(2-furyl)ethenyl]-s-triazine, 2,4-bis(trichloromethyl)-6-[2-(5-methyl-2-furyl)ethenyl]-s-triazine, 2,4-bis(trichloromethyl)-6-[2-(5-ethyl-2-furyl)ethenyl]-s-triazine, 2,4-bis(trichloromethyl)-6-[2-(5-propyl-2-furyl)ethenyl]-s-triazine, 2,4-bis(trichloromethyl)-6-[2-(3,5-dimethoxyphenyl)ethenyl]-s-triazine, 2,4-bis(trichloromethyl)-6-[2-(3,5-diethoxyphenyl)ethenyl]-s-triazine, 2,4-bis(trichloromethyl)-6-[2-(3,5-dipropoxyphenyl)ethenyl]-s-triazine, 2,4-bis(trichloromethyl)-6-[2-(3-methoxy-5-ethoxyphenyl)ethenyl]-s-triazine, 2,4-bis(trichloromethyl)-6-[2-(3-methoxy-5-propoxyphenyl)ethenyl]-s-triazine, 2,4-bis(trichloromethyl)-6-[2-(3,4-methylenedioxyphenyl)ethenyl]-s-triazine, 2,4-bis(trichloromethyl)-6-(3,4-methylenedioxyphenyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(2-bromo-4-methoxy)styrylphenyl-s-triazine, 2,4-bis-trichloromethyl-6-(3-bromo-4-methoxy)styrylphenyl-s-triazine, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis (trichloromethyl)-1,3,5-triazine, tris(1,3-dibromopropyl)-1,3,5-triazine and tris(2,3-dibromopropyl)-1,3,5-triazine, and halogen-containing triazine compounds represented by the following formula (a3) such as tris(2,3-dibromopropyl)isocyanurate.

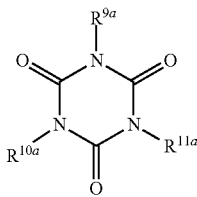

In the above formula (a3), $R^{9a}$, $R^{10a}$ and $R^{11a}$ each independently represent a halogenated alkyl group.

Further, the third aspect of the acid generator (A) include α-(p-toluenesulfonyloxyimino)-phenylacetonitrile, α-(benzenesulfonyloxyimino)-2,4-dichlorophenylacetonitrile, α-(benzenesulfonyloxyimino)-2,6-dichlorophenylacetonitrile, α-(2-chlorobenzenesulfonyloxyimino)-4-methoxyphenylacetonitrile and α-(ethylsulfonyloxyimino)-1-cyclopentenylacetonitrile, and compounds represented by the following formula (a4) having an oximesulfonate group.

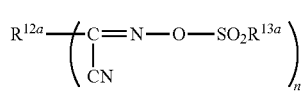

In the above formula (a4), $R^{12a}$ represents a monovalent, bivalent or trivalent organic group, $R^{13a}$ represents a substituted or unsubstituted saturated hydrocarbon group, an unsaturated hydrocarbon group, or an aromatic group, and n represents the number of repeating units of the structure in the parentheses.

In the formula (a4), the aromatic group indicates a group of compounds having physical and chemical properties characteristic of aromatic compounds, and examples thereof include aryl groups such as a phenyl group and a naphthyl group, and heteroaryl groups such as a furyl group and a thienyl group. These may have one or more appropriate substituents such as halogen atoms, alkyl groups, alkoxy groups and nitro groups on the rings. It is particularly preferable that $R^{13a}$ is an alkyl group having 1 or more and 6 or less carbon atoms such as a methyl group, an ethyl group, a propyl group, and a butyl group. In particular, compounds in which $R^{12a}$ represents an aromatic compound group, and $R^{13a}$ represents an alkyl group having 1 or more and 4 or less carbon atoms are preferred.

Examples of the acid generator represented by the above formula (a4) include compounds in which $R^{12a}$ is any one of a phenyl group, a methylphenyl group and a methoxyphenyl group, and $R^{13a}$ is a methyl group, provided that n is 1, and specific examples thereof include α-(methylsulfonyloxyimino)-1-phenylacetonitrile, α-(methylsulfonyloxyimino)-1-(p-methylphenyl)acetonitrile, α-(methylsulfonyloxyimino)-1-(p-methoxyphenyl)acetonitrile, [2-(propylsulfonyloxyimino)-2,3-dihydroxythiophene-3-ylidene] (o-tolyl)acetonitrile and the like. Provided that n is 2, the acid generator represented by the above formula (a4) is specifically an acid generator represented by the following formulae.

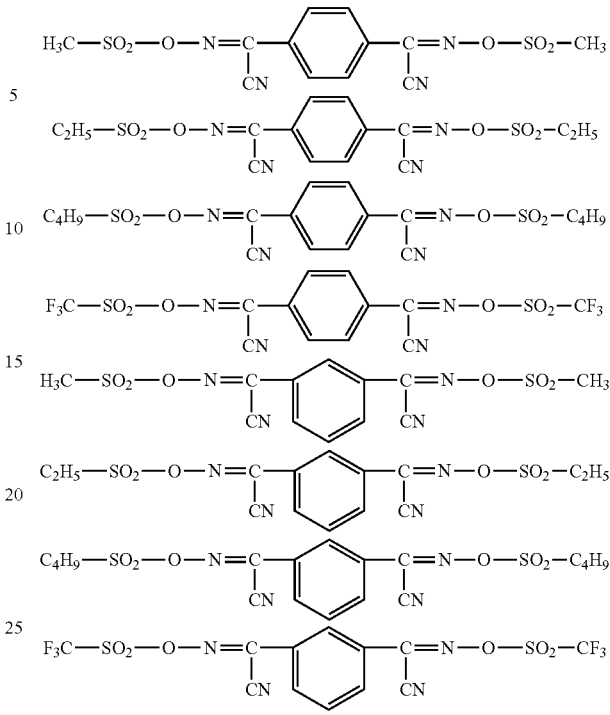

In addition, the fourth aspect of the acid generator (A) include onium salts that have a naphthalene ring at their cation moiety. The expression "have a naphthalene ring" indicates having a structure derived from naphthalene and also indicates at least two ring structures and their aromatic properties are maintained. The naphthalene ring may have a substituent such as a linear or branched alkyl group having 1 or more and 6 or less carbon atoms, a hydroxyl group, a linear or branched alkoxy group having 1 or more and 6 or less carbon atoms or the like. The structure derived from the naphthalene ring, which may be of a monovalent group (one free valance) or of a bivalent group (two free valences), is desirably of a monovalent group (in this regard, the number of free valance is counted except for the portions connecting with the substituents described above). The number of naphthalene rings is preferably 1 or more and 3 or less.

Preferably, the cation moiety of the onium salt having a naphthalene ring at the cation moiety is of the structure represented by the following formula (a5).

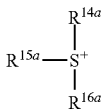

In the above formula (a5), at least one of $R^{14a}$, $R^{15a}$ and $R^{16a}$ represents a group represented by the following formula (a6), and the remaining represents a linear or branched alkyl group having 1 or more and 6 or less carbon atoms, a phenyl group which may have a substituent, a hydroxyl group, or a linear or branched alkoxy group having 1 or more and 6 or less carbon atoms. Alternatively, one of $R^{14a}$, $R^{15a}$ and $R^{16a}$ is a group represented by the following formula (a6), and the remaining two are each independently a linear or branched alkylene group having 1 or more and 6 or less carbon atoms, and these terminals may bond to form a ring structure.

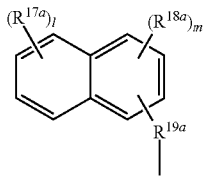
(a6)

In the formula (a6), $R^{17a}$ and $R^{18a}$ each independently represent a hydroxyl group, a linear or branched alkoxy group having 1 or more and 6 or less carbon atoms, or a linear or branched alkyl group having 1 or more and 6 or less carbon atoms, and $R^{19a}$ represents a single bond or a linear or branched alkylene group having 1 or more and 6 or less carbon atoms that may have a substituent. l and m each independently represent an integer of 0 or more and 2 or less, and l+m is 3 or less. Herein, when there exists a plurality of $R^{17a}$, they may be identical to or different from each other. Furthermore, when there exists a plurality of $R^{18a}$, they may be identical to or different from each other.

Preferably, among $R^{14a}$, $R^{15a}$ and $R^{16a}$ as above, the number of groups represented by the above formula (a6) is one in view of the stability of the compound, and the remaining are linear or branched alkylene groups having 1 or more and 6 or less carbon atoms of which the terminals may bond to form a ring. In this case, the two alkylene groups described above form a 3 to 9 membered ring including sulfur atom(s). Preferably, the number of atoms to form the ring (including sulfur atom(s)) is 5 or more and 6 or less.

Examples of the substituent, which the alkylene group may have, include an oxygen atom (in this case, a carbonyl group is formed together with a carbon atom that constitutes the alkylene group), a hydroxyl group or the like.

Furthermore, examples of the substituent, which the phenyl group may have, include a hydroxyl group, a linear or branched alkoxy group having 1 or more and 6 or less carbon atoms, a linear or branched alkyl group having 1 or more and 6 or less carbon atoms, or the like.

Examples of cations for the suitable cation moiety include cations represented by the following formulae (a7) and (a8), and the structure represented by the following formula (a8) is particularly preferable.

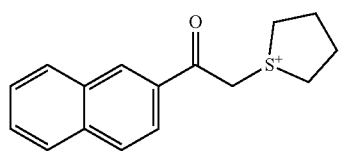
(a7)

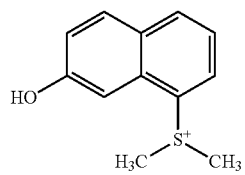
(a8)

The cation moieties, which may be of an iodonium salt or a sulfonium salt, are desirably of a sulfonium salt in view of acid-producing efficiency.

It is, therefore, desirable that the suitable anions for the anion moiety of the onium salt having a naphthalene ring at the cation moiety is an anion capable of forming a sulfonium salt.

The anion moiety of the acid generator is exemplified by fluoroalkylsulfonic acid ions or aryl sulfonic acid ions, of which hydrogen atom(s) being partially or entirely fluorinated.

The alkyl group of the fluoroalkylsulfonic acid ions may be linear, branched or cyclic and have 1 or more and 20 or less carbon atoms. Preferably, the carbon number is 1 or more and 10 or less in view of bulkiness and diffusion distance of the produced acid. In particular, branched or cyclic alkyl groups are preferable due to shorter diffusion length. Also, methyl, ethyl, propyl, butyl, octyl groups and the like are preferable due to being inexpensively synthesizable.

The aryl group of the aryl sulfonic acid ions may be an aryl group having 6 or more and 20 or less carbon atoms, and is exemplified by a phenol group or a naphthyl group that may be unsubstituted or substituted with an alkyl group or a halogen atom. In particular, aryl groups having 6 or more and 10 or less carbon atoms are preferable due to being inexpensively synthesizable. Specific examples of preferable aryl group include phenyl, toluenesulfonyl, ethylphenyl, naphthyl, methylnaphthyl groups and the like.

When hydrogen atoms in the above fluoroalkylsulfonic acid ion or the aryl sulfonic acid ion are partially or entirely substituted with a fluorine atom, the fluorination rate is preferably 10% or more and 100% or less, and more preferably 50% or more and 100% or less; it is particularly preferable that all hydrogen atoms are each substituted with a fluorine atom in view of higher acid strength. Specific examples thereof include trifluoromethane sulfonate, perfluorobutane sulfonate, perfluorooctane sulfonate, perfluorobenzene sulfonate, and the like.

Among these, the preferable anion moiety is exemplified by those represented by the following formula (a9).

$$R^{20a}SO_3^-  \quad (a9)$$

In the above formula (a9), $R^{20a}$ represents groups represented by the following formulae (a10), (a11), and (a12).

—$C_xF_{2x+1}$ (a10)

(a11)

(a12)
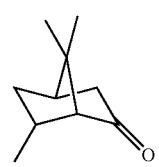

In the above formula (a10), x represents an integer of 1 or more and 4 or less. Also, in the above formula (a11), $R^{21a}$ represents a hydrogen atom, a hydroxyl group, a linear or branched alkyl group having 1 or more and 6 or less carbon atoms, or a linear or branched alkoxy group having 1 or more and 6 or less carbon atoms, and y represents an integer of 1 or more and 3 or less. Of these, trifluoromethane sulfonate, and perfluorobutane sulfonate are preferable in view of safety.

In addition, a nitrogen-containing moiety represented by the following formulae (a13) and (a14) may also be used for the anion moiety.

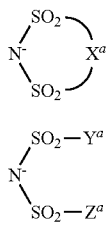

In the formulae (a13) and (a14), $X^a$ represents a linear or branched alkylene group in which at least one hydrogen atom is substituted with a fluorine atom, the carbon number of the alkylene group is 2 or more and 6 or less, preferably 3 or more and 5 or less, and most preferably the carbon number is 3. In addition, $Y^a$ and $Z^a$ each independently represent a linear or branched alkyl group of which at least one hydrogen atom is substituted with a fluorine atom, the number of carbon atoms of the alkyl group is 1 or more and 10 or less, preferably 1 or more and 7 or less, and more preferably 1 or more and 3 or less.

The smaller number of carbon atoms in the alkylene group of $X^a$, or in the alkyl group of $Y^a$ or $Z^a$ is preferred since the solubility into organic solvent is favorable.

In addition, a larger number of hydrogen atoms each substituted with a fluorine atom in the alkylene group of $X^a$, or in the alkyl group of $Y^a$ or $Z^a$ is preferred since the acid strength becomes greater. The percentage of fluorine atoms in the alkylene group or alkyl group, i.e., the fluorination rate is preferably 70% or more and 100% or less and more preferably 90% or more and 100% or less, and most preferable are perfluoroalkylene or perfluoroalkyl groups in which all of the hydrogen atoms are each substituted with a fluorine atom.

Examples of preferable compounds for onium salts having a naphthalene ring at their cation moieties include compounds represented by the following formulae (a15) and (a16).

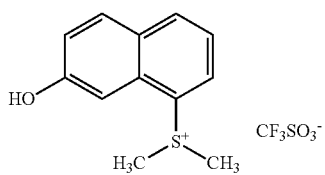

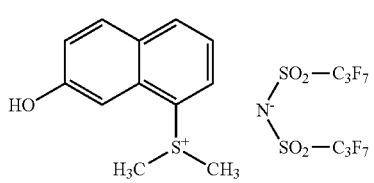

Also, the fifth aspect of the acid generator (A) include bissulfonyldiazomethanes such as bis(p-toluenesulfonyl)diazomethane, bis(1,1-dimethyl ethylsulfonyl)diazomethane, bis(cyclohexylsulfonyl)diazomethane and bis(2,4-dimethylphenylsulfonyl)diazomethane; nitrobenzyl derivatives such as 2-nitrobenzyl p-toluenesulfonate, 2,6-dinitrobenzyl p-toluenesulfonate, nitrobenzyl tosylate, dinitrobenzyl tosylate, nitrobenzyl sulfonate, nitrobenzyl carbonate and dinitrobenzyl carbonate; sulfonates such as pyrogalloltrimesylate, pyrogalloltritosylate, benzyltosylate, benzylsulfonate, N-methylsulfonyloxysuccinimide, N-trichloromethylsulfonyloxysuccinimide, N-phenylsulfonyloxymaleimide and N-methylsulfonyloxyphthalimide; trifluoromethane sulfonates such as N-(trifluoromethylsulfonyloxy)phthalimide, N-(trifluoromethylsulfonyloxy)-1,8-naphthalimide and N-(trifluoromethylsulfonyloxy)-4-butyl-1,8-naphthalimide; onium salts such as diphenyliodonium hexafluorophosphate, (4-methoxyphenyl)phenyliodonium trifluoromethanesulfonate, bis(p-tert-butylphenyl)iodonium trifluoromethanesulfonate, triphenylsulfonium hexafluorophosphate, (4-methoxyphenyl)diphenylsulfonium trifluoromethanesulfonate and (p-tert-butylphenyl)diphenylsulfonium trifluoromethanesulfonate; benzointosylates such as benzointosylate and α-methylbenzointosylate; other diphenyliodonium salts, triphenylsulfonium salts, phenyldiazonium salts, benzylcarbonates and the like.

This acid generator (A) may be used alone, or two or more types may be used in combination. Furthermore, the content of the acid generator (A) is preferably adjusted to 0.1% by mass or more and 10% by mass or less, and more preferably 0.5% by mass or more and 3% by mass or less, relative to the total mass of the solid component of the photosensitive resin composition. When the amount of the acid generator (A) used is adjusted to the range mentioned above, it is easy to prepare a photosensitive resin composition which is a uniform solution having satisfactory sensitivity and excellent storage stability.

<Resin (B)>

A resin (B) whose solubility in alkali increases under the action of acid is not particularly limited, and any resin whose solubility in alkali increases under the action of acid can be used. Among them, it is preferable to contain at least one resin selected from the group consisting of novolac resin (B1), polyhydroxystyrene resin (B2), and acrylic resin (B3).

[Novolac Resin (B1)]

As the novolak resin (B1), a resin including the constituent unit represented by the following formula (b1) may be used.

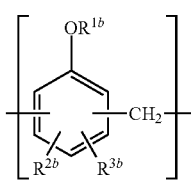

In the formula (b1), $R^{1b}$ represents an acid-dissociable dissolution-inhibiting group, and $R^{2b}$ and $R^{3b}$ each independently represent a hydrogen atom or an alkyl group having 1 or more and 6 or less carbon atoms.

The acid-dissociable dissolution-inhibiting group represented by the above $R^{1b}$ is preferably a group represented by the following formula (b2) or (b3), a linear, branched or cyclic alkyl group having 1 or more and 6 or less carbon atoms, a vinyloxyethyl group, a tetrahydropyranyl group, a tetrahydrofuranyl group, or a trialkylsilyl group.

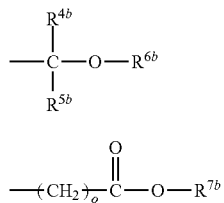

(b2)

(b3)

In the above formulae (b2) and (b3), $R^{4b}$ and $R^{5b}$ each independently represent a hydrogen atom, or a linear or branched alkyl group having 1 or more and 6 or less carbon atoms, $R^{6b}$ represents a linear, branched or cyclic alkyl group having 1 or more and 10 or less carbon atoms, $R^{7b}$ represents a linear, branched or cyclic alkyl group having 1 or more and 6 or less carbon atoms, and o represents 0 or 1.

Examples of the above linear or branched alkyl group include a methyl group, an ethyl group, a propyl group, an isopropyl group, an n-butyl group, an isobutyl group, a tert-butyl group, a pentyl group, an isopentyl group, a neopentyl group, and the like. Also, examples of the above cyclic alkyl group include a cyclopentyl group, a cyclohexyl group, and the like.

Specific examples of the acid-dissociable dissolution-inhibiting group represented by the above formula (b2) include a methoxyethyl group, ethoxyethyl group, n-propoxyethyl group, isopropoxyethyl group, n-butoxyethyl group, isobutoxyethyl group, tert-butoxyethyl group, cyclohexyloxyethyl group, methoxypropyl group, ethoxypropyl group, 1-methoxy-1-methylethyl group, 1-ethoxy-1-methylethyl group, and the like. Furthermore, specific examples of the acid-dissociable dissolution-inhibiting group represented by the above formula (b3) include a tert-butoxycarbonyl group, a tert-butoxycarbonylmethyl group, and the like. Examples of the above trialkylsilyl group include a trimethylsilyl group and tri-tert-butyldimethylsilyl group in which each alkyl group has 1 or more and 6 or less carbon atoms.

[Polyhydroxystyrene Resin (B2)]

As the polyhydroxystyrene resin (B2), a resin including a constituent unit represented by the following formula (b4) may be used.

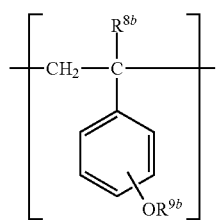

(b4)

In the above formula (b4), $R^{8b}$ represents a hydrogen atom or an alkyl group having 1 or more and 6 or less carbon atoms, and $R^{9b}$ represents an acid-dissociable dissolution-inhibiting group.

The above alkyl group having 1 or more and 6 or less carbon atoms may include, for example, linear, branched or cyclic alkyl groups having 1 or more and 6 or less carbon atoms. Examples of the linear or branched alkyl group include a methyl group, ethyl group, propyl group, isopropyl group, n-butyl group, isobutyl group, tert-butyl group, pentyl group, isopentyl group, neopentyl group, and the like. Examples of the cyclic alkyl group include a cyclopentyl group and cyclohexyl group.

The acid-dissociable dissolution-inhibiting group represented by the above $R^{9b}$ may be similar to the acid-dissociable dissolution-inhibiting groups exemplified in terms of the above formulae (b2) and (b3).

Furthermore, the polyhydroxystyrene resin (B2) may include another polymerizable compound as a constituent unit in order to moderately control physical or chemical properties. The polymerizable compound is exemplified by conventional radical polymerizable compounds and anion polymerizable compounds. Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxyl group and an ester bond such as 2-methacryloyloxyethyl succinic acid, 2-methacryloyloxyethyl maleic acid, 2-methacryloyloxyethyl phthalic acid and 2-methacryloyloxyethyl hexahydrophthalic acid; (meth)acrylic acid alkyl esters such as methyl (meth)acrylate, ethyl (meth)acrylate and butyl (meth)acrylate; (meth)acrylic acid hydroxyalkyl esters such as 2-hydroxyethyl (meth)acrylate and 2-hydroxypropyl (meth)acrylate; (meth)acrylic acid aryl esters such as phenyl (meth)acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; and amide bond-containing polymerizable compounds such as acrylamide and methacrylamide.

[Acrylic Resin (B3)]

An acrylic resin (B3) is not particularly limited as long as it is an acrylic resin the solubility of which in alkali increases under the action of acid, and has conventionally blended in various photosensitive resin compositions. Preferably, the acrylic resin (B3) contains a constituent unit (b-3) derived from, for example, an acrylic ester including an —SO$_2$-containing cyclic group or a lactone-containing cyclic group. In such a case, when a resist pattern is formed, the occurrence of footing can be suppressed.

(—SO$_2$-Containing Cyclic Group)

Herein, the "—SO$_2$-containing cyclic group" refers to a cyclic group having a cyclic group containing a ring including —SO$_2$— in the ring skeleton thereof, specifically a cyclic group in which the sulfur atom (S) in —SO$_2$— forms a part of the ring skeleton of the cyclic group. Considering a ring including —SO$_2$— in the ring skeleton thereof as the first ring, a group having that ring alone is called a monocyclic group, and a group further having another ring structure is called a polycyclic group regardless of its structure. The —SO$_2$-containing cyclic group may be monocyclic or polycyclic.

In particular, the —SO$_2$-containing cyclic group is preferably a cyclic group containing —O—SO$_2$— in the ring skeleton thereof, i.e., a cyclic group containing a sultone ring in which —O—S— in —O—SO$_2$— forms a part of the ring skeleton.

The number of carbon atoms in an —SO$_2$-containing cyclic group is preferably 3 or more and 30 or less, more preferably 4 or more and 20 or less, even more preferably 4 or more and 15 or less, and in particular preferably 4 or more and 12 or less. The above number of carbon atoms is the number of carbon atoms constituting a ring skeleton, and shall not include the number of carbon atoms in a substituent.

The —SO$_2$-containing cyclic group may be an —SO$_2$-containing aliphatic cyclic group or an —SO$_2$-containing aromatic cyclic group. It is preferably an —SO$_2$-containing aliphatic cyclic group.

—SO$_2$— containing aliphatic cyclic groups include a group in which at least one hydrogen atom is removed from an aliphatic hydrocarbon ring where a part of the carbon atoms constituting the ring skeleton thereof is(are) substituted with —SO$_2$— or —O—SO$_2$—. More specifically, they include a group in which at least one hydrogen atom is removed from an aliphatic hydrocarbon ring where —CH$_2$— constituting the ring skeleton thereof is substituted with —SO$_2$— and a group in which at least one hydrogen atom is removed from an aliphatic hydrocarbon ring where —CH$_2$—CH$_2$— constituting the ring thereof is substituted with —O—SO$_2$—.

The number of carbon atoms in the above alicyclic hydrocarbon ring is preferably 3 or more and 20 or less, more preferably 3 or more and 12 or less. The above alicyclic hydrocarbon ring may be polycyclic, or may be monocyclic. As the monocyclic alicyclic hydrocarbon group, preferred is a group in which two hydrogen atoms are removed from monocycloalkane having 3 or more and 6 or less carbon atoms. Examples of the above monocycloalkane can include cyclopentane, cyclohexane and the like. As the polycyclic alicyclic hydrocarbon ring, preferred is a group in which two hydrogen atoms are removed from polycycloalkane having 7 or more and 12 or less carbon atoms, and specific examples of the above polycycloalkane include adamantane, norbornane, isobornane, tricyclodecane, tetracyclododecane and the like.

The —SO$_2$-containing cyclic group may have a substituent. Examples of the above substituent include, for example, an alkyl group, an alkoxy group, a halogen atom, a halogenated alkyl group, a hydroxy group, an oxygen atom (=O), —COOR", OC(=O)R", a hydroxyalkyl group, a cyano group and the like.

For an alkyl group as the above substituent, preferred is an alkyl group having 1 or more and 6 or less carbon atoms. The above alkyl group is preferably linear or branched. Specific examples include a methyl group, an ethyl group, an n-propyl group, an isopropyl group, an n-butyl group, an isobutyl group, a tert-butyl group, an n-pentyl group, an isopentyl group, a neopentyl group, an n-hexyl group and the like. Among these, a methyl group or an ethyl group is preferred, and a methyl group is particularly preferred.

For an alkoxy group as the above substituent, preferred is an alkoxy group having 1 or more and 6 or less carbon atoms. The above alkoxy group is preferably linear or branched. Specific examples include a group in which an alkyl groups recited as an alkyl group for the above substituent is attached to the oxygen atom (—O—).

Halogen atoms as the above substituent include a fluorine atom, a chlorine atom, a bromine atom, an iodine atom and the like, and a fluorine atom is preferred.

Halogenated alkyl groups for the above substituent include a group in which a part or all of the hydrogen atoms in the above alkyl group is(are) substituted with the above halogen atom(s).

Halogenated alkyl groups as the above substituent include a group in which a part or all of the hydrogen atoms in the alkyl groups recited as an alkyl group for the above substituent is(are) substituted with the above halogen atom(s). As the above halogenated alkyl group, a fluorinated alkyl group is preferred, and a perfluoroalkyl group is particularly preferred.

R"s in the aforementioned —COOR" and —OC(=O)R" are either a hydrogen atom or a linear, branched or cyclic alkyl group having 1 or more and 15 or less carbon atoms.

In a case where R" is a linear or branched alkyl group, the number of carbon atoms in the above chain alkyl group is preferably 1 or more and 10 or less, more preferably 1 or more and 5 or less, and in particular preferably 1 or 2.

In a case where R" is a cyclic alkyl group, the number of carbon atoms in the above cyclic alkyl group is preferably 3 or more and 15 or less, more preferably 4 or more and 12 or less, and in particular preferably 5 or more and 10 or less. Specific examples can include a group in which one or more hydrogen atoms are removed from monocycloalkane; and polycycloalkane such as bicycloalkane, tricycloalkane, tetracycloalkane and the like optionally substituted with a fluorine atom or a fluorinated alkyl group. More specific examples include a group in which one or more hydrogen atoms are removed from monocycloalkane such as cyclopentane and cyclohexane; and polycycloalkane such as adamantane, norbornane, isobornane, tricyclodecane and tetracyclododecane.

For a hydroxyalkyl group as the above substituent, preferred is a hydroxyalkyl group having 1 or more and 6 or less carbon atoms. Specific examples include a group in which at least one of the hydrogen atoms in the alkyl groups recited as an alkyl group for the above substituent is substituted with a hydroxy group.

More specific examples of the —SO$_2$-containing cyclic group include the groups represented by the following formulae (3-1) to (3-4).

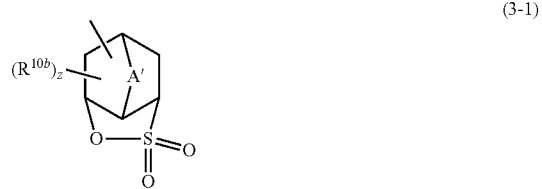

(3-1)

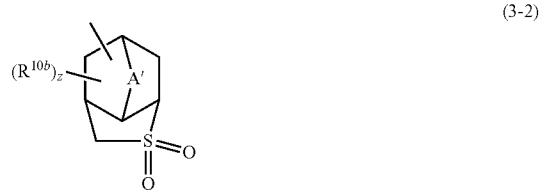

(3-2)

(3-3)

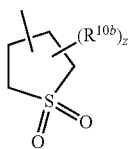
(3-4)

(In the formulae, A' represents an alkylene group having 1 or more and 5 or less carbon atoms optionally including an oxygen atom or a sulfur atom, an oxygen atom or a sulfur atom; z represents an integer of 0 or more and 2 or less; $R^{10b}$ represents an alkyl group, an alkoxy group, a halogenated alkyl group, a hydroxy group, —COOR", —OC(=O)R", a hydroxyalkyl group, or a cyano group; and R" represents a hydrogen atom or an alkyl group.)

In the above formulae (3-1) to (3-4), A' represents an alkylene group having 1 or more and 5 or less carbon atoms optionally including an oxygen atom (—O—) or a sulfur atom (—S—), an oxygen atom or a sulfur atom. As an alkylene group having 1 or more and 5 or less carbon atoms in A', a linear or branched alkylene group is preferred, and examples thereof include a methylene group, an ethylene group, an n-propylene group, an isopropylene group and the like.

In a case where the above alkylene group includes an oxygen atom or a sulfur atom, specific examples thereof include a group in which —O— or —S— is present at a terminal or between carbon atoms of the above alkylene group, for example, —O—CH₂—, —CH₂—O—CH₂—, —S—CH₂—, —CH₂—S—CH₂—, and the like. As A', an alkylene group having 1 or more and 5 or less carbon atoms or —O— is preferred, and an alkylene group having 1 or more and 5 or less carbon atoms is more preferred, and a methylene group is most preferred.

z may be any of 0, 1, and 2, and is most preferably 0. In a case where z is 2, a plurality of $R^{10b}$ may be the same, or may differ from each other.

Examples of an alkyl group, an alkoxy group, a halogenated alkyl group, —COOR", —OC(=O)R" and a hydroxyalkyl group in $R^{10b}$ include those similar to the groups described above for the alkyl group, the alkoxy group, the halogenated alkyl group, —COOR", —OC(=O)R" and the hydroxyalkyl group, respectively, which are recited as a substituent optionally contained in the —SO₂-containing cyclic group.

Below, specific cyclic groups represented by the above formulae (3-1) to (3-4) will be illustrated. Note here that "Ac" in the formulae represents an acetyl group.

(3-1-1)

(3-1-2)

(3-1-3)
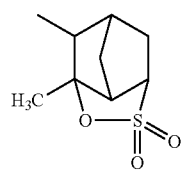

(3-1-4)
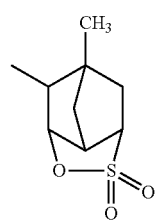

(3-1-5)
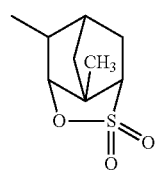

(3-1-6)
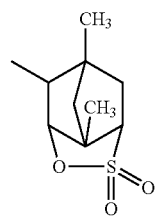

(3-1-7)
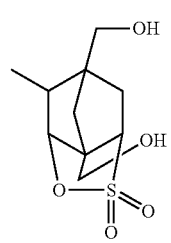

(3-1-8)
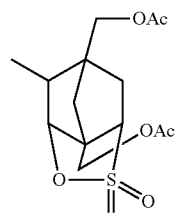

(3-1-9)
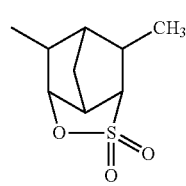

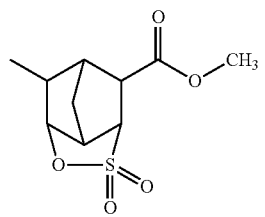 (3-1-10)
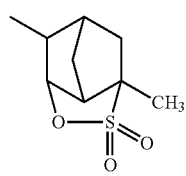 (3-1-11)
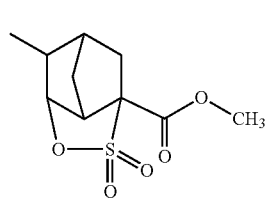 (3-1-12)
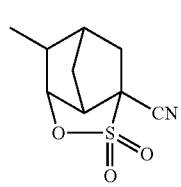 (3-1-13)
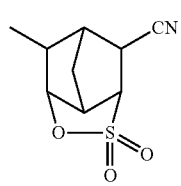 (3-1-14)
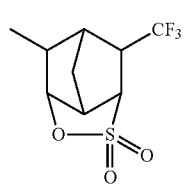 (3-1-15)
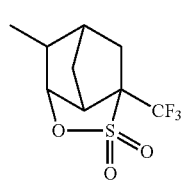 (3-1-16)
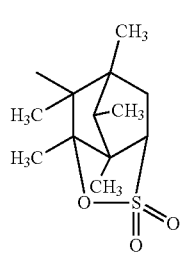 (3-1-17)
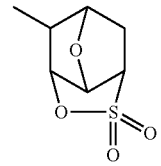 (3-1-18)
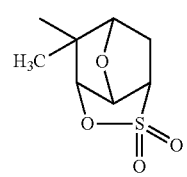 (3-1-19)
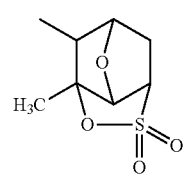 (3-1-20)
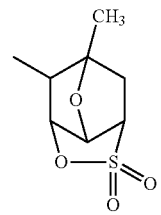 (3-1-21)
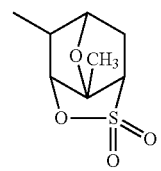 (3-1-22)
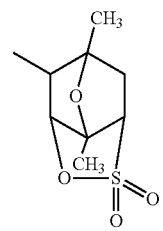 (3-1-23)
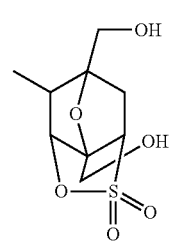 (3-1-24)
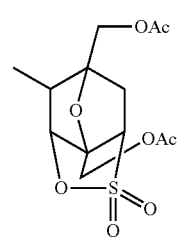 (3-1-25)

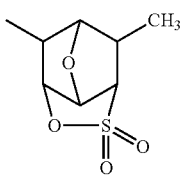

(3-1-26)

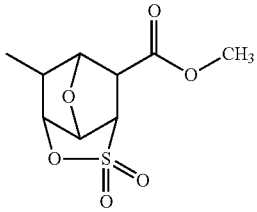

(3-1-27)

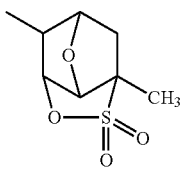

(3-1-28)

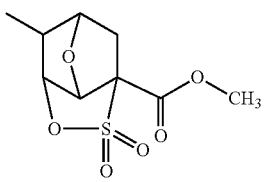

(3-1-29)

(3-1-30)

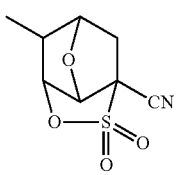

(3-1-31)

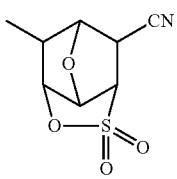

(3-1-32)

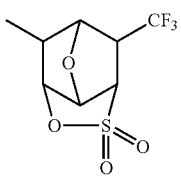

(3-1-33)

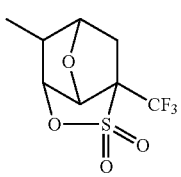

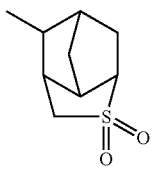

(3-2-1)

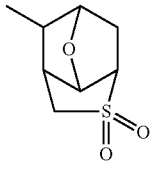

(3-2-2)

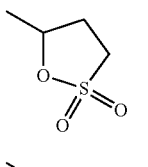

(3-3-1)

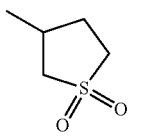

(3-4-1)

As the —SO$_2$-containing cyclic group, among those shown above, a group represented by the above formula (3-1) is preferred, and at least one selected from the group consisting of the groups represented by any of the aforementioned formulae (3-1-1), (3-1-18), (3-3-1) and (3-4-1) is more preferred, and a group represented by the aforementioned formula (3-1-1) is most preferred.

(Lactone-Containing Cyclic Group)

The "lactone-containing cyclic group" refers to a cyclic group containing a ring (lactone ring) including —O—C(=O)— in the ring skeleton thereof. Considering the lactone ring as the first ring, a group having that lactone ring alone is called a monocyclic group, and a group further having another ring structure is called a polycyclic group regardless of its structure. The lactone-containing cyclic group may be a monocyclic group, or may be a polycyclic group.

There is no particular limitation on the lactone-containing cyclic group in the constituent unit (b-3), and any cyclic group containing lactone can be used. Specifically, examples of the lactone-containing monocyclic groups include a group in which one hydrogen atom is removed from 4 to 6 membered ring lactone, for example, a group in which one hydrogen atom is removed from β-propiono lactone, a group in which one hydrogen atom is removed from γ-butyrolactone, a group in which one hydrogen atom is removed from δ-valerolactone and the like. Further, lactone-containing polycyclic groups include a group in which one hydrogen atom is removed from bicycloalkane, tricycloalkane and tetracycloalkane having a lactone ring.

As to the structure of the constituent unit (b-3), as long as the constituent unit (b-3) has an —SO$_2$-containing cyclic group or a lactone-containing cyclic group, the structure of parts other than an —SO$_2$-containing cyclic group and a lactone-containing cyclic group is not particularly limited. A preferred constituent unit (b-3) is at least one constituent unit selected from the group consisting of a constituent unit (b-3-S) derived from an acrylic acid ester including an —SO$_2$-containing cyclic group in which a hydrogen atom attached to the carbon atom in the α position may be substituted with a substituent; and a constituent unit (b-3-L) derived from an acrylic acid ester including a lactone-containing cyclic group in which the hydrogen atom attached to the carbon atom in the α position may be substituted with a substituent.

[Constituent Unit (b-3-S)]

More specifically, examples of the constituent unit (b-3-S) include one represented by the following formula (b-S1).

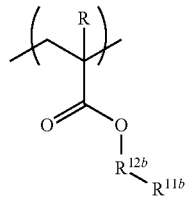

(b-S1)

(In the formula, R represents a hydrogen atom, an alkyl group having 1 or more 5 or less carbon atoms or a halogenated alkyl group having 1 or more 5 or less carbon atoms; and $R^{11b}$ represents an —SO$_2$-containing cyclic group; and $R^{12b}$ represents a single-bond or divalent linking group.)

In the formula (b-S1), R is similarly defined as above. $R^{11b}$ is similarly defined as in the —SO$_2$-containing cyclic group described above. $R^{12b}$ may be either a single-bond linking group or a divalent linking group. A divalent linking group is preferred due to the superior effect of the present invention.

There is no particular limitation on the divalent linking group in $R^{12b}$, and suitable examples include an optionally substituted divalent hydrocarbon group, a divalent linking group including a heteroatom, and the like.

Optionally Substituted Divalent Hydrocarbon Group

The hydrocarbon group as a divalent linking group may be an aliphatic hydrocarbon group, or may be an aromatic hydrocarbon group. The aliphatic hydrocarbon group means a hydrocarbon group without aromaticity. The above aliphatic hydrocarbon group may be saturated or may be unsaturated. Usually, a saturated hydrocarbon group is preferred. More specifically, examples of the above aliphatic hydrocarbon group include a linear or branched aliphatic hydrocarbon group, an aliphatic hydrocarbon group including a ring in the structure thereof and the like.

The number of carbon atoms in the linear or branched aliphatic hydrocarbon group is preferably 1 or more and 10 or less, more preferably 1 or more and 8 or less, and even more preferably 1 or more and 5 or less.

As the linear aliphatic hydrocarbon group, a linear alkylene group is preferred. Specific examples include a methylene group [—CH$_2$—], an ethylene group [—(CH$_2$)$_2$—], a trimethylene group [—(CH$_2$)$_3$—], a tetramethylene group [—(CH$_2$)$_4$—], a pentamethylene group [—(CH$_2$)$_5$-] and the like.

As the branched aliphatic hydrocarbon group, a branched alkylene group is preferred. Specific examples include alkyl alkylene groups such as alkyl methylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkyl ethylene groups such as —CH(CH$_3$)CH$_2$—, —CH(CH$_3$) CH(CH$_3$)—, —C(CH$_3$)$_2$CH$_2$—, —CH(CH$_2$CH$_3$) CH$_2$— and —C(CH$_2$CH$_3$)$_2$—CH$_2$—; alkyl trimethylene groups such as —CH(CH$_3$)CH$_2$CH$_2$— and —CH$_2$CH(CH$_3$)CH$_2$—; alkyl tetramethylene groups such as —CH(CH$_3$)CH$_2$CH$_2$CH$_2$— and —CH$_2$CH(CH$_3$) CH$_2$CH$_2$—; and the like. As an alkyl group in the alkyl alkylene group, a linear alkyl group having 1 or more and 5 or less carbon atoms is preferred.

The above linear or branched aliphatic hydrocarbon group may or may not have a substituent (a group or atom other than a hydrogen atom) which substitutes a hydrogen atom. Examples of the substituent include a fluorine atom, a fluorinated alkyl group having 1 or more and 5 or less carbon atoms substituted with a fluorine atom, an oxo group (=O) and the like.

Examples of the above aliphatic hydrocarbon group including a ring in the structure thereof include a cyclic aliphatic hydrocarbon group optionally including a hetero atom in the ring structure (a group in which two hydrogen atoms are removed from an aliphatic hydrocarbon ring); a group in which the above cyclic aliphatic hydrocarbon group is attached to an end of a linear or branched aliphatic hydrocarbon group; a group in which the above cyclic aliphatic hydrocarbon group is present in a linear or branched aliphatic hydrocarbon group along the chain; and the like. Examples of the above linear or branched aliphatic hydrocarbon group include groups similar to the above.

The number of carbon atoms in the cyclic aliphatic hydrocarbon group is preferably 3 or more and 20 or less, and more preferably 3 or more and 12 or less.

The cyclic aliphatic hydrocarbon group may be polycyclic, or may be monocyclic. As the monocyclic aliphatic hydrocarbon group, a group in which two hydrogen atoms are removed from monocycloalkane is preferred. The number of carbon atoms in the above monocycloalkane is preferably 3 or more and 6 or less. Specific examples include cyclopentane, cyclohexane and the like. As the polycyclic aliphatic hydrocarbon group, a group in which two hydrogen atoms are removed from polycycloalkane is preferred. The number of carbon atoms in the above polycycloalkane is preferably 7 or more and 12 or less. Specific examples include adamantane, norbornane, isobornane, tricyclodecane, tetracyclododecane and the like.

The cyclic aliphatic hydrocarbon group may or may not have a substituent which substitutes a hydrogen atom (a group or atom other than a hydrogen atom). Examples of the above substituent include an alkyl group, an alkoxy group, a halogen atom, a halogenated alkyl group, a hydroxy group, an oxo group (=O) and the like.

For an alkyl group as the above substituent, an alkyl group having 1 or more and 5 or less carbon atoms is preferred, and a methyl group, an ethyl group, a propyl group, an n-butyl group and a tert-butyl group are more preferred.

For an alkoxy group as the above substituent, an alkoxy group having 1 or more and 5 or less carbon atoms is preferred, and a methoxy group, an ethoxy group, an n-propoxy group, an iso-propoxy group, an n-butoxy group and a tert-butoxy group are more preferred, and a methoxy group and an ethoxy group are particularly preferred.

Halogen atoms as the above substituent include a fluorine atom, a chlorine atom, a bromine atom, an iodine atom and the like, and a fluorine atom is preferred.

Halogenated alkyl groups as the above substituent include a group in which a part or all of hydrogen atoms in the aforementioned alkyl group is(are) substituted with the above halogen atom(s).

In the cyclic aliphatic hydrocarbon group, a part of carbon atoms constituting the ring structure thereof may be substituted with —O—, or —S—. As the substituent including the above hetero atom, preferred are —O—, —C(=O)—O—, —S—, —S(=O)$_2$— and —S(=O)$_2$—O—.

The aromatic hydrocarbon group as the divalent hydrocarbon group is a divalent hydrocarbon group having at least one aromatic ring, and may have a substituent. There is no particular limitation on the aromatic ring as long as it is a cyclic conjugated system having a 4n+2 n electrons, and it may be monocyclic or may be polycyclic. The number of carbon atoms in the aromatic ring is preferably 5 or more and 30 or less, more preferably 5 or more and 20 or less, further more preferably 6 or more and 15 or less, and particularly preferably 6 or more and 12 or less. However, the number of carbon atoms in a substituent shall not be included in the above number of carbon atoms.

Specifically, aromatic rings include aromatic hydrocarbon rings such as benzene, naphthalene, anthracene and phenanthrene; aromatic heterocycles in which a part of the carbon atoms constituting the above aromatic hydrocarbon ring is(are) substituted with hetero atom(s). Hetero atoms in the aromatic heterocycle include an oxygen atom, a sulfur atom, a nitrogen atom and the like. Specifically, aromatic heterocycles include a pyridine ring, a thiophene ring, and the like.

Specific examples of the aromatic hydrocarbon group as a divalent hydrocarbon group include a group in which two hydrogen atoms are removed from the above aromatic hydrocarbon ring or the above aromatic heterocycle (an arylene group or a heteroarylene group); a group in which two hydrogen atoms are removed from an aromatic compound including two or more aromatic rings (for example, biphenyl, fluorene and the like); a group in which one hydrogen atom from a group where one hydrogen atom is removed from the above aromatic hydrocarbon ring or the above aromatic heterocycle (an aryl group or a heteroaryl group) is substituted with an alkylene group (for example, a group in which one hydrogen atom is further removed from an aryl group in an arylalkyl group such as a benzyl group, a phenethyl group, a 1-naphthylmethyl group, a 2-naphthylmethyl group, a 1-naphthylethyl group and a 2-naphthylethyl group); and the like.

The number of carbon atoms in the above alkylene group bonded to an aryl group or a heteroaryl group is preferably 1 or more and 4 or less, more preferably 1 or more and 2 or less, and particularly preferably 1.

In the above aromatic hydrocarbon group, a hydrogen atom of the above aromatic hydrocarbon group may be substituted with a substituent. For example, a hydrogen atom attached to an aromatic ring in the above aromatic hydrocarbon group may be substituted with a substituent. Examples of the substituent include an alkyl group, an alkoxy group, a halogen atom, a halogenated alkyl group, a hydroxy group, an oxo group (=O) and the like.

For an alkyl group as the above substituent, an alkyl group having 1 or more and 5 or less carbon atoms is preferred, and a methyl group, an ethyl group, an n-propyl group, an n-butyl group and a tert-butyl group are more preferred.

For an alkoxy group as the above substituent, an alkoxy group having 1 or more and 5 or less carbon atoms is preferred, and a methoxy group, an ethoxy group, an n-propoxy group, an iso-propoxy group, an n-butoxy group and a tert-butoxy group are preferred, and a methoxy group and an ethoxy group are more preferred.

Halogen atoms as the above substituent include a fluorine atom, a chlorine atom, a bromine atom, an iodine atom and the like, and a fluorine atom is preferred.

Halogenated alkyl groups as the above substituent include a group in which a part or all of hydrogen atoms in the aforementioned alkyl group is(are) substituted with the above halogen atom(s).

Divalent Linking Group Including Hetero Atom

A hetero atom in the divalent linking group including a hetero atom is an atom other than a carbon atom and a hydrogen atom, and examples thereof include an oxygen atom, a nitrogen atom, a sulfur atom, a halogen atom and the like.

Specific examples of the divalent linking group including a hetero atom include non-hydrocarbon based linking groups such as —O—, —C(=O)—, —C(=O)—O—, —O—C(=O)—O—, —S—, —S(=O)$_2$—, —S(=O)$_2$—O—, —NH—, —NH—C(=O)—, —NH—C(=NH)—, =N—, and combinations of at least one of these non-hydrocarbon based linking groups and a divalent hydrocarbon group and the like. Examples of the above divalent hydrocarbon group include those similar to the aforementioned divalent hydrocarbon groups optionally having a substituent, and linear or branched aliphatic hydrocarbon groups are preferred.

Among those described above, —NH— in —C(=O)—NH—, and H in —NH— and —NH—C(=NH)— may be substituted with a substituent such as an alkyl group or an acyl group, respectively. The number of carbon atoms in the above substituent is preferably 1 or more and 10 or less, more preferably 1 or more and 8 or less, and in particular preferably 1 or more and 5 or less.

As a divalent linking group in $R^{12b}$, a linear or branched alkylene group, a cyclic aliphatic hydrocarbon group, or a divalent linking group including a hetero atom is preferred.

In a case where the divalent linking group in $R^{12b}$ is a linear or branched alkylene group, the number of carbon atoms in the above alkylene group is preferably 1 or more and 10 or less, more preferably 1 or more and 6 or less, in particular preferably 1 or more and 4 or less, and most preferably 1 or more and 3 or less. Specific examples include groups similar to the linear alkylene groups or branched alkylene groups recited as a linear and branched aliphatic hydrocarbon group in the description of the "divalent hydrocarbon group optionally having a substituent" as the aforementioned divalent linking group.

In a case where the divalent linking group in $R^{12b}$ is an cyclic aliphatic hydrocarbon group, examples of the above cyclic aliphatic hydrocarbon group include groups similar to the cyclic aliphatic hydrocarbon groups recited as the "aliphatic hydrocarbon group including a ring in the structure" in the description of the "divalent hydrocarbon group optionally having a substituent" as the aforementioned divalent linking group.

As the above cyclic aliphatic hydrocarbon group, particularly preferred is a group in which two or more hydrogen atoms are removed from cyclopentane, cyclohexane, norbornane, isobornane, adamantane, tricyclodecane or tetracyclododecane.

In a case where the divalent linking group in $R^{12b}$ is a divalent linking group including a hetero atom, groups preferred as the above linking groups include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O— and a group represented by the general formula —Y$^1$—O—Y$^2$—, —[Y—C(=O)—O]$_{m'}$—Y$^2$— or —Y$^1$—O—C(=O)—Y$_2$— (wherein Y$^1$ and Y$^2$ are divalent hydrocarbon groups each independently, optionally having a substituent, and O represents an oxygen atom, and m' is an integer of 0 or more and 3 or less).

In a case where the divalent linking group in $R^{12b}$ is —NH—, the hydrogen atom in —NH— may be substituted with a substituent such as an alkyl group or an acyl group. The number of carbon atoms in the above substituent (an alkyl group, an acyl group and the like) is preferably 1 or more and 10 or less, more preferably 1 or more and 8 or less, and in particular preferably 1 or more and 5 or less.

$Y^1$ and $Y^2$ in the formula $Y^1$—O—$Y^2$—, —[$Y^1$—C(=O)—O]$_{m'}$—$Y^2$— or —$Y^1$—O—C(=O)—$Y^2$— are divalent hydrocarbon groups each independently, optionally having a substituent. Examples of the above divalent hydrocarbon group include groups similar to the "divalent hydrocarbon group optionally having a substituent" recited in the description of the above divalent linking group.

As $Y^1$, a linear aliphatic hydrocarbon group is preferred, and a linear alkylene group is more preferred, and a linear alkylene group having 1 or more and 5 or less carbon atoms is more preferred, and a methylene group and an ethylene group are particularly preferred.

As $Y^2$, a linear or branched aliphatic hydrocarbon group is preferred, and a methylene group, an ethylene group and an alkylmethylene group are more preferred. The alkyl group in the above alkylmethylene group is preferably a linear alkyl group having 1 or more and 5 or less carbon atoms, more preferably a linear alkyl group having 1 or more and 3 or less carbon atoms, and particularly preferably a methyl group.

In a group represented by the formula —[$Y^1$—C(=O)—O]$_{m'}$—$Y^2$—, m' is an integer of 0 or more and 3 or less, preferably an integer of 0 or more and 2 or less, more preferably 0 or 1, and particularly preferably 1. In other words, as a group represented by the formula —[$Y^1$—C(=O)—O]$_{m'}$—$Y^2$—, a group represented by the formula —$Y^1$—C(=O)—O—$Y^2$— is particularly preferred. Among these, a group represented by the formula —(CH$_2$)$_{a'}$—C(=O)—O—(CH$_2$)$_{b'}$— is preferred. In the above formula, a' is an integer of 1 or more and 10 or less, preferably an integer of 1 or more and 8 or less, more preferably an integer of 1 or more and 5 or less, even more preferably 1 or 2, and most preferably 1.

b' is an integer of 1 or more and 10 or less, preferably an integer of 1 or more and 8 or less, more preferably an integer of 1 or more and 5 or less, even more preferably 1 or 2, and most preferably 1.

With regard to the divalent linking group in $R^{12b}$, an organic group including a combination of at least one non-hydrocarbon group and a divalent hydrocarbon group is preferred as the divalent linking group including a hetero atom. Among these, a linear chain group having an oxygen atom as a hetero atom, for example, a group including an ether bond or an ester bond is preferred, and a group represented by the aforementioned formula —$Y^1$—O—$Y^2$—, —[$Y^1$—C(=O)—O]$_{m'}$—$Y^2$— or —$Y^1$—O—C(=O)—$Y^2$— is more preferred, and a group represented by the aforementioned formula —[$Y^1$—C(=O)—O]$_{m'}$—$Y^2$— or —$Y^1$—O—C(=O)—$Y^2$— is particularly preferred.

As the divalent linking group in $R^{12b}$, a group including an alkylene group or an ester bond (—C(=O)—O—) is preferred.

The above alkylene group is preferably a linear or branched alkylene group. Suitable examples of the above linear aliphatic hydrocarbon group include a methylene group [—CH$_2$—], an ethylene group [—(CH$_2$)$_2$—], a trimethylene group [—(CH$_2$)$_3$—], a tetramethylene group [—(CH$_2$)$_4$—], a pentamethylene group [—(CH$_2$)$_5$-] and the like. Suitable examples of the above branched alkylene group include alkyl alkylene groups such as alkyl methylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkyl ethylene groups such as —CH(CH$_3$)CH$_2$—, —CH(CH$_3$)CH(CH$_3$)—, —C(CH$_3$)$_2$CH$_2$—, —CH(CH$_2$CH$_3$) CH$_2$— and —C(CH$_2$CH$_3$)$_2$—CH$_2$—; alkyl trimethylene groups such as —CH(CH$_3$)CH$_2$CH$_2$— and —CH$_2$CH(CH$_3$)CH$_2$—; alkyl tetramethylene groups such as —CH(CH$_3$)CH$_2$CH$_2$CH$_2$— and —CH$_2$CH(CH$_3$) CH$_2$CH$_2$—.

As the divalent linking group including an ester bond, particularly preferred is a group represented by the formula: —$R^{13b}$—C(=O)—O—[wherein $R^{13b}$ represents a divalent linking group.]. In other words, the constituent unit (b-3-S) is preferably a constituent unit represented by the following formula (b-S1-1).

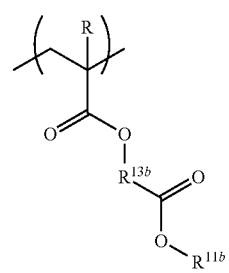

(b-S1-1)

(In the formula, R and $R^{11b}$ are each similar to the above, and $R^{13b}$ represents a divalent linking group.)

There is no particular limitation for $R^{13b}$, examples thereof include groups similar to the aforementioned divalent linking group in $R^{12b}$. As the divalent linking group in $R^{13b}$, a linear or branched alkylene group, an aliphatic hydrocarbon group including a ring in the structure, or a divalent linking group including a hetero atom is preferred, and a linear or branched alkylene group or a divalent linking group including an oxygen atom as a hetero atom is preferred.

As the linear alkylene group, a methylene group or an ethylene group is preferred, and a methylene group is particularly preferred. As the branched alkylene group, an alkylmethylene group or an alkylethylene group is preferred, and —CH(CH$_3$)—, —C(CH$_3$)$_2$— or —C(CH$_3$)$_2$CH$_2$— is particularly preferred.

As the divalent linking group including an oxygen atom, a divalent linking group including an ether bond or an ester bond is preferred, and the aforementioned —$Y^1$—O—$Y^2$—, —[$Y^1$—C(=O)—O]$_{m'}$—$Y^2$— or —$Y^1$—O—C(=O)—$Y^2$— is more preferred. $Y^1$ and $Y^2$ are each independently divalent hydrocarbon groups optionally having a substituent, and m' is an integer of 0 or more and 3 or less. Among these, —$Y^1$—O—C(=O)—$Y^2$— is preferred, and a group represented by —(CH$_2$)$_c$—O—C(=O)—(CH$_2$)$_d$— is particularly preferred.

c is an integer of 1 or more and 5 or less, and 1 or 2 is preferred.

d is an integer of 1 or more and 5 or less, and 1 or 2 is preferred.

As the constituent unit (b-3-S), in particular, one represented by the following formula (b-S1-11) or (b-S1-12) is preferred, and one represented by the formula (b-S1-12) is more preferred.

(b-S1-11)

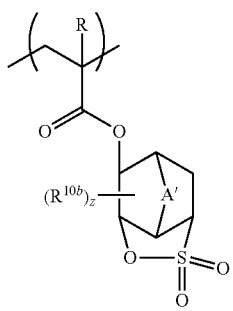

(b-S1-12)

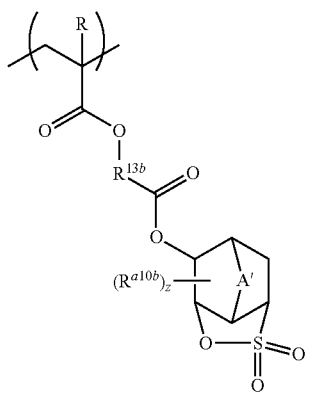

(In the formulae, R, A', $R^{10b}$, z and $R^{13b}$ are each the same as the above.)

In the formula (b-S1-11), A' is preferably a methylene group, an oxygen atom (—O—) or a sulfur atom (—S—).

As $R^{13b}$, preferred is a linear or branched alkylene group or a divalent linking group including an oxygen atom. Examples of the linear or branched alkylene group and the divalent linking group including an oxygen atom in $R^{13b}$ include groups similar to the aforementioned linear or branched alkylene group and the aforementioned divalent linking group including an oxygen atom, respectively.

As the constituent unit represented by the formula (b-S1-12), particularly preferred is one represented by the following formula (b-S1-12a) or (b-S1-12b)

(b-S1-12a)

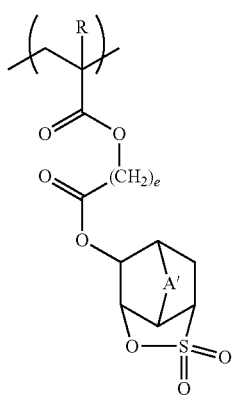

(b-S1-12b)

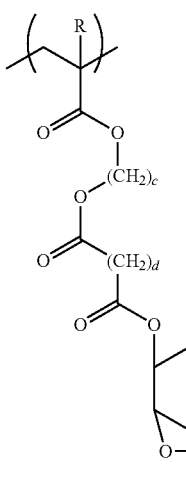

(In the formulae, R and A' are each the same as the above, and c to e are each independently an integer of 1 or more and 3 or less.)

[Constituent Unit (b-3-L)]

Examples of the constituent unit (b-3-L) include, for example, a constituent unit in which $R^{11b}$ in the aforementioned formula (b-S1) is substituted with a lactone-containing cyclic group. More specifically they include those represented by the following formulae (b-L1) to (b-L5).

(b-L1)

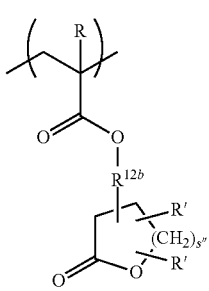

(b-L2)

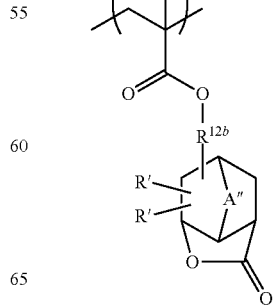

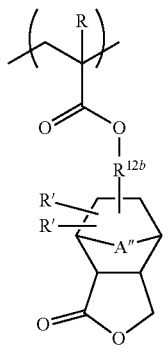
(b-L3)

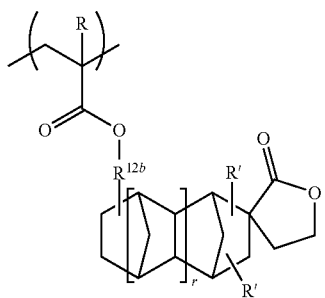
(b-L4)

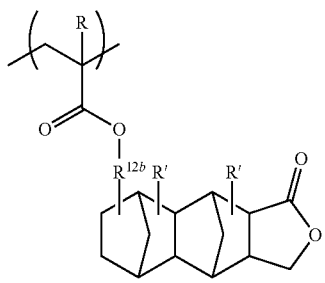
(b-L5)

(In the formulae, R represents a hydrogen atom, an alkyl group having 1 or more and 5 or less carbon atoms or a halogenated alkyl group having 1 or more and 5 or less carbon atoms; R' represents each independently a hydrogen atom, an alkyl group, an alkoxy group, a halogenated alkyl group, a hydroxy group, —COOR", —OC(=O)R", a hydroxyalkyl group or a cyano group, and R" represents a hydrogen atom or an alkyl group; $R^{12b}$ represents a single bond or divalent linking group, and s" is an integer of 0 or more and 2 or less; A" represents an alkylene group having 1 or more and 5 or less carbon atoms optionally including an oxygen atom or a sulfur atom, an oxygen atom or a sulfur atom; and r is 0 or 1.)

R in the formulae (b-L1) to (b-L5) is the same as the above. Examples of the alkyl group, the alkoxy group, the halogenated alkyl group, —COOR", —OC(=O)R" and the hydroxyalkyl group in R' include groups similar to those described for the alkyl group, the alkoxy group, the halogenated alkyl group, —COOR", —OC(=O)R" and the hydroxyalkyl group recited as a substituent which the —SO$_2$-containing cyclic group may have, respectively.

R' is preferably a hydrogen atom in view of easy industrial availability and the like. The alkyl group in R" may be any of a linear, branched or cyclic chain. In a case where R" is a linear or branched alkyl group, the number of carbon atoms is preferably 1 or more and 10 or less, and more preferably 1 or more and 5 or less. In a case where R" is a cyclic alkyl group, the number of carbon atoms is preferably 3 or more and 15 or less, more preferably 4 or more and 12 or less, and most preferably 5 or more and 10 or less. Specific examples include a group in which one or more hydrogen atoms are removed from monocycloalkane and polycycloalkane such as bicycloalkane, tricycloalkane, tetracycloalkane and the like optionally substituted with a fluorine atom or a fluorinated alkyl group. Specific examples include a group in which one or more hydrogen atoms are removed from monocycloalkane such as cyclopentane and cyclohexane; and polycycloalkane such as adamantane, norbornane, isobornane, tricyclodecane and tetracyclododecane; and the like. Examples of A" include groups similar to A' in the aforementioned formula (3-1). A" is preferably an alkylene group having 1 to 5 carbon atoms, an oxygen atom (—O—) or a sulfur atom (—S—), more preferably an alkylene group having 1 or more and 5 or less carbon atoms or —O—. As the alkylene group having 1 or more and 5 or less carbon atoms, a methylene group or a dimethylmethylene group is more preferred, and a methylene group is most preferred.

$R^{12b}$ is similar to $R^{12b}$ in the aforementioned formula (b-S1) In the formula (b-L1), s" is preferably 1 or 2. Below, specific examples of the constituent units represented by the aforementioned formulae (b-L1) to (b-L3) will be illustrated. In each of the following formulae, $R^\alpha$ represents a hydrogen atom, a methyl group or a trifluoromethyl group.

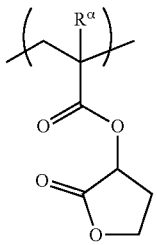
(b-L1-1)

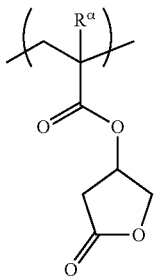
(b-L1-2)

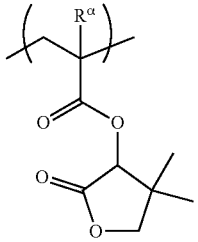
(b-L1-3)

(b-L1-4)
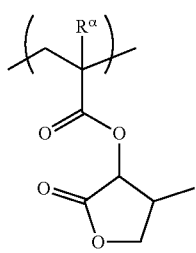
(b-L1-5)
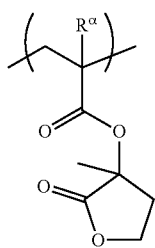
(b-L1-6)
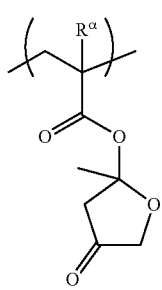
(b-L1-7)
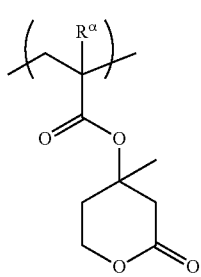
(b-L1-8)
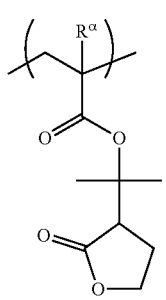
(b-L1-9)
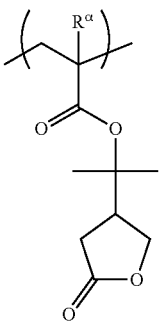
(b-L1-10)
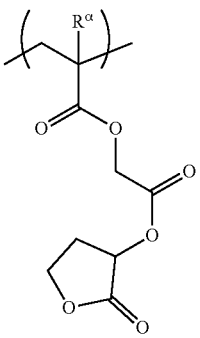
(b-L1-11)
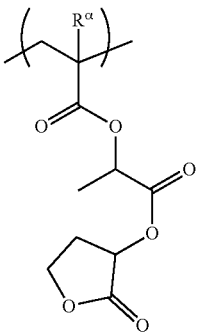
(b-L1-12)
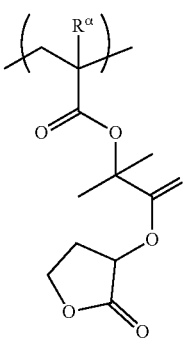

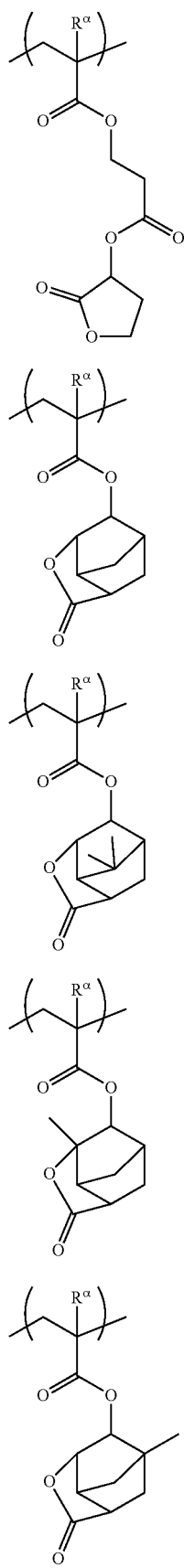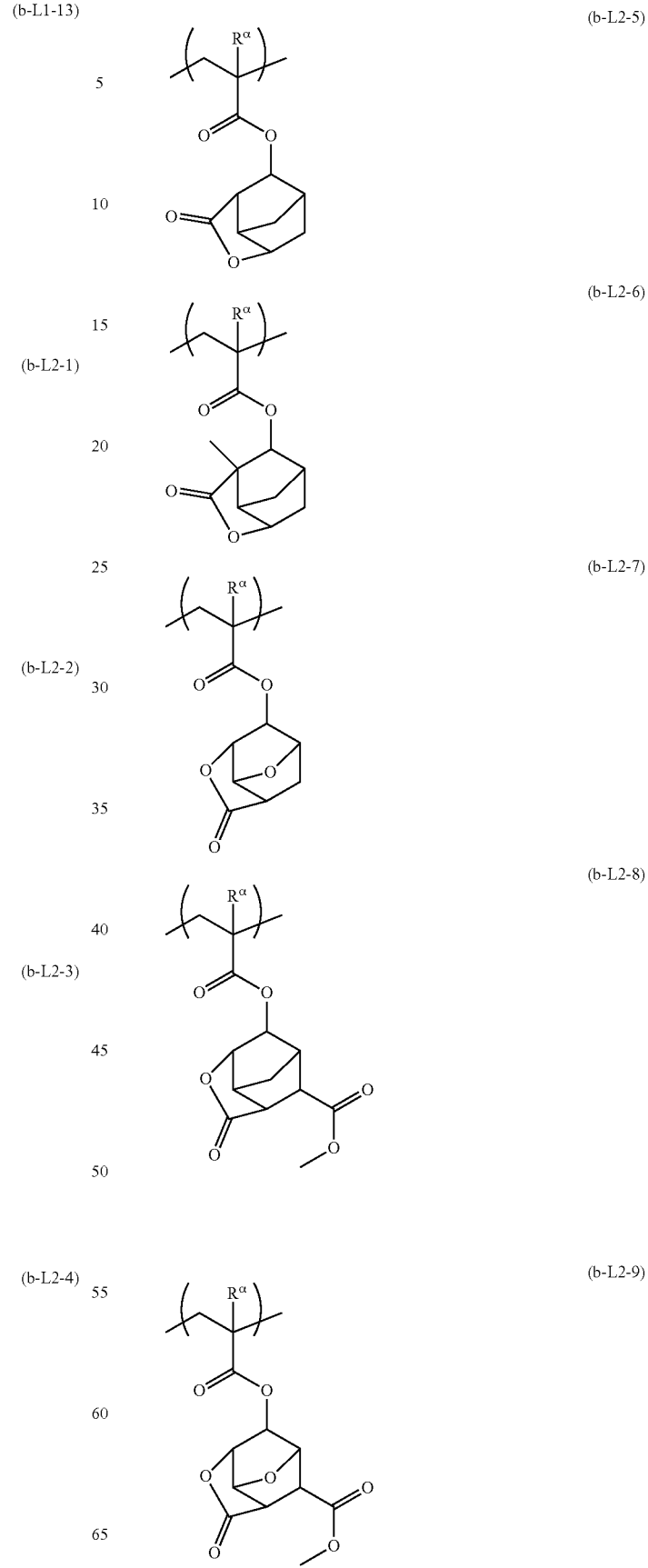

(b-L2-10) 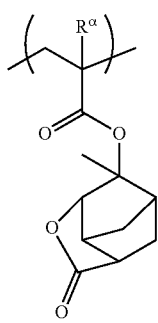
(b-L2-11) 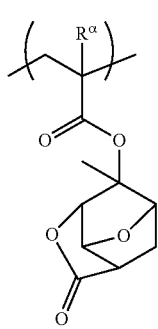
(b-L2-12) 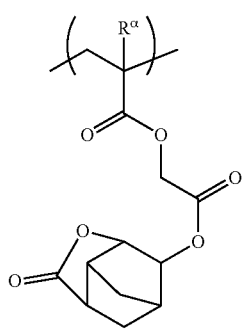
(b-L2-13) 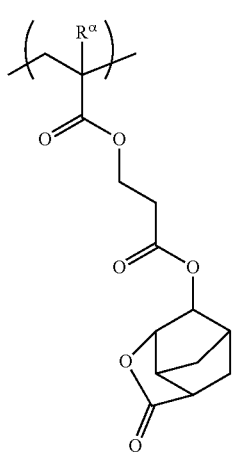
(b-L2-14) 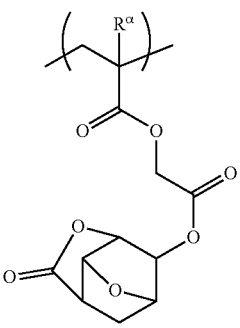
(b-L2-15) 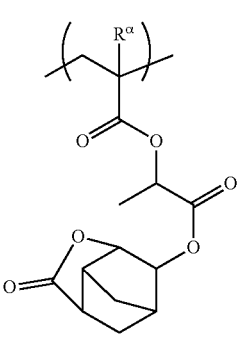
(b-L2-16)
(b-L2-17)

(b-L3-1)

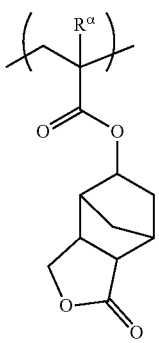

(b-L3-2)

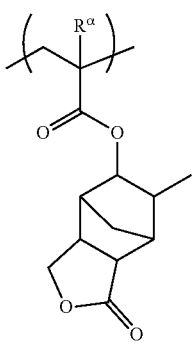

(b-L3-3)

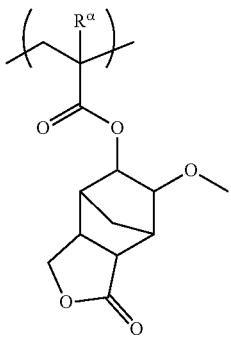

(b-L3-4)

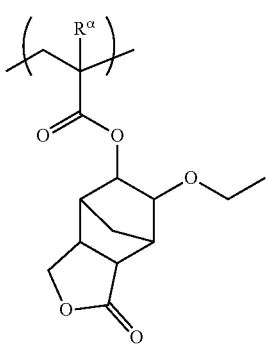

(b-L3-5)

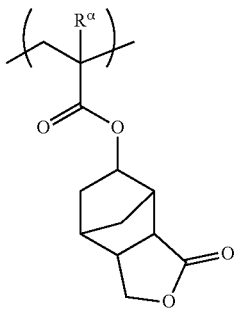

As the constituent unit (b-3a-L), at least one selected from the group consisting of the constituent units represented by the aforementioned formulae (b-L1) to (b-L5) is preferred, and at least one selected from the group consisting of the constituent units represented by the formulae (b-L1) to (b-L3) is more preferred, and at least one selected from the group consisting of the constituent units represented by the aforementioned formula (b-L1) or (b-L3) is particularly preferred. Among these, at least one selected from the group consisting of the constituent units represented by the aforementioned formulae (b-L1-1), (b-L1-2), (b-L2-1), (b-L2-7), (b-L2-12), (b-L2-14), (b-L3-1) and (b-L3-5) is preferred.

Further, as the constituent unit (b-3-L), the constituent units represented by following formulae (b-L6) to (b-L7) are also preferred.

(b-L6)

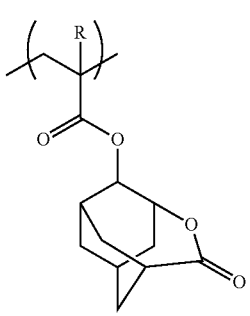

(b-L7)

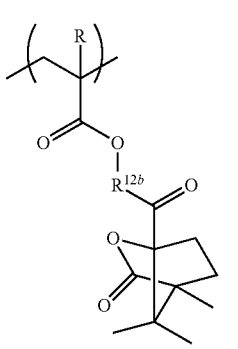

R and $R^{12b}$ in the formulae (b-L6) and (b-L7) are the same as the above.

Further, the acrylic resin (B3) includes constituent units represented by the following formulae (b5) to (b7), having an acid dissociable group, as constituent units that enhance the solubility of the acrylic resin (B3) in alkali under the action of acid.

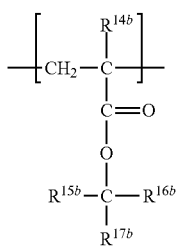
(b5)

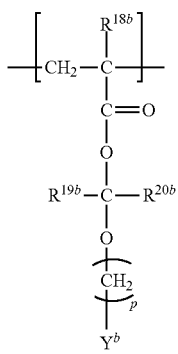
(b6)

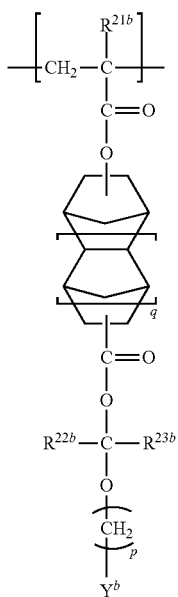
(b7)

In the above formulae (b5) to (b7), $R^{14b}$ and $R^{18b}$ to $R^{23b}$ each independently represent a hydrogen atom, a linear or branched alkyl group having 1 or more and 6 or less carbon atoms, a fluorine atom, or a linear or branched fluorinated alkyl group having 1 or more and 6 or less carbon atoms; $R^{15b}$ to $R^{17b}$ each independently represent a linear or branched alkyl group having 1 or more and 6 or less carbon atoms, a linear or branched fluorinated alkyl group having 1 or more and 6 or less carbon atoms, or an aliphatic cyclic group having 5 or more and 20 or less carbon atoms, and each independently represent a linear or branched alkyl group having 1 or more and 6 or less carbon atoms, or a linear or branched fluorinated alkyl group having 1 or more and 6 or less carbon atoms; and $R^{16b}$ and $R^{17b}$ may be bonded to each other to form a hydrocarbon ring having 5 or more and 20 or less carbon atoms together with the carbon atom to which both the groups are bonded; $Y^b$ represents an optionally substituted aliphatic group or alkyl group; p is an integer of 0 or more and 4 or less; and q is 0 or 1.

Note here that examples of the linear or branched alkyl group include a methyl group, ethyl group, propyl group, isopropyl group, n-butyl group, isobutyl group, tert-butyl group, pentyl group, isopentyl group, neopentyl group, and the like. Furthermore, the fluorinated alkyl group refers to the abovementioned alkyl groups of which the hydrogen atoms are partially or entirely substituted with fluorine atoms. Specific examples of aliphatic cyclic groups include groups obtained by removing one or more hydrogen atoms from monocycloalkanes or polycycloalkanes such as bicycloalkanes, tricycloalkanes, and tetracycloalkanes. Specifically, groups obtained by removing one hydrogen atom from a monocycloalkane such as cyclopentane, cyclohexane, cycloheptane, or cyclooctane, or a polycycloalkane such as adamantane, norbornane, isobornane, tricyclodecane, or tetracyclododecane may be mentioned. In particular, groups obtained by removing one hydrogen atom from cyclohexane or adamantane (which may further be substituted) are preferred.

When $R^{16b}$ and $R^{17b}$ do not combine with each other to form a hydrocarbon ring, the above $R^{15b}$, $R^{16b}$, and $R^{17b}$ preferably represent a linear or branched alkyl group having 2 or more and 4 or less carbon atoms, for example, from the viewpoints of a high contrast and favorable resolution and depth of focus. The above $R^{19b}$, $R^{20b}$, $R^{22b}$, and $R^{23b}$ preferably represent a hydrogen atom or a methyl group.

The above $R^{16b}$ and $R^{17b}$ may form an aliphatic cyclic group having 5 or more and 20 or less carbon atoms together with a carbon atom to which the both are attached. Specific examples of such an alicyclic group are the groups of monocycloalkanes and polycycloalkanes such as bicycloalkanes, tricycloalkanes and tetracycloalkanes from which one or more hydrogen atoms are removed. Specific examples thereof are the groups of monocycloalkanes such as cyclopentane, cyclohexane, cycloheptane and cyclooctane and polycycloalkanes such as adamantane, norbornane, isobornane, tricyclodecane and tetracyclododecane from which one or more hydrogen atoms are removed. Particularly preferable are the groups of cyclohexane and adamantane from which one or more hydrogen atoms are removed (that may further have a substituent).

Further, in a case where an aliphatic cyclic group to be formed with the above $R^{16b}$ and $R^{17b}$ has a substituent on the ring skeleton thereof, examples of the substituent include a polar group such as a hydroxy group, a carboxyl group, a cyano group and an oxygen atom (=O), and a linear or branched alkyl group having 1 or more and 4 or less carbon atoms. As the polar group, an oxygen atom (=O) is particularly preferred.

The above $Y^b$ is an alicyclic group or an alkyl group; and examples thereof are the groups of monocycloalkanes and polycycloalkanes such as bicycloalkanes, tricycloalkanes and tetracycloalkanes from which one or more hydrogen atoms are removed. Specific examples thereof are the groups of monocycloalkanes such as cyclopentane, cyclohexane, cycloheptane and cyclooctane, and polycycloalkanes such as adamantane, norbornane, isobornane, tricyclodecane and tetracyclododecane from which one or more hydrogen atoms are removed. Particularly preferable is the group of adamantane from which one or more hydrogen atoms are removed (that may further have a substituent).

When the alicyclic group of the above $Y^b$ has a substituent on the ring skeleton, the substituent is exemplified by polar groups such as a hydroxy group, carboxyl group, cyano group and oxygen atom (=O), and linear or branched alkyl groups having 1 or more and 4 or less carbon atoms. The polar group is preferably an oxygen atom (=O) in particular.

When $Y^b$ is an alkyl group, it is preferably a linear or branched alkyl group having 1 or more and 20 or less carbon atoms, and more preferably 6 or more and 15 or less carbon atoms. The alkyl group is an alkoxyalkyl group particularly preferable. Examples of such an alkoxyalkyl group include a 1-methoxyethyl group, 1-ethoxyethyl group, 1-n-propoxyethyl group, 1-isopropoxyethyl group, 1-n-butoxyethyl group, 1-isobutoxyethyl group, 1-tert-butoxyethyl group, 1-methoxypropyl group, 1-ethoxypropyl group, 1-methoxy-1-methylethyl group, 1-ethoxy-1-methylethyl group, and the like.

Preferable specific examples of the constituent unit represented by the above formula (b5) include constituent units represented by the following formulae (b5-1) to (b5-33).

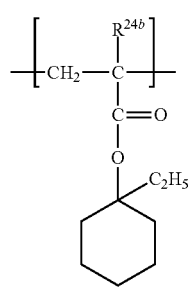

(b5-1)

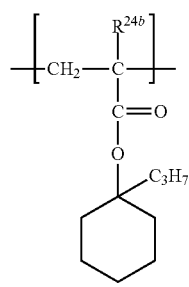

(b5-2)

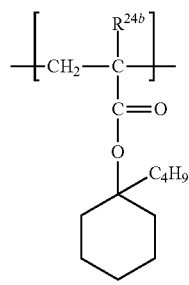

(b5-3)

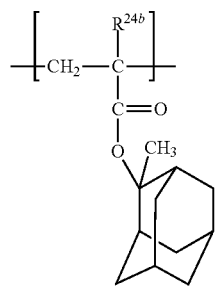

(b5-4)

-continued

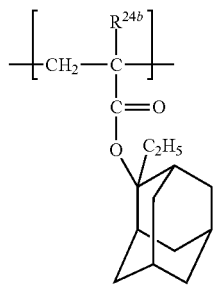

(b5-5)

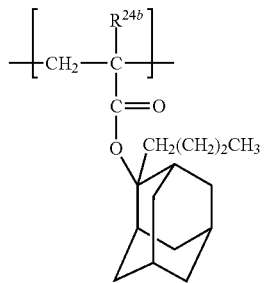

(b5-6)

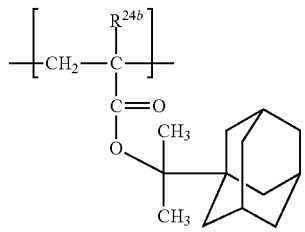

(b5-7)

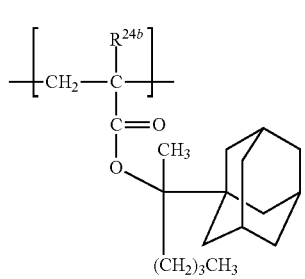

(b5-8)

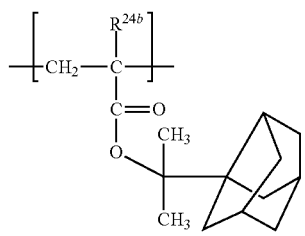

(b5-9)

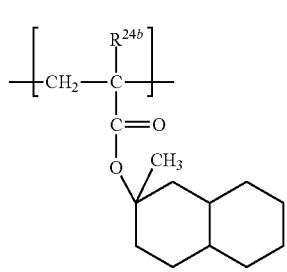

(b5-10)

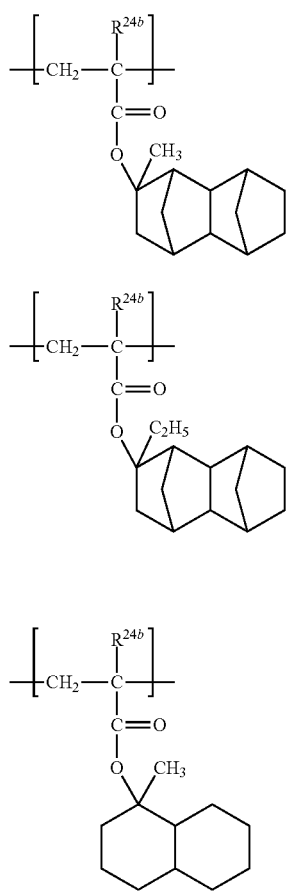
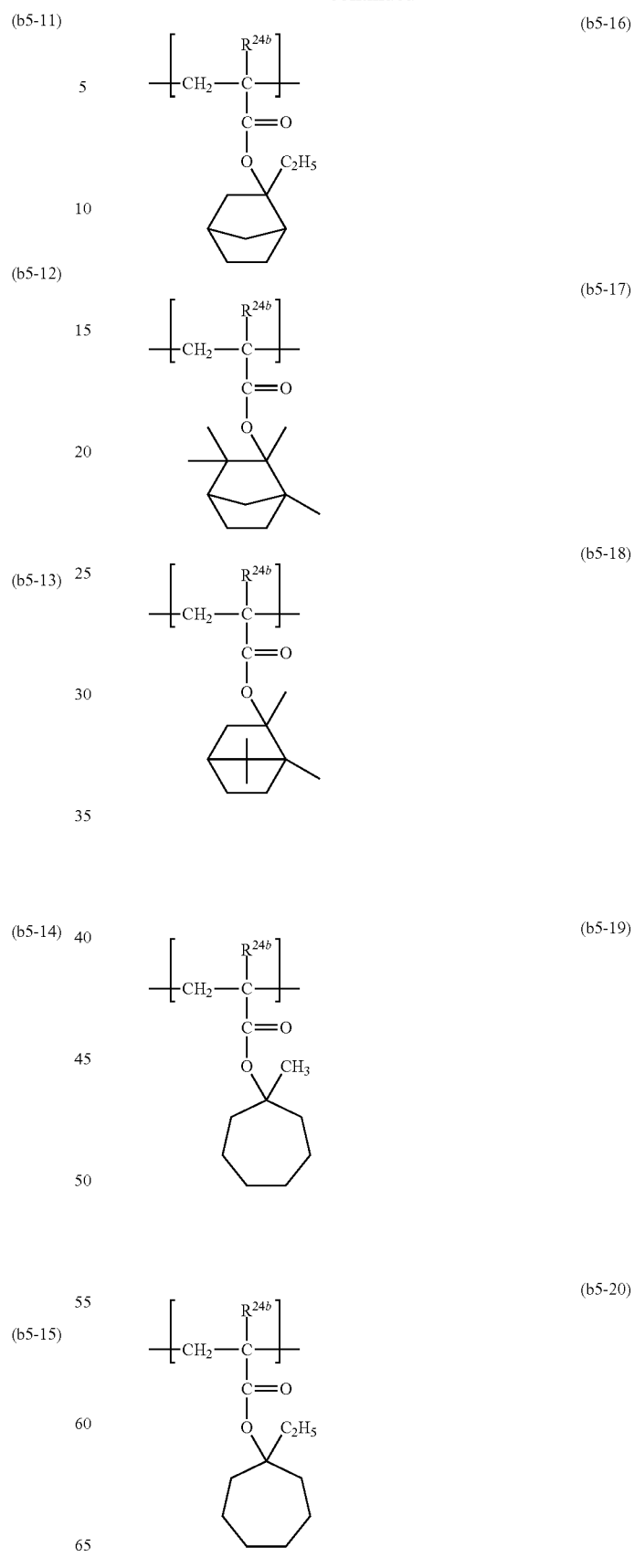

(b5-21) 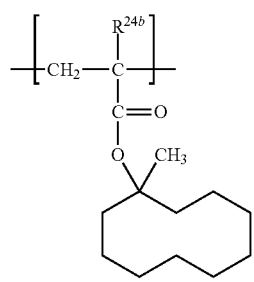
(b5-22) 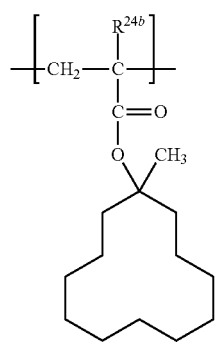
(b5-23) 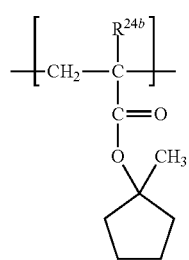
(b5-24) 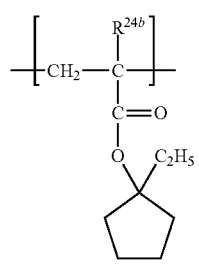
(b5-25) 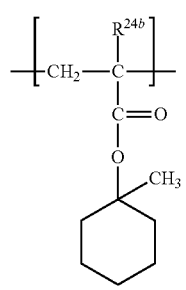
(b5-26) 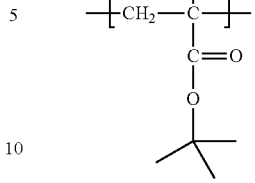
(b5-27) 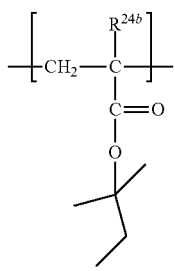
(b5-28) 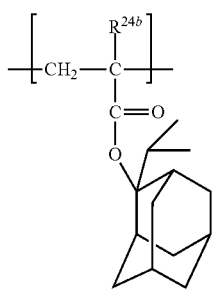
(b5-29) 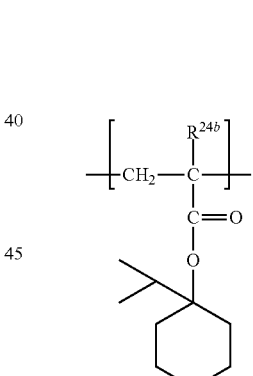
(b5-30) 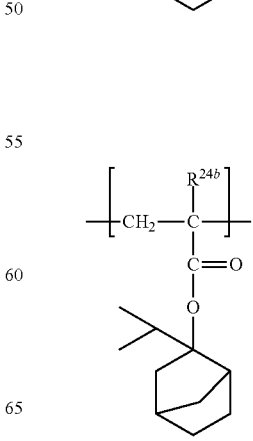

(b5-31)
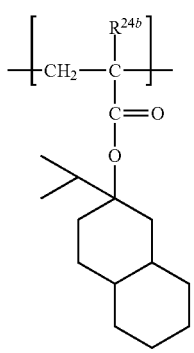
(b5-32)
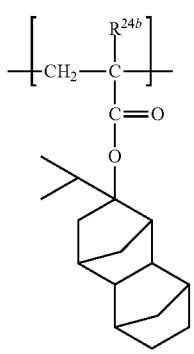
(b5-33)
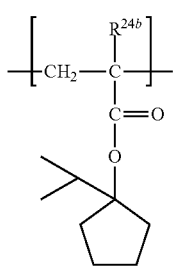
In the above formulae (b5-1) to (b5-33), $R^{24b}$ represents a hydrogen atom or a methyl group.
Preferable specific examples of the constituent unit represented by the above formula (b6) include constituent units represented by the following formulae (b6-1) to (b6-26)
(b6-1)
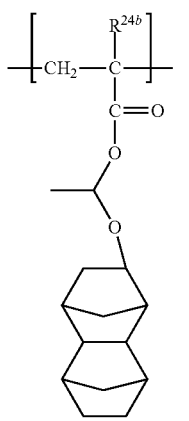
(b6-2)
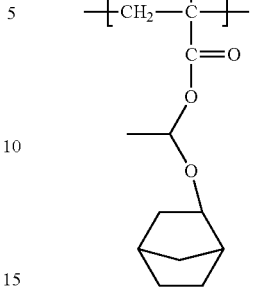
(b6-3)
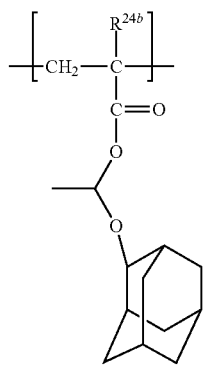
(b6-4)
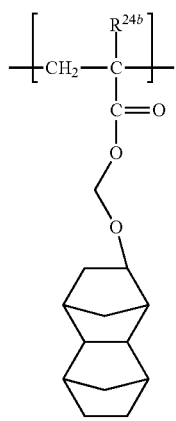
(b6-5)
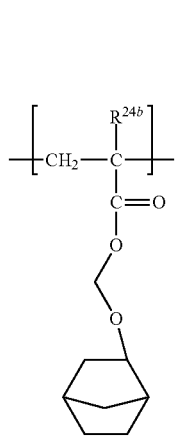

-continued
(b6-6)
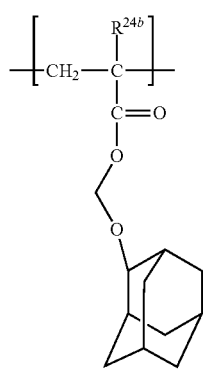
(b6-7)
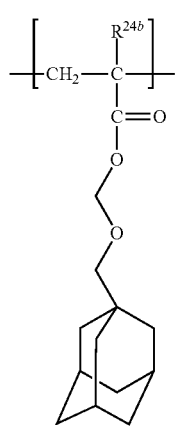
(b6-8)
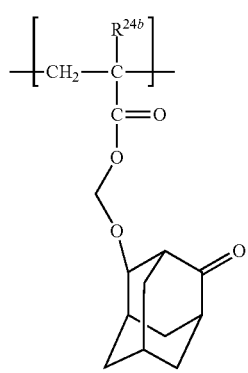
(b6-9)
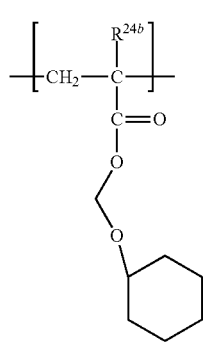
-continued
(b6-10)
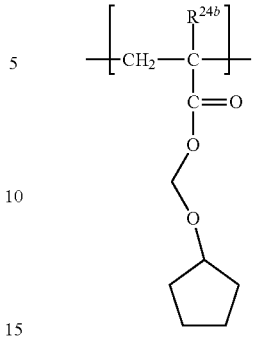
(b6-11)
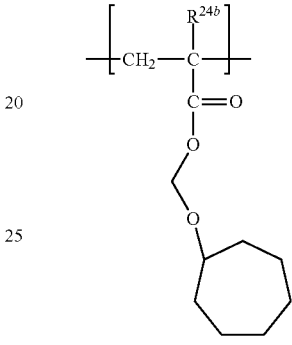
(b6-12)
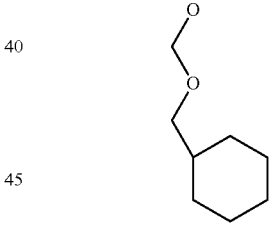
(b6-13)
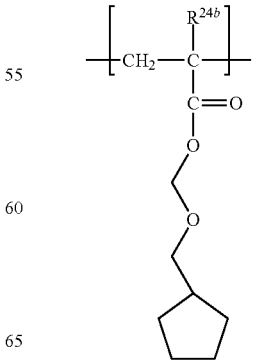

(b6-14)
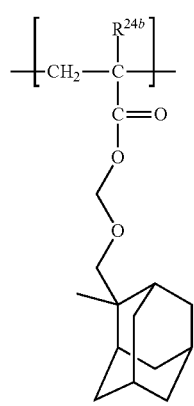
(b6-15)
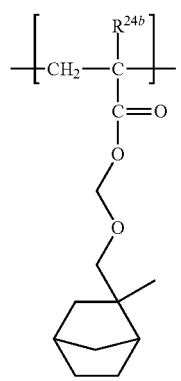
(b6-16)
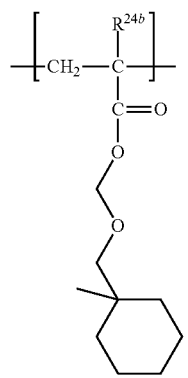
(b6-17)
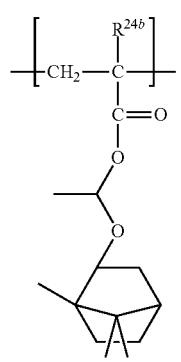
(b6-18)
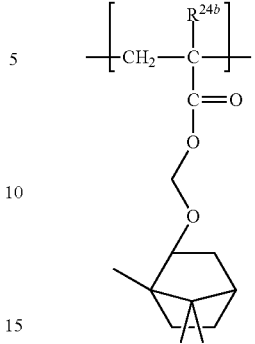
(b6-19)
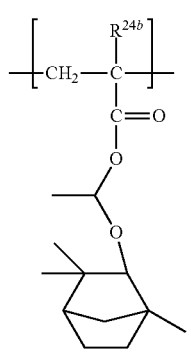
(b6-20)
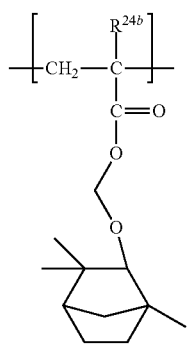
(b6-21)
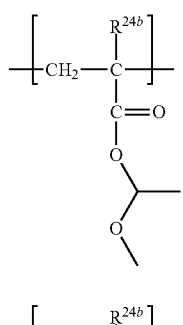
(b6-22)

(b6-23)
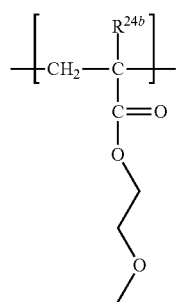
(b6-24)
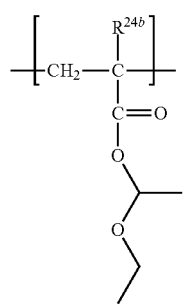
(b6-25)
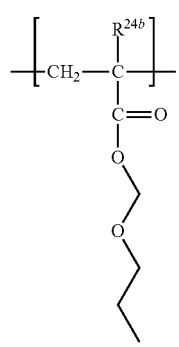
(b6-26)
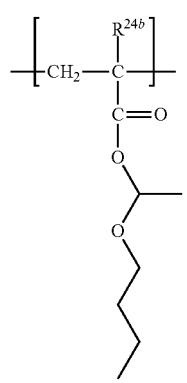
(b7-1)
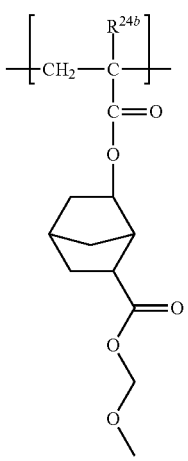
(b7-2)
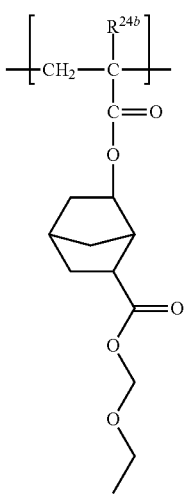
(b7-3)
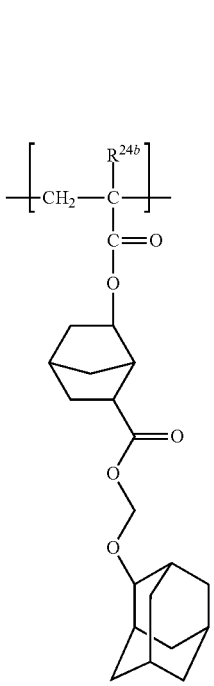
In the above formulae (b6-1) to (b6-26), $R^{24b}$ represents a hydrogen atom or a methyl group.
Preferable specific examples of the constituent unit represented by the above formula (b7) include constituent units represented by the following formulae (b7-1) to (b7-15).

(b7-4)
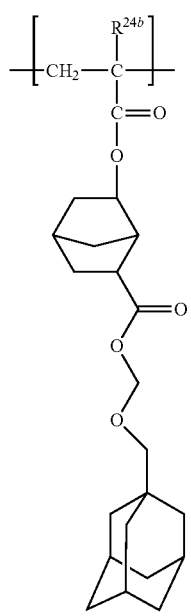
(b7-6)
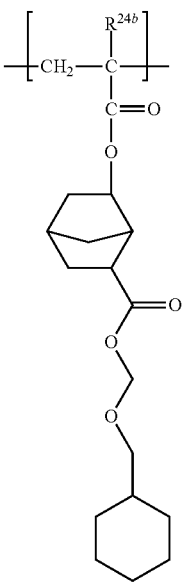
(b7-5)
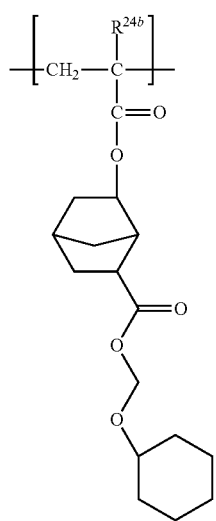
(b7-7)
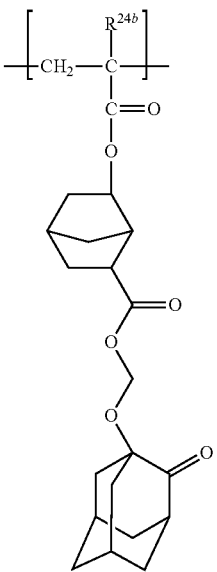

(b7-8)
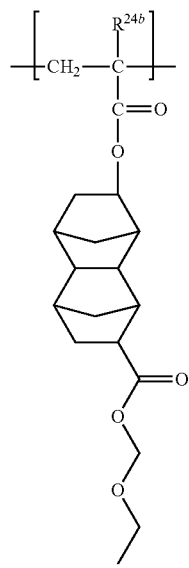
(b7-9)
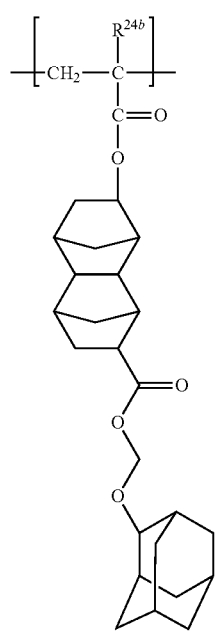
(b7-10)
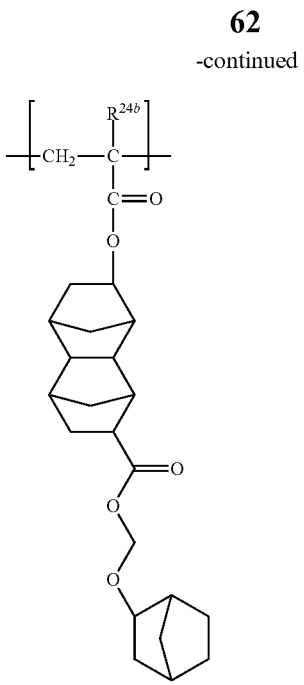
(b7-11)
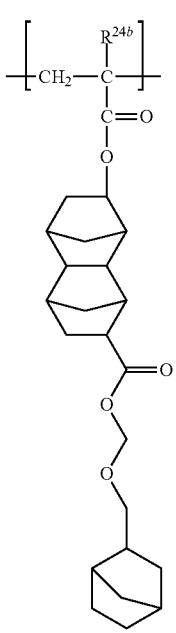

(b7-12)

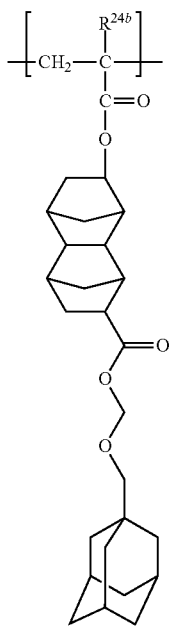

(b7-13)

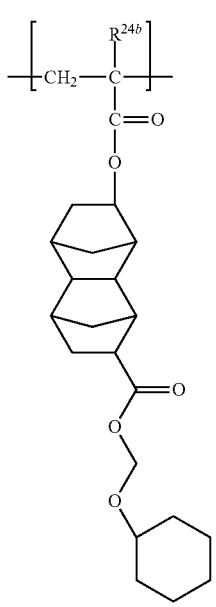

(b7-14)

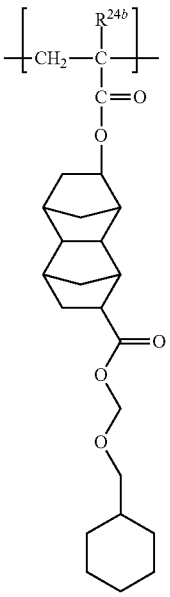

(b7-15)

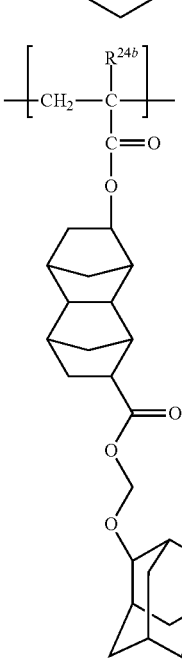

In the above formulae (b7-1) to (b7-15), $R^{24b}$ represents a hydrogen atom or a methyl group.

Among the constituent units represented by the formulae (b5) to (b7) described above, those represented by the formula (b6) are preferred in that they can be easily synthesized and relatively easily sensitized. Further, among the constituent units represented by the formula (b6), those in which $Y^b$ is an alkyl group are preferred, and those in which one or both of $R^{19b}$ and $R^{20b}$ are alkyl groups are preferred.

Further, the acrylic resin (B3) is preferably a resin including a copolymer including a constituent unit derived from a polymerizable compound having an ether bond together with a constituent unit represented by the above formulae (b5) to (b7).

Illustrative examples of the polymerizable compound having an ether bond include radical polymerizable compounds such as (meth)acrylic acid derivatives having an ether bond and an ester bond, and specific examples thereof include 2-methoxyethyl (meth)acrylate, 2-ethoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolyethylene glycol (meth)acrylate, methoxypolypropylene glycol (meth)acrylate, tetrahydrofurfuryl (meth)acrylate, and the like. Also, the above polymerizable compound having an ether bond is preferably, 2-methoxyethyl (meth)acrylate, 2-ethoxyethyl (meth)acrylate, or methoxytriethylene glycol (meth)acrylate. These polymerizable compounds may be used alone, or in combinations of two or more thereof.

Furthermore, the acrylic resin (B3) may include another polymerizable compound as a constituent unit in order to moderately control physical or chemical properties. The polymerizable compound is exemplified by conventional radical polymerizable compounds and anion polymerizable compounds.

Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxyl group and an ester bond such as 2-methacryloyloxyethyl succinic acid, 2-methacryloyloxyethyl maleic acid, 2-methacryloyloxyethyl phthalic acid, and 2-methacryloyloxyethyl hexahydrophthalic acid; (meth)acrylic acid alkyl esters such as methyl(meth)acrylate, ethyl (meth)acrylate, butyl(meth)acrylate and cyclohexyl(meth)acrylate; (meth)acrylic acid hydroxyalkyl esters such as 2-hydroxyethyl (meth)acrylate and 2-hydroxypropyl (meth)acrylate; (meth)acrylic acid aryl esters such as phenyl (meth)acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; amide bond-containing polymerizable compounds such as acrylamide and methacrylamide; and the like.

As described above, the acrylic resin (B3) may include a constituent unit derived from a polymerizable compound having a carboxy group such as the above monocarboxylic acids and dicarboxylic acids. However, it is preferable that the acrylic resin (B3) does not substantially include a constituent unit derived from a polymerizable compound having a carboxyl group, since a resist pattern including a nonresist portion having a favorable rectangular sectional shape can easily be formed. Specifically, the proportion of a constituent unit derived from a polymerizable compound having a carboxyl group in the acrylic resin (B3) is preferably 20% by mass or less, more preferably 15% by mass or less, and particularly preferably 5% by mass or less. In acrylic resin (B3), acrylic resin including a relatively large amount of constituent unit derived from a polymerizable compound having a carboxy group is preferably used in combination with an acrylic resin that includes only a small amount of constituent unit derived from a polymerizable compound having a carboxy group or does not include this constituent unit.

Furthermore, examples of the polymerizable compound include (meth)acrylic acid esters having a non-acid-dissociable aliphatic polycyclic group, and vinyl group-containing aromatic compounds and the like. As the non-acid-dissociable aliphatic polycyclic group, particularly, a tricyclodecanyl group, an adamantyl group, a tetracyclodecanyl group, an isobornyl group, a norbornyl group, and the like are preferred in view of easy industrial availability and the like. These aliphatic polycyclic groups may have a linear or branched alkyl group having 1 or more and 5 or less carbon atoms as a substituent.

Specific examples of the constituent units derived from the (meth)acrylic acid esters having a non-acid-dissociable aliphatic polycyclic group include constituent units having structures represented by the following formulae (b8-1) to (b8-5).

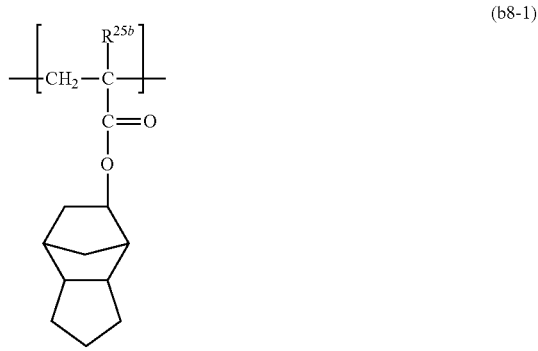

(b8-1)

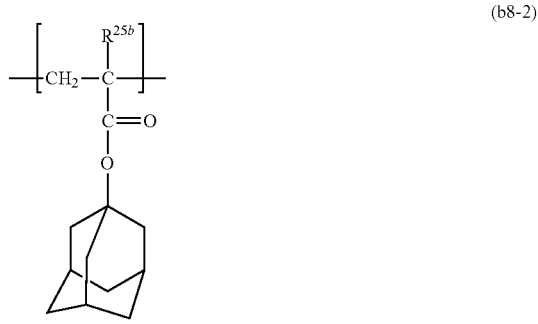

(b8-2)

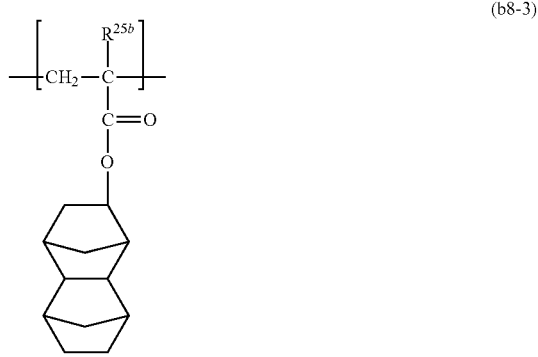

(b8-3)

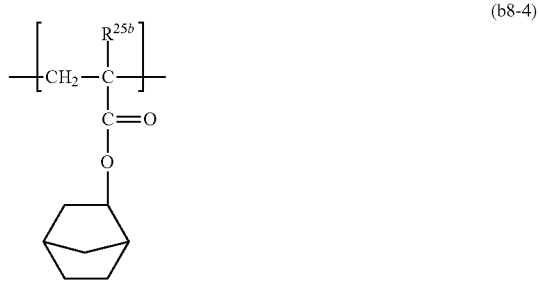

(b8-4)

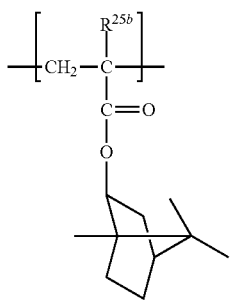

(b8-5)

In formulae (b8-1) to (b8-5), $R^{25b}$ represents a hydrogen atom or a methyl group.

When the acrylic resin (B3) includes the constituent unit (b-3) including a —$SO_2$-containing cyclic group or a lactone-containing cyclic group, the content of the constituent unit (b-3) in the acrylic resin (B3) is preferably 5% by mass or more, more preferably 10% by mass or more, and particularly preferably 10% by mass or more and 50% by mass or less, and most preferably 10% by mass or more and 30% by mass or less. In a case where the photosensitive resin composition includes the constituent unit (b-3) having the above-mentioned range of amount, both good developing property and a good pattern shape can be easily achieved simultaneously.

Further, in the acrylic resin (B3), a constituent unit represented by the aforementioned formulae (b5) to (b7) is preferably included in an amount of 5% by mass or more, more preferably 10% by mass or more, and particularly preferably 10% by mass or more and 50% by mass or less.

The acrylic resin (B3) preferably includes the above constituent unit derived from a polymerizable compound having an ether bond. The content of the constituent unit derived from a polymerizable compound having an ether bond in the acrylic resin (B3) is preferably 0% by mass or more and 50% by mass or less, more preferably 5% by mass or more and 30% by mass or less.

The acrylic resin (B3) preferably includes the above constituent unit derived from (meth)acrylic acid esters having a non-acid-dissociable aliphatic polycyclic group. The content of the constituent unit derived from (meth)acrylic acid esters having a non-acid-dissociable aliphatic polycyclic group in the acrylic resin (B3) is preferably 0% by mass or more and 50% by mass or less, and more preferably 5% by mass or more and 30% by mass or less.

As long as the photosensitive resin composition contains a predetermined amount of the acrylic resin (B3), an acrylic resin other than the acrylic resin (B3) described above can also be used as the resin (B). There is no particular limitation for such an acrylic resin other than the acrylic resin (B3) as long as it includes a constituent unit represented by the aforementioned formulae (b5) to (b7).

The mass-average molecular weight of the resin (B) described above in terms of polystyrene is preferably 10000 or more and 600000 or less, more preferably 20000 or more and 400000 or less, and even more preferably 30000 or more and 300000 or less. A mass-average molecular weight within these ranges allows a photosensitive resin layer to maintain sufficient strength without reducing detachability from a substrate, and can further prevent a swelled profile and crack generation when plating.

It is also preferred that the resin (B) has a dispersivity of 1.05 or more. Dispersivity herein indicates a value of a mass average molecular weight divided by a number average molecular weight. A dispersivity in the range described above can avoid problems with respect to stress resistance on intended plating or possible swelling of metal layers resulting from the plating process.

The content of the resin (B) is preferably 5% by mass or more and 60% by mass or less with respect to the total mass of the photosensitive resin composition. The content of the resin (B) is preferably 5% by mass or more and 98% by mass or less, and more preferably 10% by mass or more and 95% by mass or less, relative to the total solid component of the photosensitive resin composition.

<Mercapto Compound (C)>

The photosensitive resin composition includes a mercapto compound (C) represented by the following formula (C1). Therefore, when a resist pattern is formed using a photosensitive resin composition, the occurrence of footing and the generation of residue after development are suppressed.

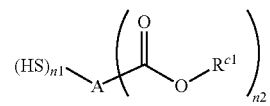

(C1)

In the formula (C1), A is an (n1+n2)-valent linking group including a cyclic group which optionally has one or more substituents and optionally includes one or more heteroatoms, A and a mercapto group are bonded to each other by a C—S bond, A and a group represented by —CO—O—$R^{c1}$ are bonded to each other by a C—C bond, $R^{c1}$s are each independently a hydrogen atom, a hydrocarbon group or an acid dissociable group, n1 is an integer of 1 or more and 4 or less, n2 is 1 or 2, and at least one of $R^{c1}$ is a hydrogen atom or an acid dissociable group, and the hydrocarbon group as $R^{c1}$ is defined as a group that does not correspond to an acid dissociable group.

A is an (n1+n2)-valent linking group and includes a cyclic group which optionally has one or more substituents and optionally includes one or more heteroatoms. There is no particular limitation on the heteroatom that may be included in the cyclic group constituting A as long as the objects of the present invention are not impaired. Suitable examples of the heteroatom include a nitrogen atom, an oxygen atom, a sulfur atom, a phosphorus atom, a boron atom and a silicon atom. Among them, a nitrogen atom, an oxygen atom and a sulfur atom are preferable.

A may be either a group composed only of a cyclic group, or a group composed of a combination of a cyclic group and a noncyclic group. When A is a group composed of a combination of a cyclic group and a noncyclic group, each of the cyclic and noncyclic groups constituting A may be alone, or two or more groups may be used.

The cyclic group included in A may be either a cyclic hydrocarbon group or a heterocyclic group. The cyclic group included in A may be either an aromatic group or an aliphatic cyclic group. If the cyclic group included in A is an aliphatic cyclic group, the aliphatic cyclic group may be either a saturated aliphatic cyclic group or an unsaturated aliphatic cyclic group. If A includes an aliphatic cyclic group, the aliphatic cyclic group is preferably a saturated aliphatic cyclic group.

The structure of the cyclic group included in A may be either a monocyclic structure or a polycyclic structure. Since it is more easily to suppress the generation of residue after development, the structure of the cyclic group included in A is preferably a monocyclic structure. The total number of ring-constituting atoms of one or more cyclic groups included in A is not particularly limited as long as the objects of the present invention are not impaired. Typically, the number of ring-constituting atoms in the ring constituting A may be 3 or more and 50 or less, 4 or more and 30 or less, 5 or more and 20 or less, or 5 or more and 12 or less. For example, when A is a biphenylether-4,4'-diyl group, the total number of ring-constituting atoms of one or more cyclic groups included in A is 12.

When the structure of the cyclic group constituting A is a polycyclic structure, the polycyclic structure may be a polycyclic structure in which two or more monocycles are condensed, a polycyclic structure in which two or more rings are bonded to each other via a single bond or a linking group, a polycyclo ring structure which is a bicyclic ring system, or a tricyclic or higher polycyclic ring system, or a spiro ring structure.

When the structure of the cyclic group constituting A is a polycyclic structure, the polycyclic structure may be composed of two or more aromatic monocycles, may be composed of two or more aliphatic monocycles, or may be composed of one or more aromatic monocycles and one or more aliphatic monocycles. There is no particular limitation on the number of monocycles constituting the polycyclic structure. The number of monocycles constituting the polycyclic structure is preferably, for example, 5 or less, more preferably 3 or less, and particularly preferably 1 or 2. The number of ring-constituting atoms with respect to monocycles constituting the polycyclic structure is preferably 3 or more and 20 or less, more preferably 4 or more and 16 or less, and particularly preferably 5 or more and 12 or less.

When the structure of the cyclic group constituting A is a monocyclic structure, specific examples of the monocyclic structure include monocyclic structures composed of aromatic hydrocarbon rings such as a benzene ring; aliphatic hydrocarbon rings such as a cyclopentane ring, a cyclohexane ring, a cycloheptane ring, a cyclooctane ring, a cyclononane ring, a cyclodecane ring, a cycloundecane ring and a cyclododecane ring; aromatic heterocyclic rings such as a pyrrole ring, a furan ring, a thiophene ring, a pyran ring, a pyridine ring, a pyridazine ring, a pyrimidine ring, a pyrazine ring, a triazine ring, a pyrazole ring, an isoxazole ring, an isothiazole ring, an imidazole ring, an oxazole ring, a thiazole ring, a triazole ring, an oxadiazole ring and a thiadiazole ring; and aliphatic heterocyclic rings such as a pyrrolidine ring, a tetrahydrofuran ring, a tetrahydrothiophene ring, a piperidine ring, a tetrahydropyran ring, a tetrahydrothiopyran ring, a piperazine ring, a morpholine ring and a dioxane ring.

When the structure of the cyclic group constituting A is a polycyclic structure, specific examples of the polycyclic structure include polycyclic structures composed of aromatic hydrocarbon rings such as a naphthalene ring, a biphenyl ring, an anthracene ring and a phenanthrene ring; aliphatic hydrocarbon rings such as a decalin ring, a hydrindane ring, an adamantane ring, a norbornane ring, a norbornene ring, an isobornane ring, a tricyclodecane ring and a tetracyclododecane ring; rings composed of aliphatic hydrocarbon rings and aromatic hydrocarbon rings such as a tetralin ring, an indane ring, a cyclopentylbenzene ring and a cyclohexylbenzene ring; aromatic heterocyclic rings such as an indole ring, an indazole ring, a benzoimidazole ring, a benzoxazole ring, a benzothiazole ring, a quinoline ring, an isoquinoline ring, a cinnoline ring, a phthalazine ring, a quinazoline ring, a quinoxaline ring, a naphthyridine ring, a pteridine ring, a carbazole ring and an acridine ring; aliphatic heterocyclic rings such as a 7-oxanorbornane ring, a 7-thionorbornane ring and a 7-azanorbornane ring; and rings composed of aliphatic heterocyclic rings and aromatic hydrocarbon rings such as an indoline ring and a chroman ring.

The cyclic group included in A may be substituted with any type and any number of substituents as long as the objects of the present invention are not impaired. When the cyclic group included in A has a substituent, the number of substituents vary depending on the number of ring-constituting atoms in the cyclic group included in A, and is preferably 1 or more and 6 or less, more preferably 1 or more and 4 or less, and particularly preferably 1 or 2.

Examples of the substituent include a halogen atom, a hydroxyl group, an alkyl group, an aralkyl group, an alkoxy group, a cycloalkyloxy group, an aryloxy group, an aralkyloxy group, an alkylthio group, a cycloalkylthio group, an arylthio group, an aralkylthio group, an acyl group, an acyloxy group, an acylthio group, an alkoxycarbonyl group, a cycloalkyloxycarbonyl group, an aryloxycarbonyl group, an amino group, an N-monosubstituted amino group, an N,N-disubstituted amino group, a carbamoyl group (—CO—NH$_2$), an N-monosubstituted carbamoyl group, an N,N-disubstituted carbamoyl group, a nitro group and a cyano group.

Specific examples of the halogen atom include a fluorine atom, a chlorine atom, a bromine atom and an iodine atom.

The number of carbon atoms of the alkyl group is not particularly limited, and is preferably 1 or more and 6 or less, and more preferably 1 or more and 3 or less. The alkyl group may be either linear or branched. Specific examples of the alkyl group include a methyl group, an ethyl group, an n-propyl group, an isopropyl group, an n-butyl group, an isobutyl group, a sec-butyl group, a tert-butyl group, an n-pentyl group and an n-hexyl group.

The number of carbon atoms of the aralkyl group is not particularly limited, and is preferably 7 or more and 20 or less, and more preferably 7 or more and 13 or less. Specific examples of the aralkyl group include a benzyl group, a phenethyl group, a naphthalen-1-ylmethyl group and a naphthalen-2-ylmethyl group.

The number of carbon atoms of the alkoxy group is not particularly limited, but the number is preferably 1 or more and 6 or less, and more preferably 1 or more and 3 or less. The alkoxy group may be linear or may be branched. Specific examples of the alkoxy group include a methoxy group, an ethoxy group, an n-propyloxy group, an isopropyloxy group, an n-butyloxy group, an isobutyloxy group, a sec-butyloxy group, a tert-butyloxy group, an n-pentyloxy group, and an n-hexyloxy group.

The number of carbon atoms of the cycloalkyloxy group is not particularly limited, but the number is preferably 3 or more and 10 or less, and more preferably 3 or more and 8 or less. Specific examples of the cycloalkyloxy group include a cyclopropyloxy group, a cyclobutyloxy group, a cyclopentyloxy group, a cyclohexyloxy group, a cycloheptyloxy group, a cyclooctyloxy group, a cyclononyloxy group, and a cyclodecyloxy group.

The number of carbon atoms of the aryloxy group is not particularly limited, but the number is preferably 6 or more and 20 or less, and more preferably 6 or more and 12 or less. Specific examples of the aryloxy group include a phenoxy group, a naphthalene-1-yloxy group, a naphthalene-2-yloxy group, and a biphenylyloxy group.

The number of carbon atoms of the aralkyloxy group is not particularly limited, but the number is preferably 7 or more and 20 or less, and more preferably 7 or more and 13 or less. Specific examples of the aralkyloxy group include a benzyloxy group, a phenethyloxy group, a naphthalene-1-ylmethoxy group, a naphthalene-2-ylmethoxy group, and the like.

The number of carbon atoms of the acyl group is not particularly limited, but the number is preferably 2 or more and 20 or less, and more preferably 2 or more and 11 or less. The acyl group may be an aliphatic acyl group, or may be an aromatic acyl group including an aromatic group. Specific examples of the acyl group include an acetyl group, a propionyl group, a butanoyl group, a pentanoyl group, a hexanoyl group, an octanoyl group, a nonanoyl group, a decanoyl group, a benzoyl group, a naphthalene-1-yl carbonyl group, and a naphthalene-2-yl carbonyl group.

The number of carbon atoms of the acyloxy group is not particularly limited, but the number is preferably 2 or more and 20 or less, and more preferably 2 or more and 11 or less. The acyloxy group may be an aliphatic acyloxy group, or may be an aromatic acyloxy group including an aromatic group. Specific examples of the acyloxy group include an acetyloxy group, a propionyloxy group, a butanoyloxy group, a pentanoyloxy group, a hexanoyloxy group, an octanoyloxy group, a nonanoyloxy group, a decanoyloxy group, a benzoyloxy group, a naphthalene-1-yl carbonyloxy group, and a naphthalene-2-ylcarbonyloxy group.

Suitable examples of an alkylthio group, a cycloalkylthio group, an arylthio group, an aralkylthio group, and an acylthio group include groups in which an oxygen atom is substituted with a sulfur atom in suitable groups as the alkoxy group, cycloalkoxy group, aryloxy group, aralkyloxy group, and acyloxy group.

The number of carbon atoms of the alkoxycarbonyl group is not particularly limited, but the number is preferably 2 or more and 7 or less, and more preferably 2 or more and 4 or less. The alkoxycarbonyl group may be linear or branched. Specific examples of the alkoxycarbonyl group include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, and an n-hexyloxycarbonyl group.

The number of carbon atoms of the cycloalkyloxycarbonyl group is not particularly limited, but the number is preferably 4 or more and 11 or less, and more preferably 4 or more and 9 or less. Specific examples of the cycloalkyloxycarbonyl group include a cyclopropyloxycarbonyl group, a cyclobutyloxycarbonyl group, a cyclopentyloxycarbonyl group, a cyclohexyloxycarbonyl group, a cycloheptyloxycarbonyl group, a cyclooctyloxycarbonyl group, a cyclononyloxycarbonyl group, and a cyclodecyloxycarbonyl group.

The number of carbon atoms of the aryloxycarbonyl group is not particularly limited, but the number is preferably 7 or more and 21 or less, and more preferably 7 or more and 13 or less. Specific examples of the aryloxycarbonyl group include a phenoxycarbonyl group, a naphthalene-1-yloxycarbonyl group, a naphthalene-2-yloxycarbonyl group, and a biphenylyloxycarbonyl group.

In the N-monosubstituted amino group and N,N-disubstituted amino group, the types of substituents bonded to a nitrogen atom are not particularly limited. Suitable examples of the substituents bonded to a nitrogen atom include an alkyl group having 1 or more and 6 or less carbon atoms which may be linear or branched, a cycloalkyl group having 3 or more and 10 or less carbon atoms, an aryl group having 6 or more and 20 or less carbon atoms, an aliphatic acyl group having 2 or more and 7 or less carbon atoms, and an aromatic acyl group having 7 or more and 21 or less carbon atoms. Suitable specific examples of the N-monosubstituted amino group include a methyl amino group, an ethyl amino group, an n-propyl amino group, an isopropyl amino group, an n-butyl amino group, an isobutyl amino group, a sec-butyl amino group, a tert-butyl amino group, an n-pentyl amino group, an n-hexyl amino group, a cyclopropyl amino group, a cyclobutyl amino group, a cyclopentyl amino group, a cyclohexyl amino group, a cycloheptyl amino group, a cyclooctyl amino group, a cyclononyl amino group, a cyclodecyl amino group, a phenyl amino group, a naphthalene-1-yl amino group, a naphthalene-2-yl amino group, a biphenylyl amino group, an acetyl amino group, a propionyl amino group, a butanoyl amino group, a pentanoyl amino group, a hexanoyl amino group, an octanoyl amino group, a nonanoyl amino group, a decanoyl amino group, a benzoyl amino group, a naphthalene-1-yl carbonyl amino group, and a naphthalene-2-yl carbonyl amino group. Suitable examples of the N,N-disubstituted amino group include a dimethyl amino group, a diethyl amino group, a di-n-propyl amino group, a diisopropyl amino group, a di-n-butyl amino group, a diisobutyl amino group, a di-sec-butyl amino group, a di-tert-butyl amino group, a di-n-pentyl amino group, a di-n-hexyl amino group, a dicyclopentyl amino group, a dicyclohexyl amino group, a diphenyl amino group, a diacetyl amino group, a dipropionyl amino group, and a dibenzoyl amino group.

In the N-monosubstituted carbamoyl group and N,N-disubstituted carbamoyl group, the types of substituents bonded to a nitrogen atom are not particularly limited. Suitable examples of the substituents bonded to a nitrogen atom are the same as those descried as to the N-monosubstituted amino group and N,N-disubstituted amino group. Suitable specific examples of the N-monosubstituted amino carbamoyl group include an N-methyl carbamoyl group, an N-ethyl carbamoyl group, an N-n-propylcarbamoyl group, an N-isopropyl carbamoyl group, an N-n-butylcarbamoyl group, an N-isobutylcarbamoyl group, an N-sec-butylcarbamoyl group, an N-tert-butylcarbamoyl group, an N-n-pentyl carbamoyl group, an N-n-hexylcarbamoyl group, an N-cyclopropylcarbamoyl group, an N-cyclobutylcarbamoyl group, an N-cyclopentyl carbamoyl group, an N-cyclohexylcarbamoyl group, an N-cycloheptylcarbamoyl group, an N-cyclooctylcarbamoyl group, an N-cyclononylcarbamoyl group, an N-cyclodecylcarbamoyl group, an N-phenylcarbamoyl group, an N-naphthalene-1-ylcarbamoyl group, an N-naphthalene-2-ylcarbamoyl group, an N-biphenylylcarbamoyl group, an N-acetylcarbamoyl group, an N-propionylcarbamoyl group, an N-butanoylcarbamoyl group, an N-pentanoylcarbamoyl group, an N-hexanoylcarbamoyl group, an N-octanoylcarbamoyl group, an N-nonanoylcarbamoyl group, an N-decanoylcarbamoyl group, an N-benzoyl carbamoyl group, an N-naphthalene-1-yl carbonyl carbamoyl group, and an N-naphthalene-2-yl carbonyl carbamoyl group. Suitable examples of the N,N-disubstituted carbamoyl group include an N,N-dimethyl carbamoyl group, an N,N-diethyl carbamoyl group, an N,N-di-n-propylcarbamoyl group, an N,N-di isopropyl carbamoyl group, an N,N-di-n-butylcarbamoyl group, an N,N-diisobutylcarbamoyl group, an N,N-di-sec-butylcarbamoyl group, an N,N-di-tert-butylcarbamoyl group, an N,N-di-n-pentyl carbamoyl group, an N,N-di-n-hexyl carbamoyl group, an N,N-dicyclopentyl carbamoyl group, an N,N-dicyclohexyl carbamoyl group, an N,N-diphenylcarbamoyl group, an N,N-diacetylcarbamoyl group, an N,N-dipropionylcarbamoyl group, and an N,N-dibenzoyl carbamoyl group.

When A in the formula (C1) includes a noncyclic group, a valence of the noncyclic group is not particularly limited. The valence of the noncyclic group included in A is preferably 2 or more and 4 or less, more preferably 2 or 3, and particularly preferably 2. Preferred examples of the divalent noncyclic group include an alkylene group, an alkenylene group, an alkynylene group, —O—, —CO—, —S—, —CS—, —NH—, —N=N—, —SO— and —SO$_2$—, and those in which two or more groups selected from these groups are used in combination. In the formula (C1), A and a mercapto group are bonded to each other by a C—S bond, and A and a group represented by —CO—O—R$^{c1}$ are bonded to each other by a C—C bond.

When the noncyclic group included in A is an alkylene group, an alkenylene group or an alkynylene group, the number of carbon atoms of these groups is preferably 2 or more and 10 or less, more preferably 2 or more and 6 or less, still more preferably 2 or more and 4 or less, and particularly preferably 2.

In the formula (C1), n1 is an integer of 1 or more and 4 or less, and n2 is 1 or 2. Since it is easy to prepare and obtain a mercapto compound (C), n1 is preferably 1 or 2, and more preferably 1. Therefore, A in the formula (C1) is preferably a divalent or trivalent group.

Suitable examples of the case where A in the formula (C1) is a divalent or trivalent group include groups included in the following Group A.

(Group A)

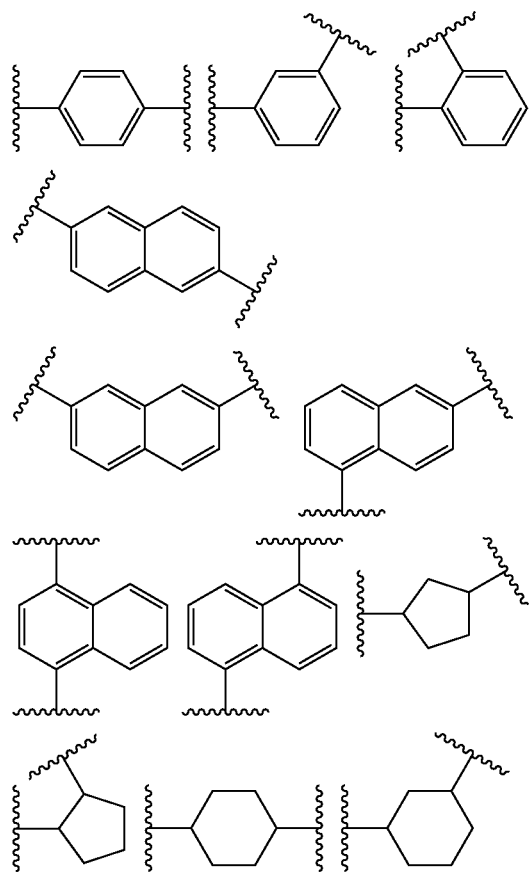

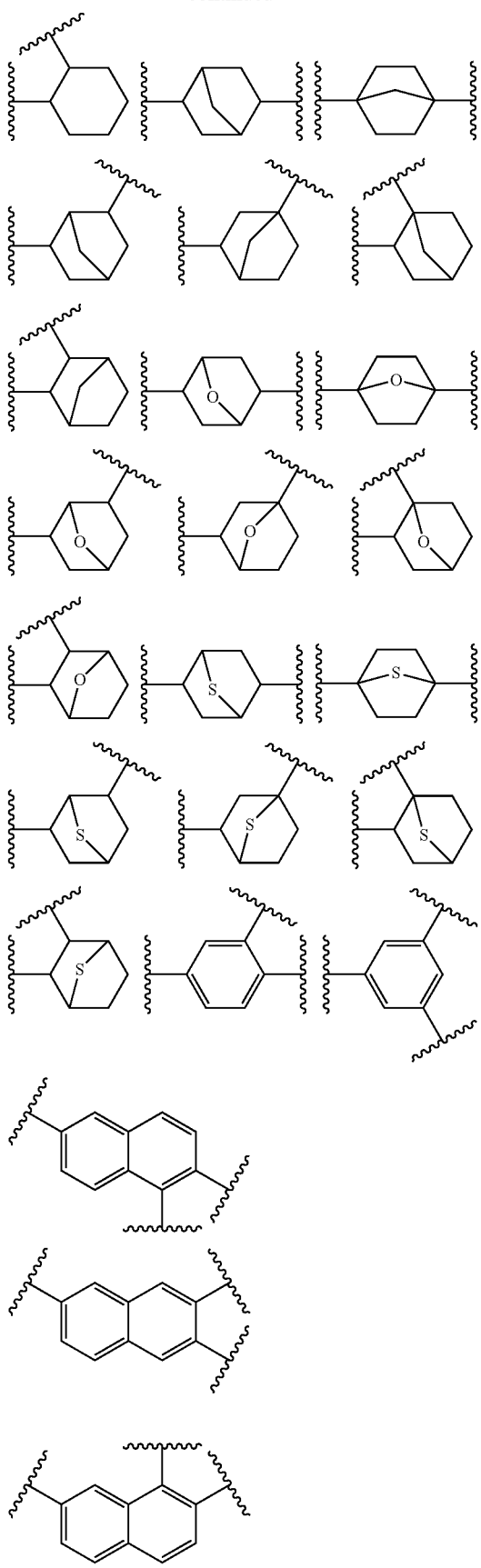

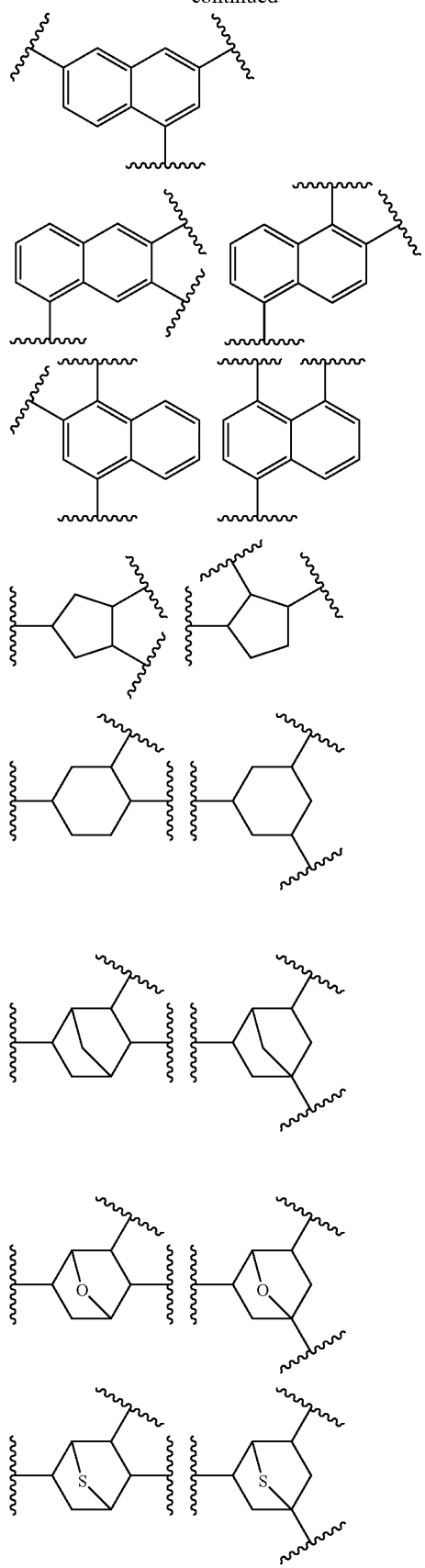
Groups included in the following Group B are also preferred as A in the formula (C1).
(Group B)
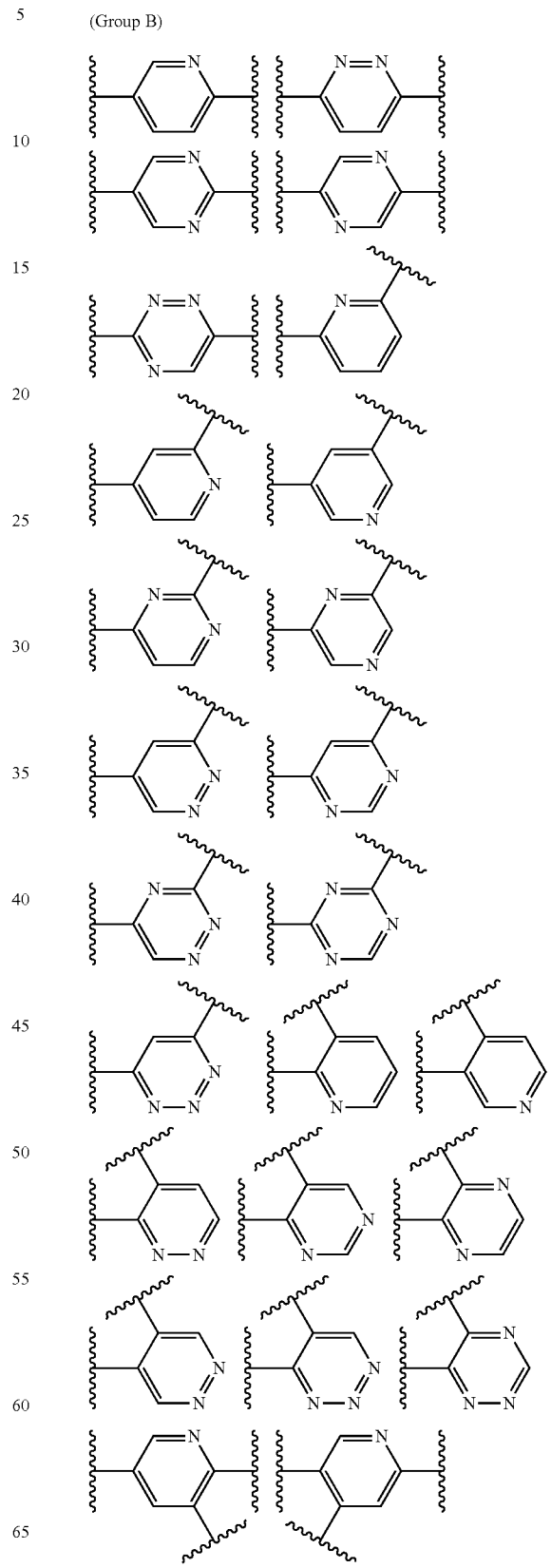

-continued

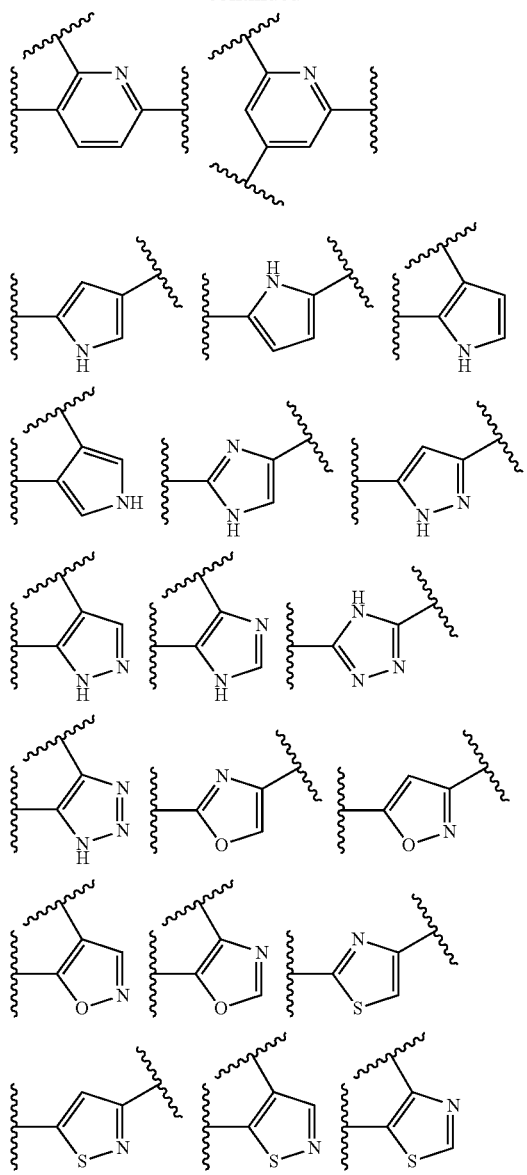

Groups included in the following Group C are also preferred as A in the formula (C1). Regarding the following groups, the mercapto group is preferably bonded to the atomic bonding which is bonded to a heterocyclic group.

(Group C)

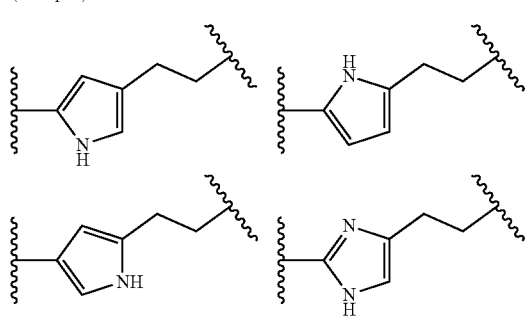

-continued

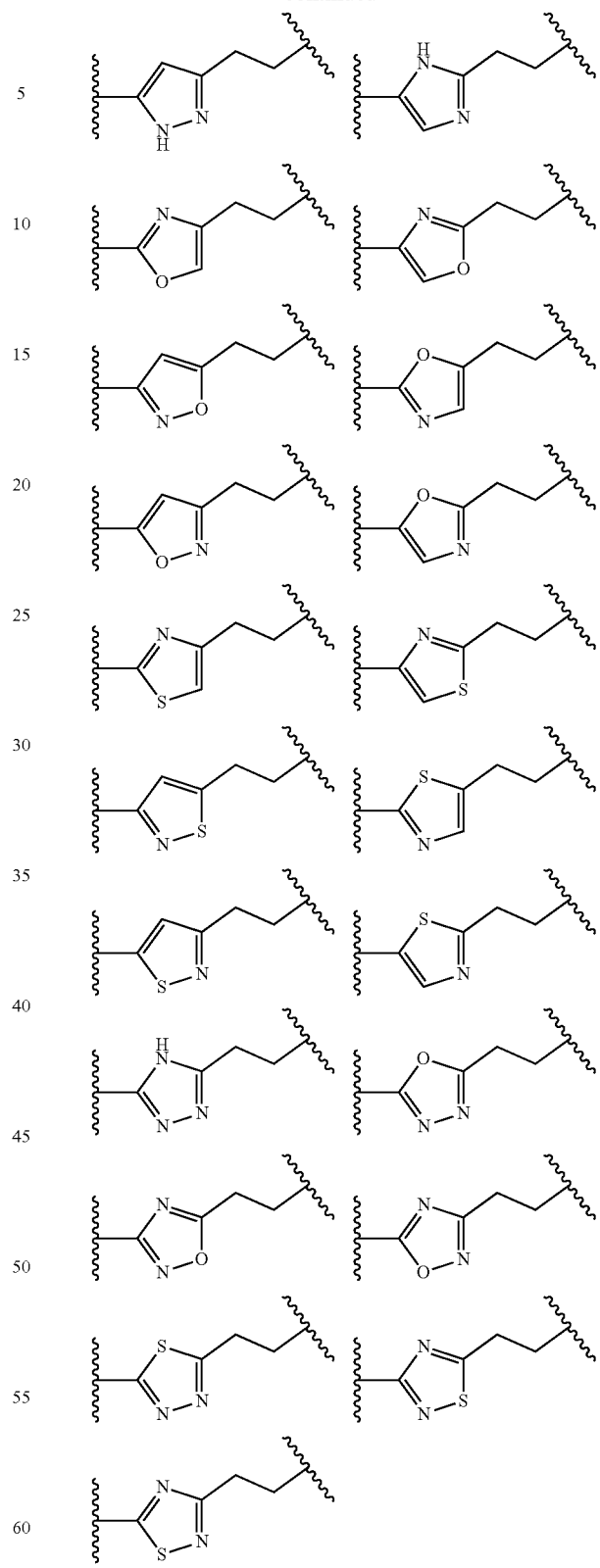

Groups included in the following Group D are also preferred as A in the formula (C1). Regarding the following groups, the mercapto group is preferably bonded to the atomic bonding which is bonded to a heterocyclic group.

(Group D)
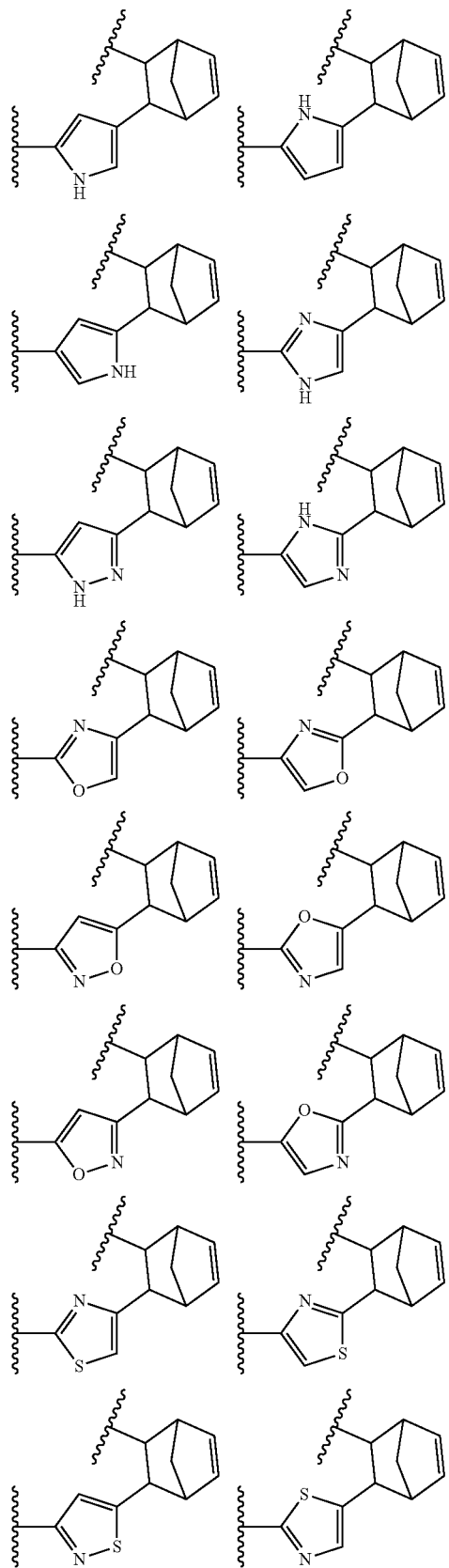
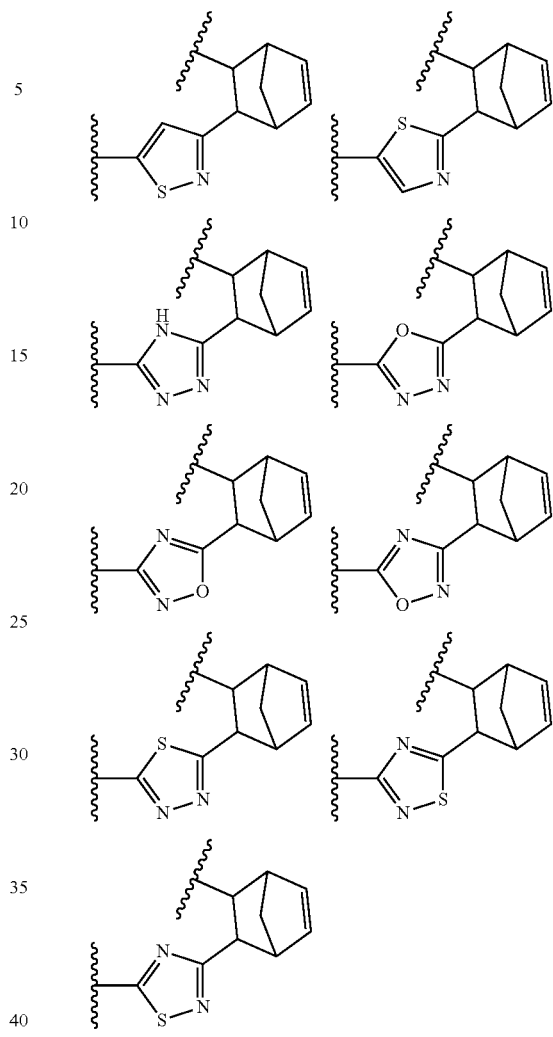
Groups included in the following Group E are also preferred as A in the formula (C1). Regarding the following groups, the mercapto group is preferably bonded to the atomic bonding which is bonded to a heterocyclic group.
(Group E)
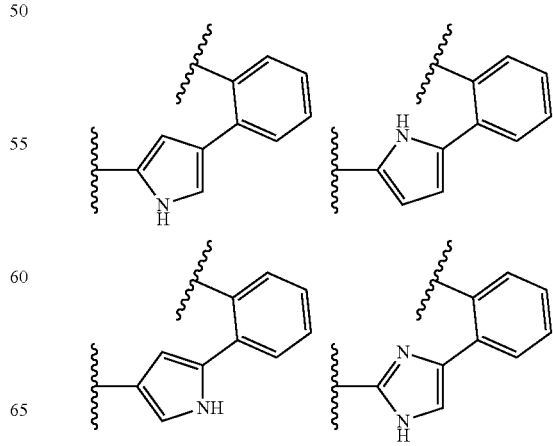

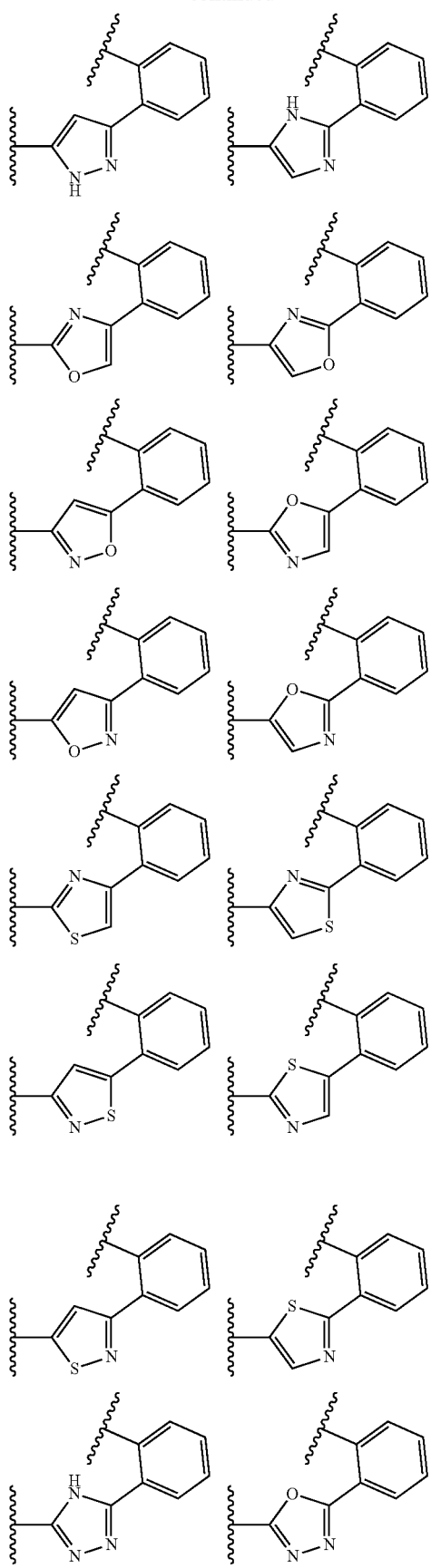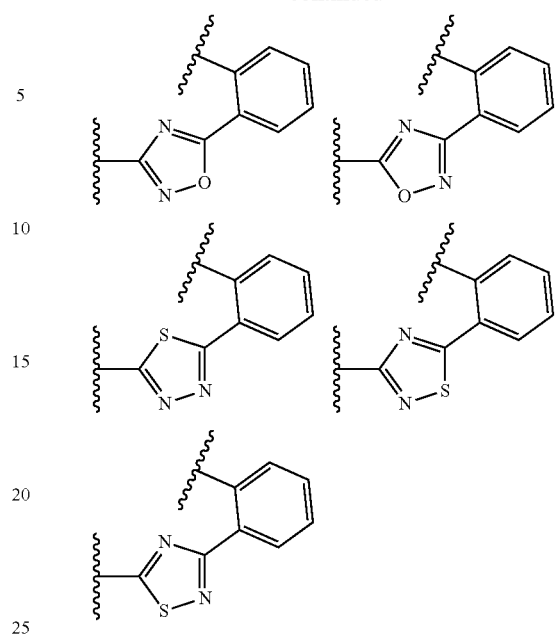
Groups included in the following Group F are also preferred as A in the formula (C1). Regarding the following groups, the mercapto group is preferably bonded to the atomic bonding which is bonded to a heterocyclic group.
(Group F)
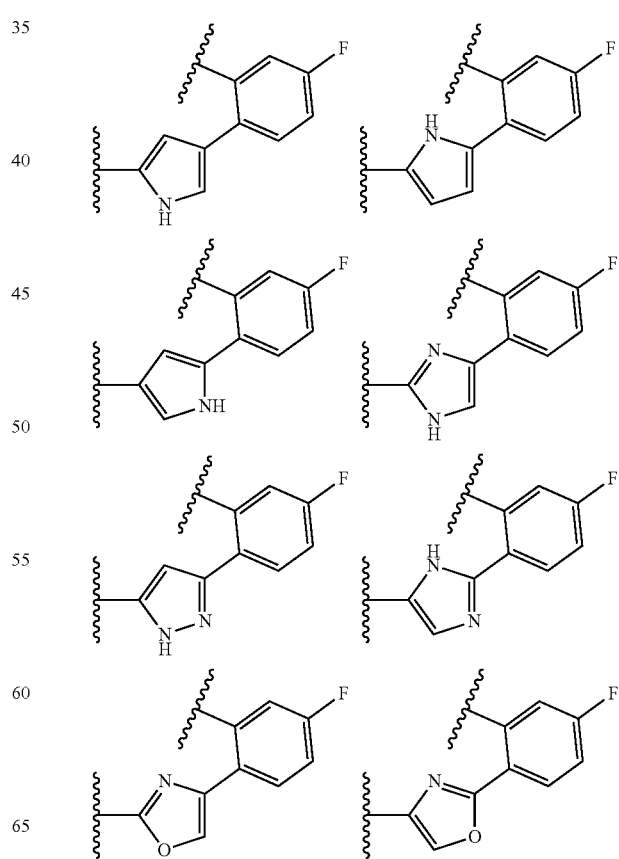

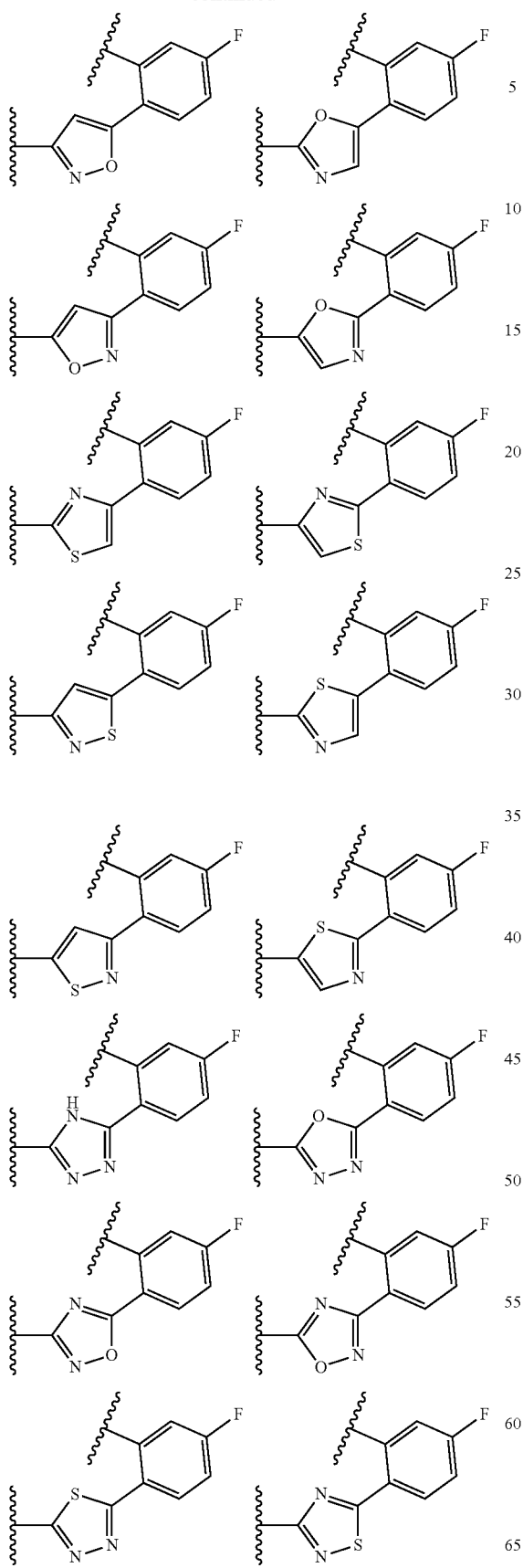
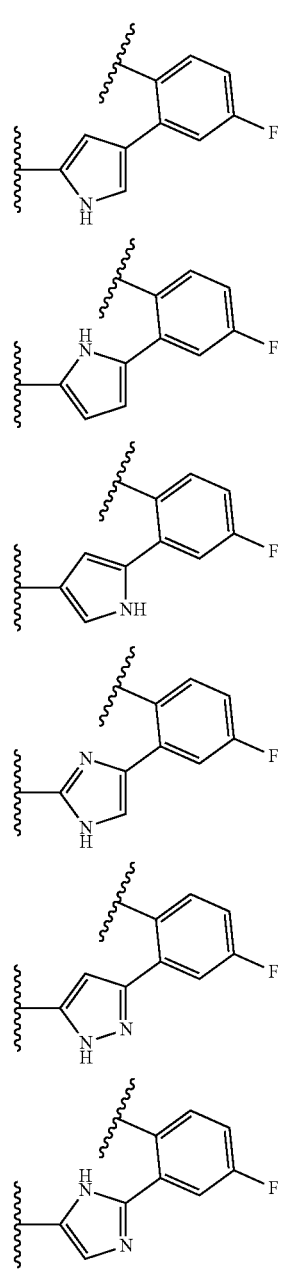
Groups included in the following Group G are also preferred as A in the formula (C1). Regarding the following groups, the mercapto group is preferably bonded to the atomic bonding which is bonded to a heterocyclic group.
(Group G)

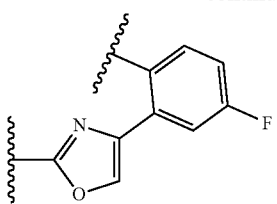
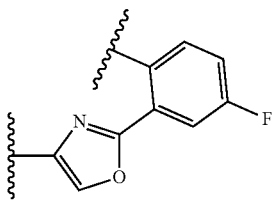
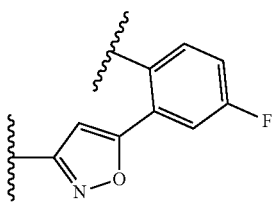
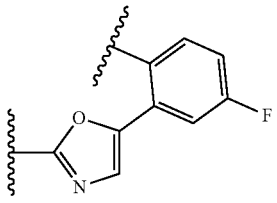
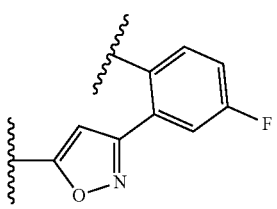
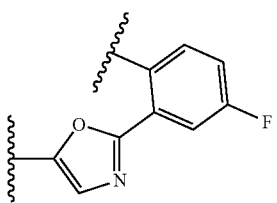
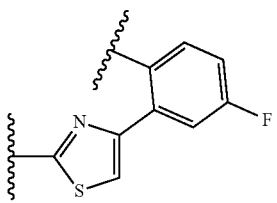
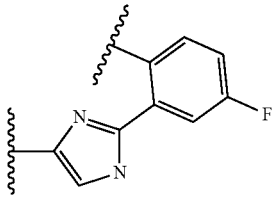
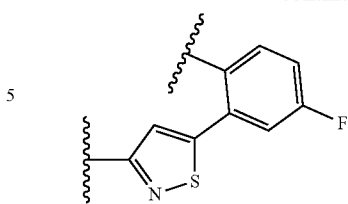
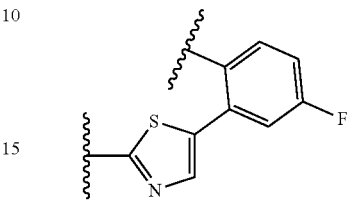
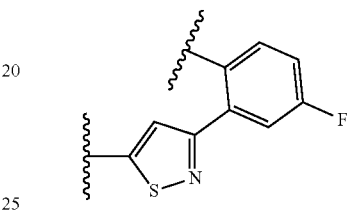
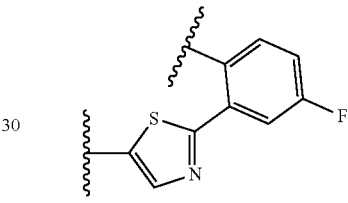
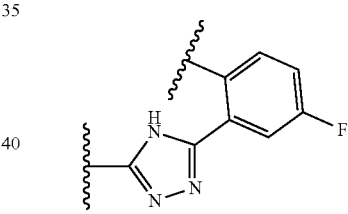
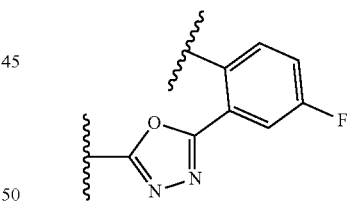
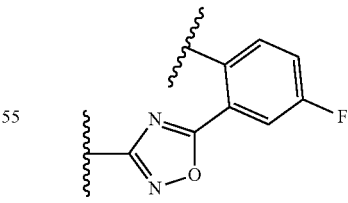
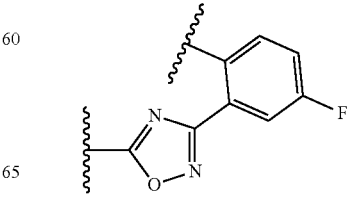

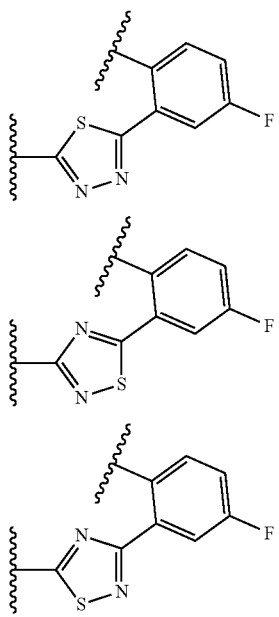
Groups included in the following Group H are also preferred as A in the formula (C1). Regarding the following groups, the mercapto group is preferably bonded to the atomic bonding which is bonded to a heterocyclic group.
(Group H)
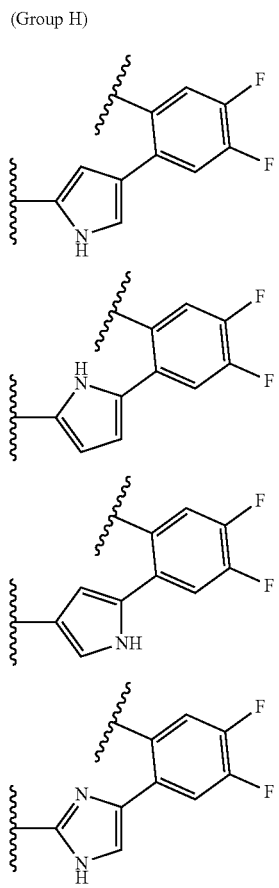
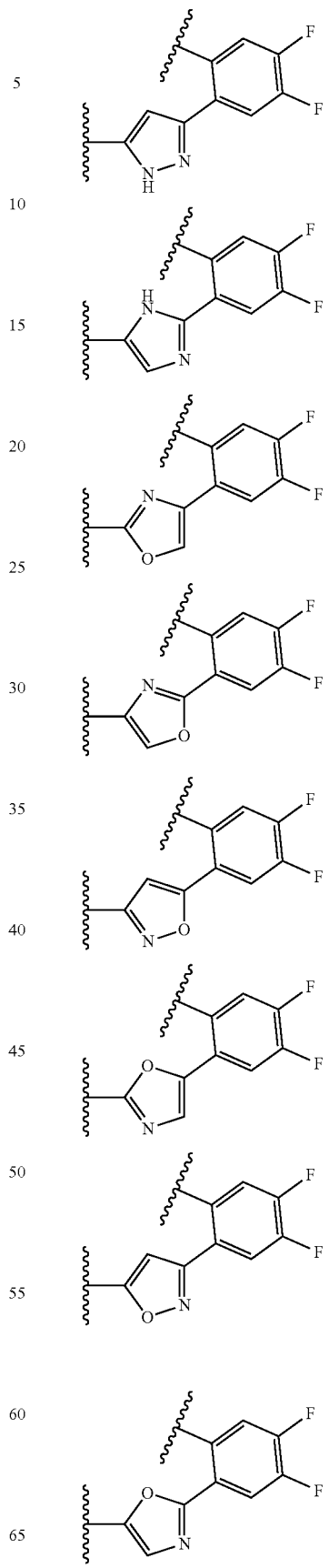

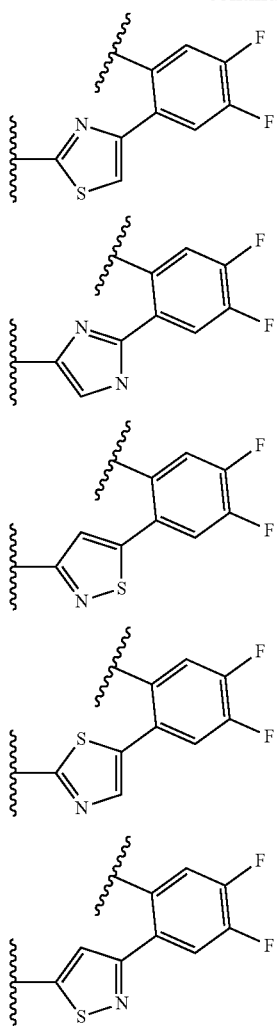
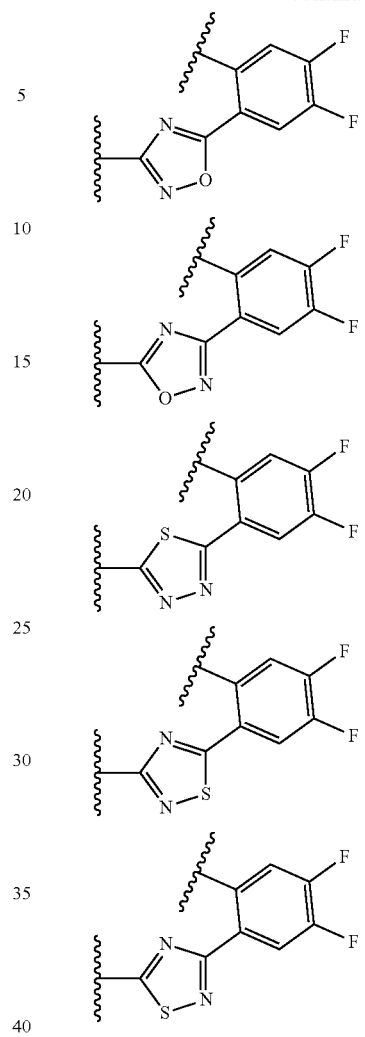
Groups included in the following Group I are also preferred as A in the formula (C1). Regarding the following groups, the mercapto group is preferably bonded to the atomic bonding which is bonded to a heterocyclic group.
(Group I)
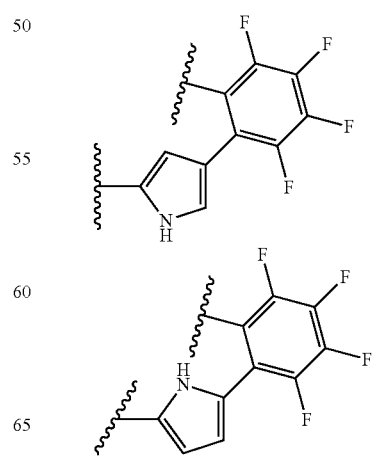
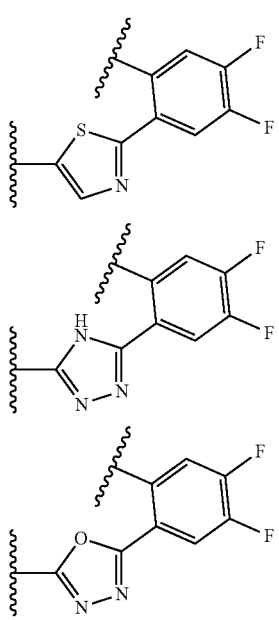

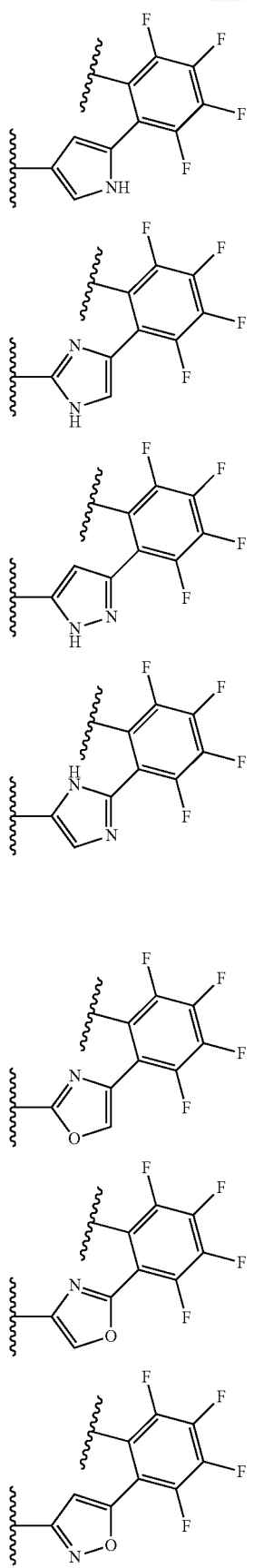
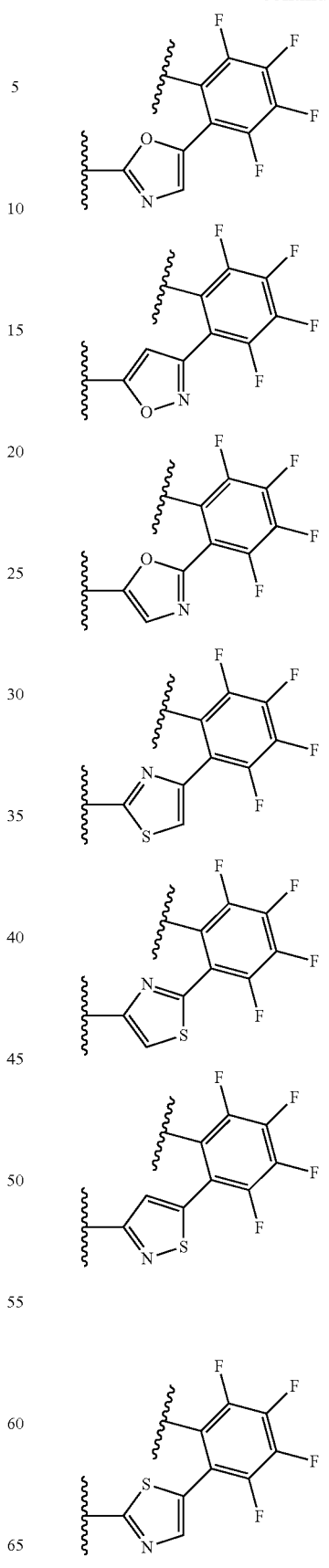

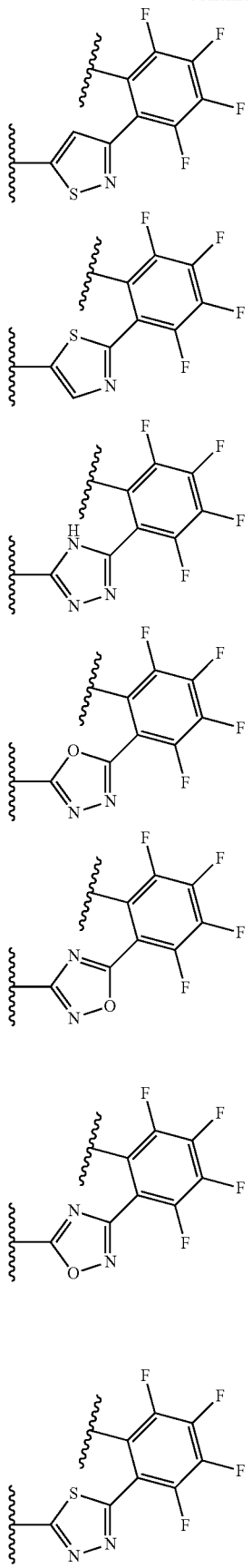

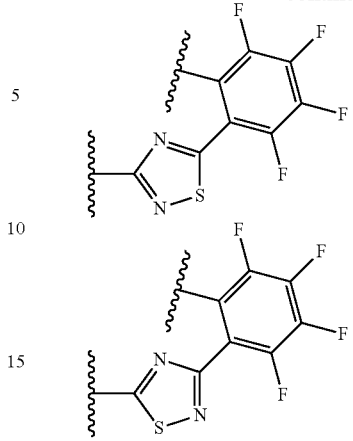

In the formula (C1), $R^{c1}$ each independently represent a hydrogen atom, a hydrocarbon group or an acid dissociable group. In the formula (C1), when n2 is 2, two $R^{c1}$s may be the same or different. At least one of $R^{c1}$s is a hydrogen atom or an acid dissociable group. Therefore, when the coated film is formed using a photosensitive resin composition including an acid generator (A) and a mercapto compound (C) and the coated film is exposed, in an exposed section of the coated film, the mercapto compound (C) exists as a compound having at least one carboxy group. This is because: when $R^{c1}$ is a hydrogen atom, the mercapto compound (C) has a carboxy group, and when $R^{c1}$ is an acid dissociable group, a group represented by —$COOR^{c1}$ is converted into a carboxy group by an acid generated from the acid generator (A).

As a result, when development with an alkali developing solution is performed after exposing the coated film formed using the photosensitive resin composition, a mercapto compound having a carboxy group, which is the mercapto compound (C) itself or derived from the mercapto compound (C), satisfactorily dissolves in the alkali developing solution. For such a reason, when using a photosensitive resin composition including the mercapto compound (C) represented by the above formula (C1), residue is not easily generated after development.

When patterning is performed using a positive-type photosensitive resin composition including an acid generator (A) which generates acid upon exposure to an irradiated active ray or radiation, and a resin (B) whose solubility in alkali increases under the action of acid, it is considered that the acid generated from the acid generator (A) during exposure is deactivated in the vicinity of the surface of the substrate. In particular, in the vicinity of the interface between an exposed portion and unexposed portion, in which the acid concentration is low, footing easily occurs due to the influence of deactivation of the acid on the surface of the substrate. In this respect, when the photosensitive resin composition includes a mercapto compound, deactivation of the acid on the surface of the substrate is easily suppressed, thus easily suppressing footing.

The mercapto compound (C) has a mercapto group and a polar group represented by —$COOR^{c1}$ in the molecule. Therefore, in the vicinity of interface between the substrate surface and the coated film, the mercapto compound (C) is easily oriented such that the mercapto group is positioned at a substrate surface side and a polar group represented by —$COOR^{c1}$ is positioned at a side opposite to a substrate in the coated film. This is because the resin (B) and the like included in the photosensitive resin composition usually has high polarity to some extent. In the formula (C1), when n2 is 2, two polar groups represented by —COOR$^{c1}$ are preferably bonded to each other at adjacent positions on the ring (ring-constituting atoms) in A including a cyclic group. When two polar groups represented by —COOR$^{c1}$ exist at these positions, the mercapto compound (C) is easily oriented in a more preferred state.

For the above-mentioned reasons, it is considered that use of a photosensitive resin composition including a mercapto compound (C) having the above predetermined structure remarkably suppresses the occurrence of footing.

In the formula (C1), when R$^{c1}$ is a hydrocarbon group, R$^{c1}$ is preferably a hydrocarbon group having 1 or more and 20 or less carbon atoms, more preferably a saturated aliphatic hydrocarbon group having 1 or more and 20 or less carbon atoms or an aromatic hydrocarbon group having 6 or more 20 or less carbon atoms, still more preferably a saturated aliphatic hydrocarbon group having 1 or more and 20 or less carbon atoms, particularly preferably a saturated aliphatic hydrocarbon group having 1 or more and 10 or less carbon atoms, and most preferably a saturated aliphatic hydrocarbon group having 1 or more and 6 or less carbon atoms. When R$^{c1}$ is a saturated aliphatic hydrocarbon group, the saturated aliphatic hydrocarbon group may be preferably either linear or branched, and linear is preferable.

When R$^{c1}$ is an aromatic hydrocarbon group, suitable specific examples of the aromatic hydrocarbon group include a phenyl group, a naphthalen-1-yl group, a naphthalen-2-yl group, a 4-phenylphenyl group, a 3-phenylphenyl group and a 2-phenylphenyl group. Among them, a phenyl group is preferred.

When R$^{c1}$ is a saturated aliphatic hydrocarbon group, a saturated aliphatic hydrocarbon group is preferably an alkyl group since it is easy to synthesize and obtain the compound represented by the formula (C1). Suitable specific examples of the alkyl group for R$^{c1}$ include a methyl group, an ethyl group, an n-propyl group, an isopropyl group, an n-butyl group, an isobutyl group, a sec-butyl group, an n-pentyl group, an n-hexyl group, an n-heptyl group, an n-octyl group, an n-nonyl group and an n-decyl group. Among them, a methyl group, an ethyl group, an n-propyl group and an isopropyl group are preferred, and a methyl group and an ethyl group are more preferred.

In the formula (C1), when R$^{c1}$ is an acid dissociable group, the acid dissociable group may be a group which is the same as the acid-dissociable dissolution-inhibiting group described about the resin (B). Suitable examples of the acid dissociable group as R$^{c1}$ include groups of the following formula.

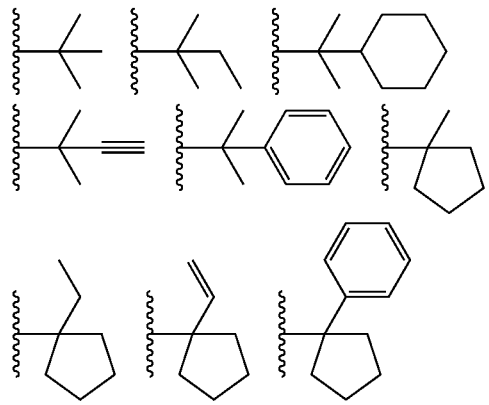

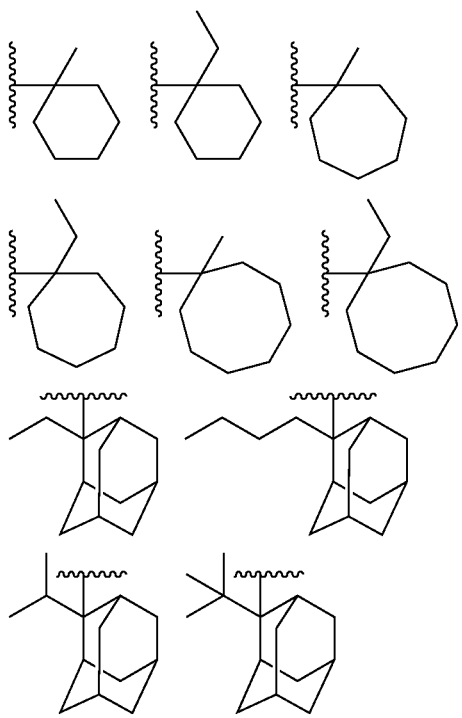

Since it is easy to suppress the occurrence of footing and the generation of residue after development, the mercapto compound (C) is preferably a compound represented by the following formula (C1-1).

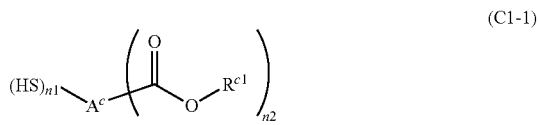

(In the formula (C1-1), R$^{c1}$, n1 and n2 are the same as those in the formula (C1), and A$^c$ is an (n1+n2)-valent aliphatic cyclic group which optionally has one or more substituents and optionally includes one or more heteroatoms.)

In the formula (C1-1), it is preferred that A$^c$ and a mercapto group are bonded to each other by a C—S bond, and A$^c$ and a group represented by —CO—O—R$^{c1}$ are bonded to each other by a C—C bond.

The mercapto compound represented by the above formula (C1-1) has, as A$^c$, an aliphatic cyclic group. Due to this fact, the mercapto compound represented by the formula (C1-1) tends to have low log P value. With respect to the mercapto compound represented by the formula (C1-1), it is assumed that low log P value is involved in the fact that the occurrence of footing is easily suppressed, satisfactorily.

As mentioned above, A in the formula (C1) is preferably a divalent or trivalent group. Therefore, A$^c$ in the formula (C1-1) is also preferably a divalent or trivalent group. The following groups are preferred as the aliphatic cyclic group as Ac.

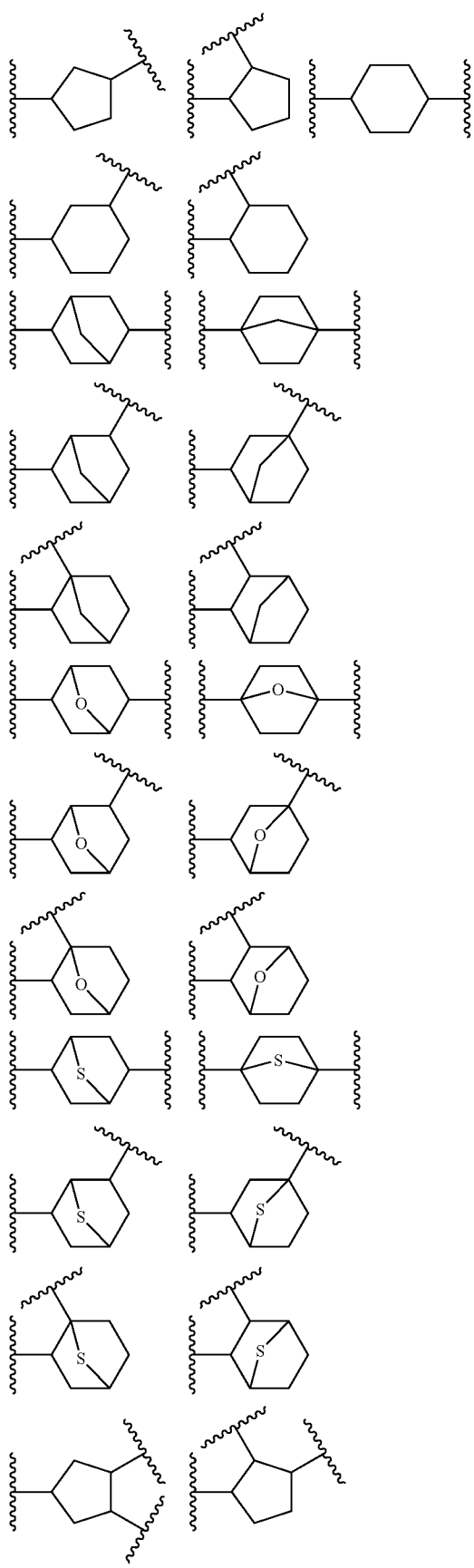

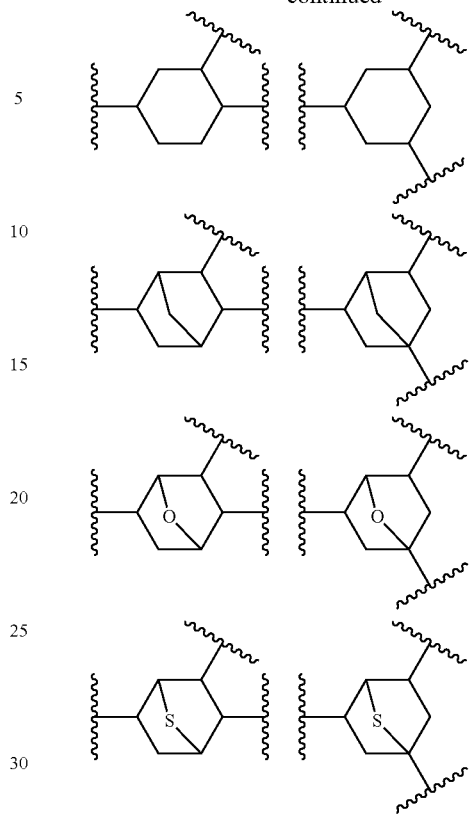

Furthermore, the mercapto compound (C) is more preferably a compound represented by the following formula (C1-2).

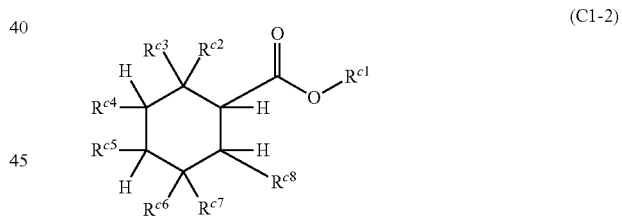

(C1-2)

(In the formula (C1-2), $R^{c1}$ is the same as that in formula (C1), $R^{c2}$, and $R^{c6}$ are each independently a hydrogen atom or an alkyl group, or $R^{c2}$ and $R^{c6}$ may be bonded to each other to form a divalent group selected from the group consisting of —O—, —S—, —CH$_2$— and —C(CH$_3$)$_2$—, $R^{c3}$, $R^{c4}$, $R^{c5}$ and $R^{c7}$ are each independently a hydrogen atom or a mercapto group, $R^{c8}$ is a hydrogen atom or a group represented by —CO—O—$R^{c9}$, $R^{c9}$ is a hydrogen atom, a hydrocarbon group or an acid dissociable group, at least one of $R^{c1}$ and $R^{c9}$ is a hydrogen atom or an acid dissociable group, and at least one of $R^{c3}$, $R^{c4}$, $R^{c5}$ and $R^{c7}$ is a mercapto group.)

In the formula (C1-2), $R^{c9}$ is the same as Rd.

Suitable specific examples of the mercapto compound (C), which is the mercapto compound represented by the formula (C1) described above, include the following compounds.

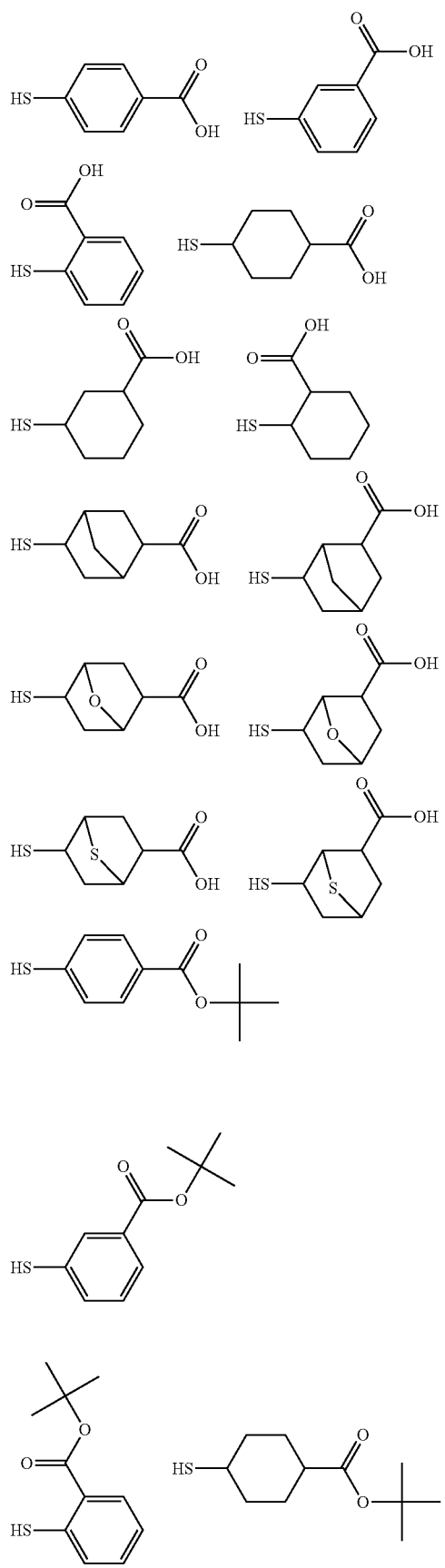
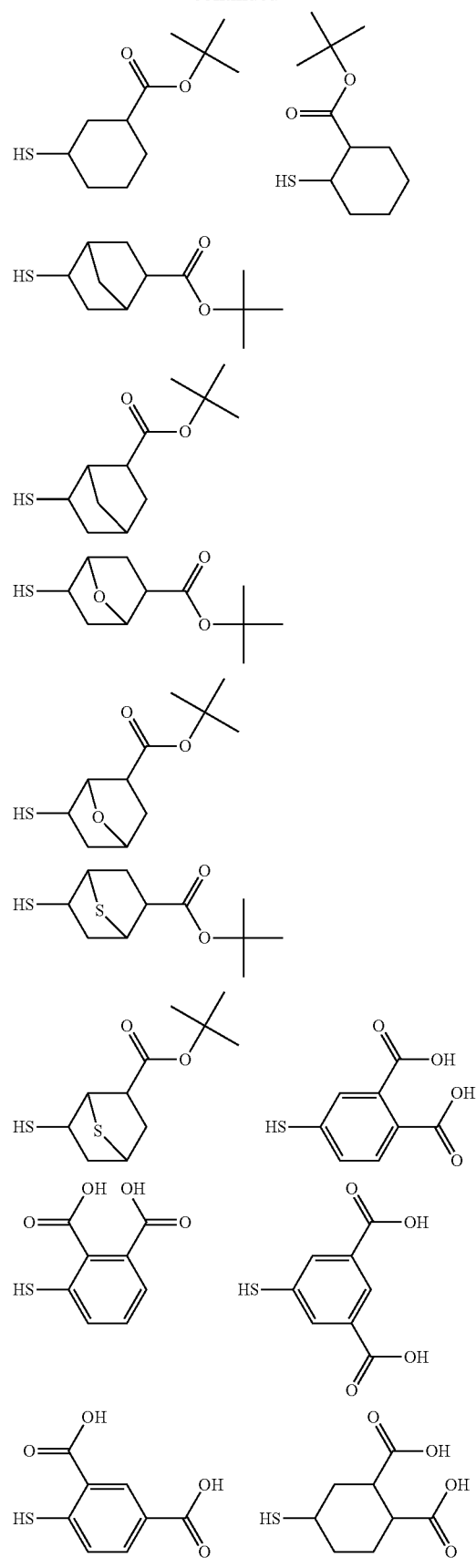

101
-continued
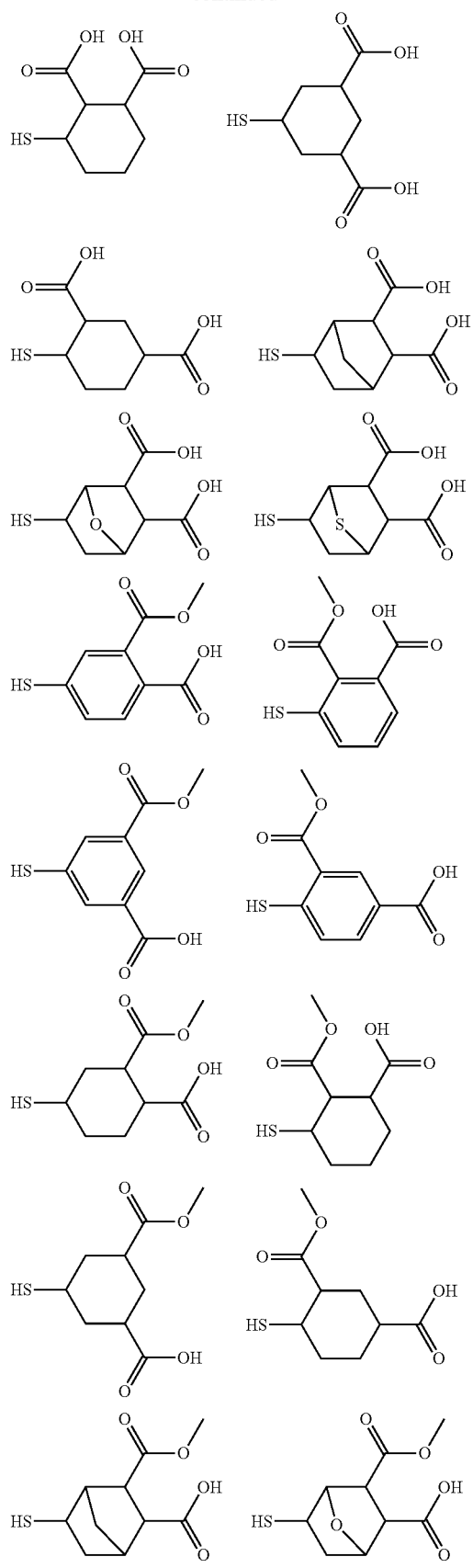
102
-continued
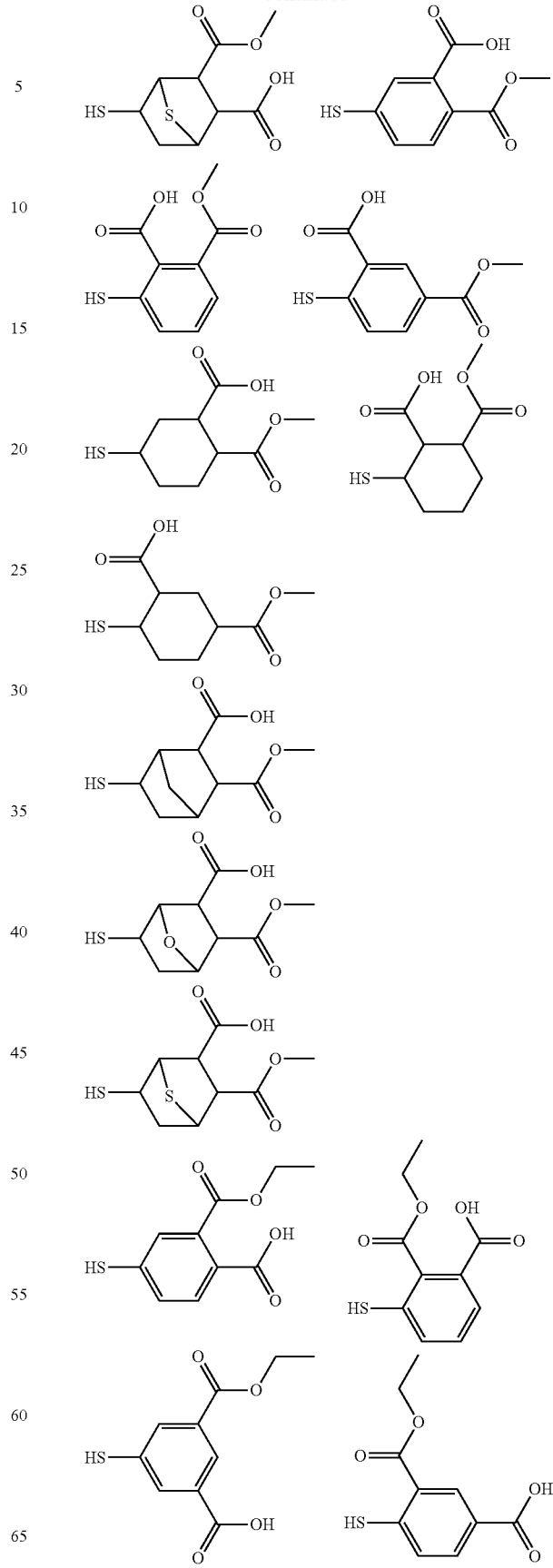

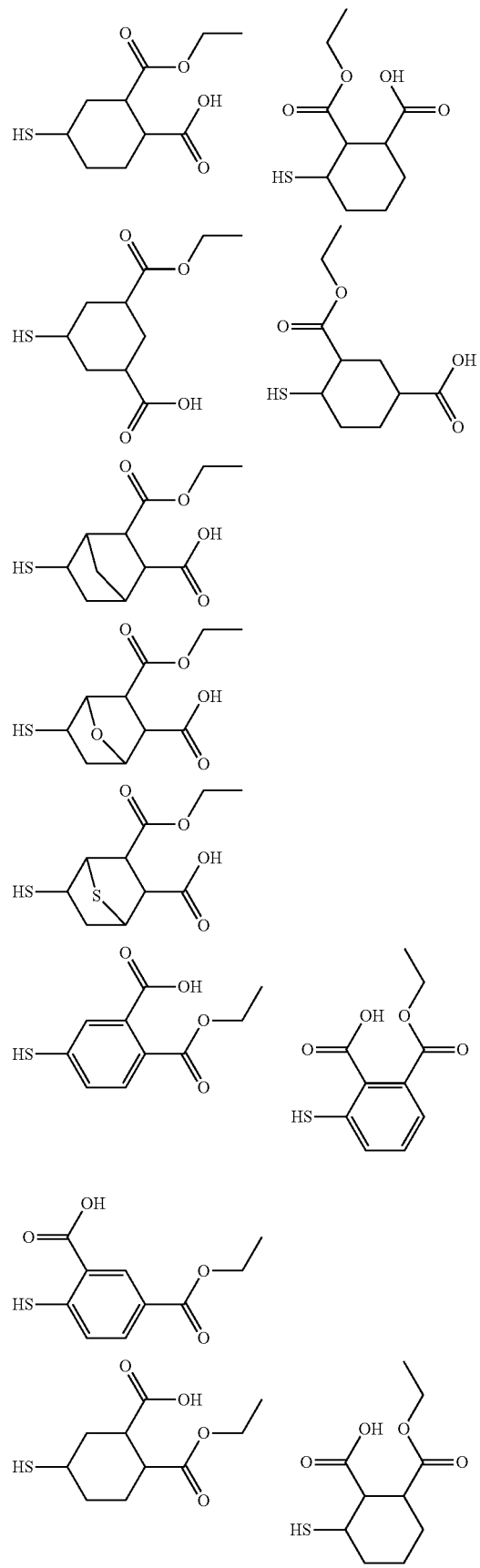
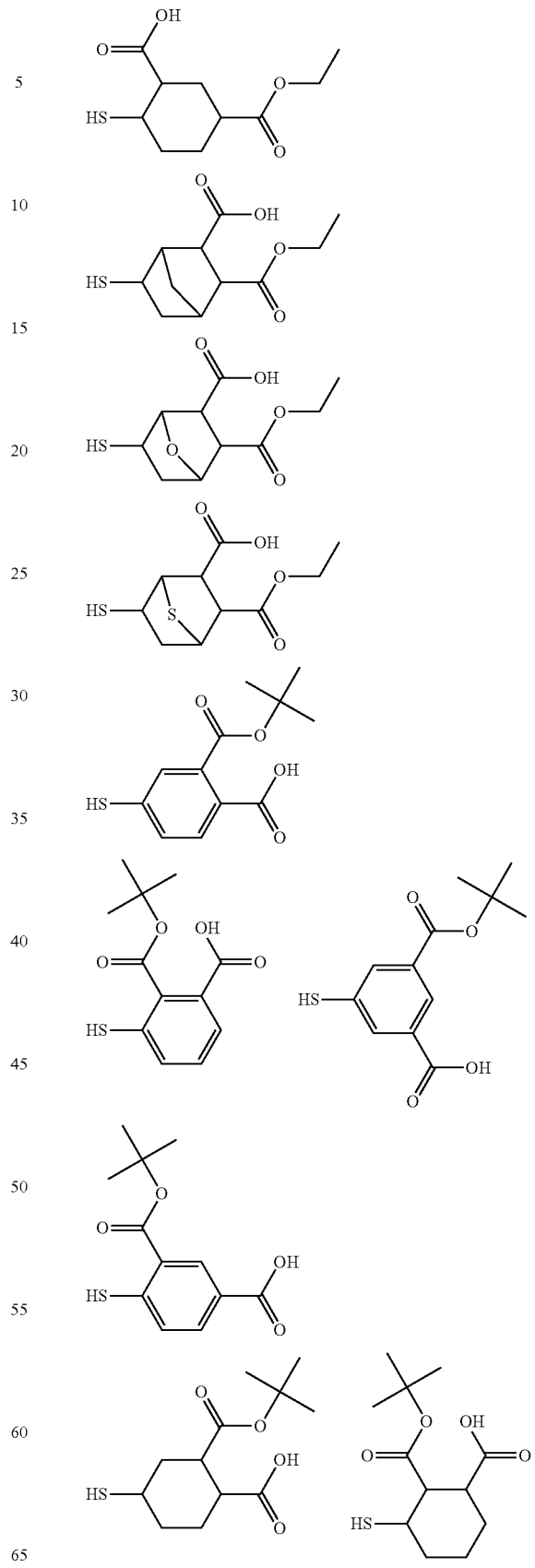

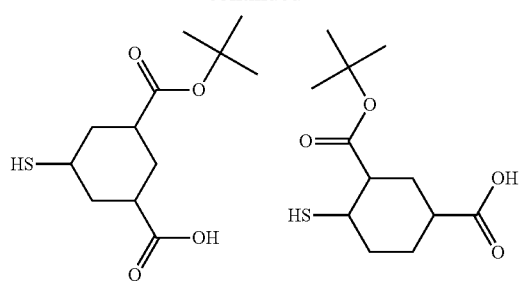
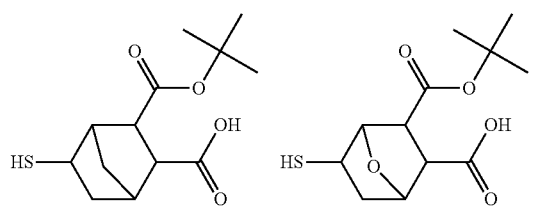
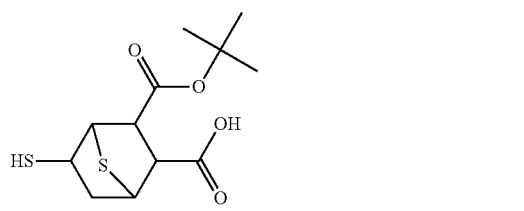
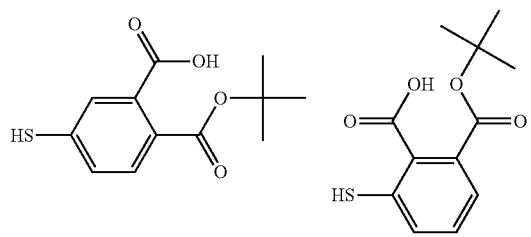
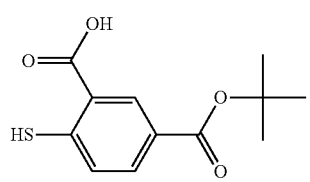
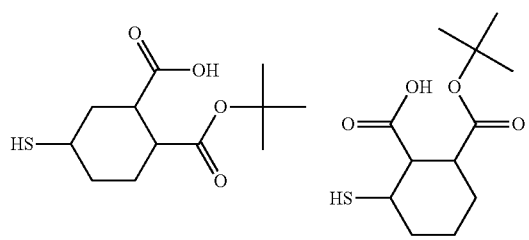
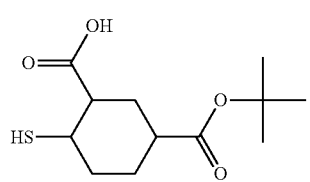
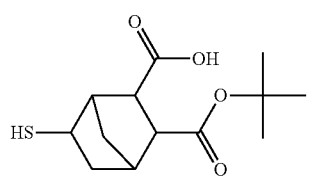
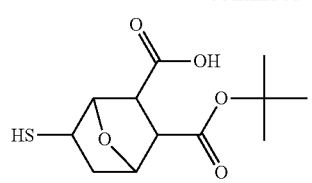
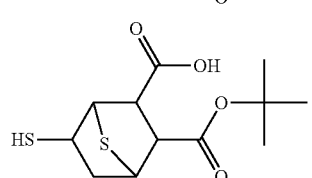
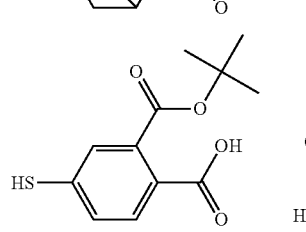
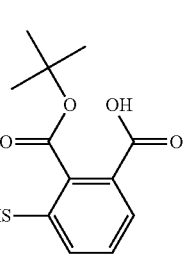
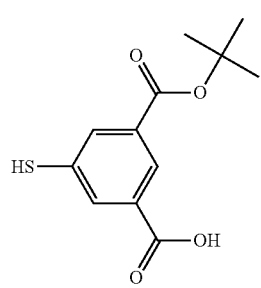
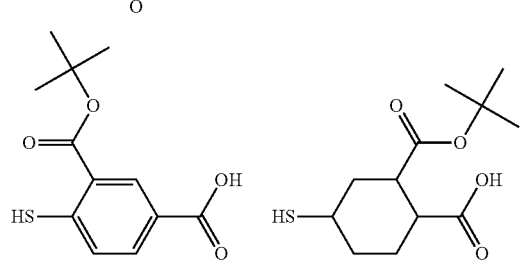
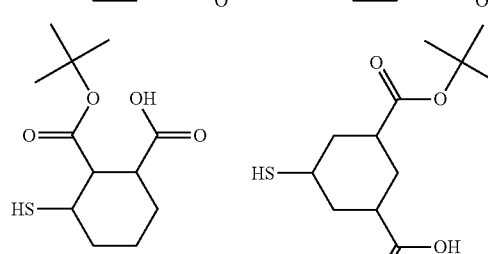
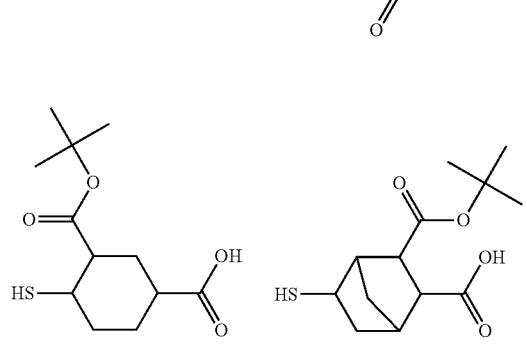

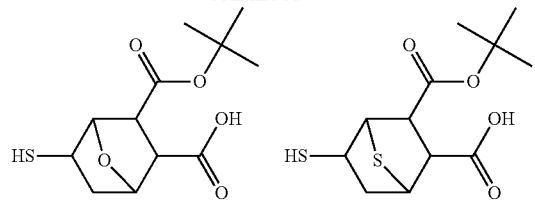
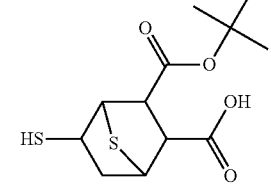
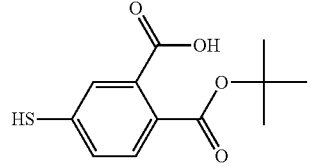
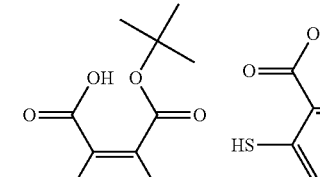
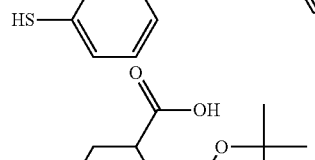
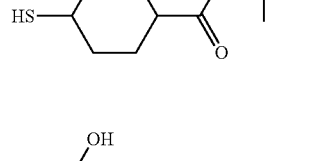
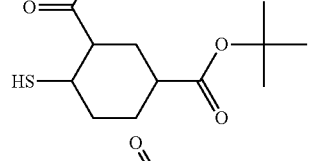
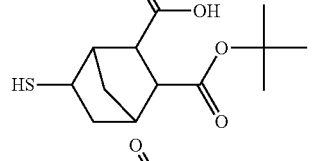
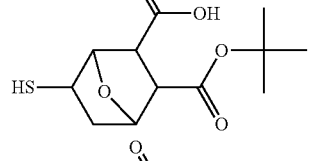
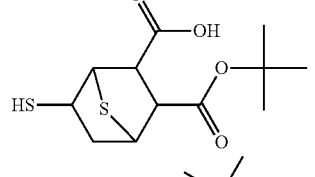
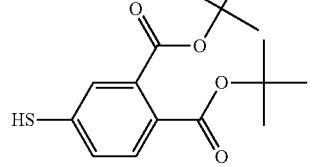
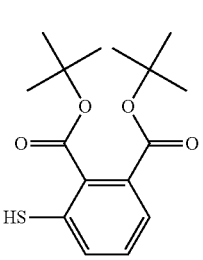
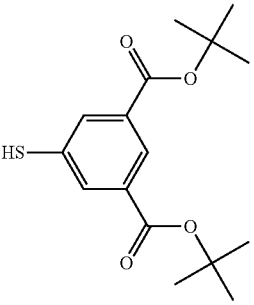
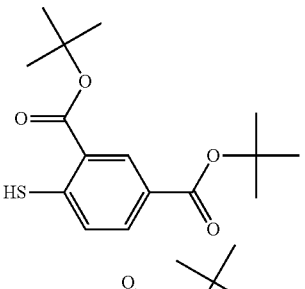
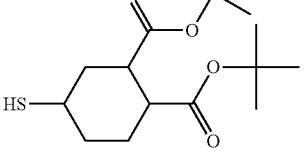
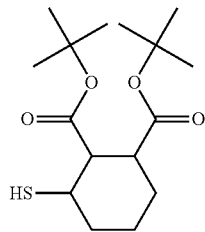
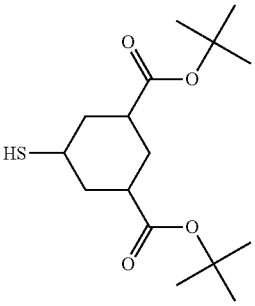
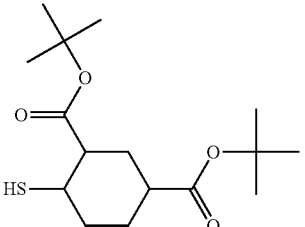
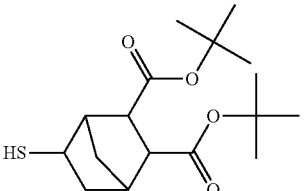
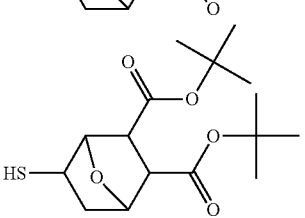

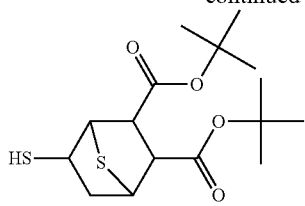

There is no particular limitation on a method of synthesizing the mercapto compound represented by the formula (C1). It is possible to obtain the mercapto compound represented by the formula (C1), for example, by a method of reacting Hal in a compound represented by $(Hal)_{n1}$-A-$(COOR^{c1})_{n2}$ (wherein Hal is a halogen atom such as a chlorine atom, a bromine atom or an iodine atom) with NaSH, or a method of hydrolyzing after reacting with potassium thioacetate, thereby converting into a mercapto group. It is also possible to obtain a mercapto compound represented by the formula (C1) in which $R^{c1}$ is an acid dissociable group or a hydrocarbon group by synthesizing, as the mercapto compound represented by the formula (C1), a compound in which $R^{c1}$ is a hydrogen atom, using the above method, followed by protection of a carboxy group with an acid dissociable group or esterification of the carboxy group using a well-known method.

When n1 is 1, $R^{x1}$ in a disulfide compound represented by $(R^{x1})_{n2}$-A-S—S-A-$(R^{x1})_{n2}$ (wherein $R^{x1}$ is an alkyl group such as a methyl group or an ethyl group, an acyl group such as an acetyl group, or a formyl group) is converted into a carboxy group by oxidization using a well-known method, and then a disulfide bond is cleaved in accordance with a well-known method, thus making it possible to obtain a compound represented by HS-A-$(COOH)_{n2}$ as the mercapto compound represented by the formula (C1). In the compound represented by HS-A-$(COOH)_{n2}$, a carboxy group is protected with an acid dissociable group or esterified by a well-known method, thus making it possible to obtain a mercapto compound represented by the formula (C1) having a hydrocarbon group or an acid dissociable group as $R^{c1}$. In view of high yield of the desired mercapto compound, it is preferred to use a method in which in a compound represented by $(HOOC)_{n2}$-A-S—S-A-$(COOH)_{n2}$ obtained by an oxidation reaction, a disulfide bond is cleaved after a carboxy group is protected with an acid dissociable group or esterified by a well-known method.

In the formula (C1), when n1 is 1, the cyclic group included in A is an aliphatic ring, or a polycyclic ring including an aliphatic ring in the structure thereof, it is possible to obtain a compound represented by the formula (C1) by the following method. In such a method, a compound represented by the following formula (C1-a) is used as a raw material compound. The compound represented by the formula (c1-a) has an n2-valent cyclic group (A' in the formula) including an unsaturated double bond. By reacting this raw material compound with thioacetic acid (AcSH) in a solvent, thioacetic acid is added to an unsaturated double bond, thus obtaining a compound represented by the following formula (C1-b). An acetylthio group possessed by the thus obtained compound represented by the formula (C1-b) is deacetylated, for example, with sodium hydroxide in accordance with a conventional method, followed by a reaction with an acid as required, thus obtaining, as the mercapto compound (C) represented by the formula (C1), a compound represented by the following formula (C1-c).

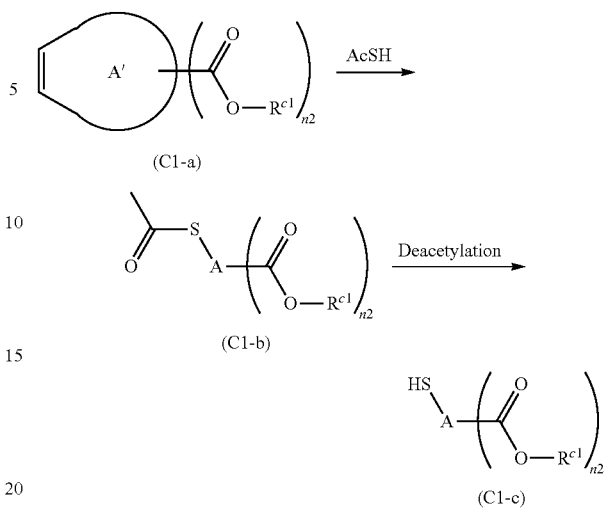

In the formula (C1), when n2 is 2 and both of two $R^{c1}$s are hydrogen atoms, dicarboxylic anhydride represented by the following formula (C1-a') is used as a raw material in place of the compound represented by the above formula (C1-a), thus making it possible to obtain a compound represented by the formula (C1). Regarding this method, the addition of thioacetic acid is the same as that in the method of using the compound represented by the formula (C1-a) as the raw material. After obtaining a compound represented by the following formula (C1-b') by the addition of thioacetic acid, a compound represented by the formula (C1-b') is reacted with a base such as sodium hydroxide in the presence of water, and then reacted with an acid such as hydrochloric acid, thus making it possible to simultaneously perform deacetylation of a mercapto group and conversion of an acid anhydride group into a carboxy group. By such a reaction, a compound represented by the following formula (C1-c') is obtained as the compound represented by the formula (C1).

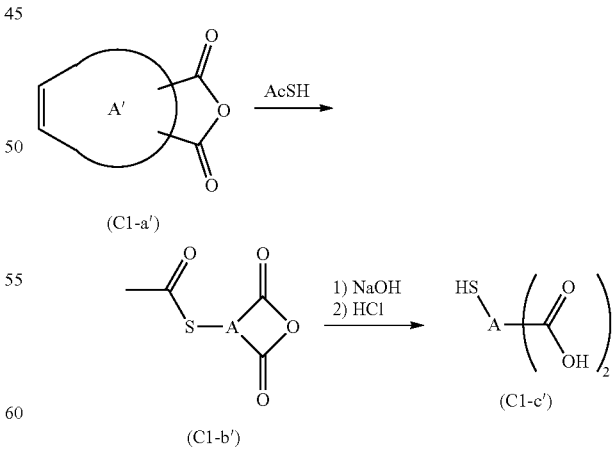

Since it is easier to suppress the occurrence of footing and the generation of residue after development, a mercapto compound represented by the following formula (C1-4) is also preferred as the mercapto compound (C).

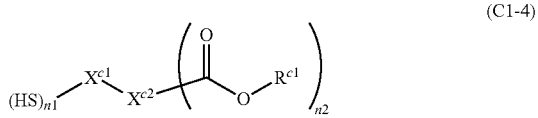

(In the formula (C1-4), $R^{c1}$, n1 and n2 are the same as those in the formula (C1), $X^{c1}$ is an (n1+1)-valent nitrogen-containing heterocyclic group, and $X^2$ is a single bond or an optionally substituted (n2+1)-valent hydrocarbon group.) In the formula (C1-4), when $X^{c2}$ is a single bond, n2 is 1. In the formula (C1-4), it is preferred that $X^{c1}$ and a mercapto group are bonded to each other by a C—S bond, and $X^{c2}$ and a group represented by —CO—O—$R^{c1}$ are bonded to each other by a C—C bond.

In (C1-4) mentioned above, suitable specific examples of the nitrogen-containing heterocyclic group as $X^{c1}$ include groups in which (n1+1) hydrogen atoms are removed from aromatic nitrogen-containing heterocyclic rings such as a pyrrole ring, a pyridine ring, a pyridazine ring, a pyrimidine ring, a pyrazine ring, a triazine ring, a pyrazole ring, an isoxazole ring, an isothiazole ring, an imidazole ring, an oxazole ring, a thiazole ring, a triazole ring, an oxadiazole ring, a thiadiazole ring, an indole ring, an indazole ring, a benzoimidazole ring, a benzoxazole ring, a benzothiazole ring, a quinoline ring, an isoquinoline ring, a cinnoline ring, a phthalazine ring, a quinazoline ring, a quinoxaline ring, a naphthyridine ring, a pteridine ring, a carbazole ring and an acridine ring; aliphatic nitrogen-containing heterocyclic rings such as a pyrrolidine ring, a piperidine ring, a piperazine ring and a morpholine ring; and rings composed of aliphatic nitrogen-containing heterocyclic rings and aromatic hydrocarbon rings such as an indoline ring. $X^{c1}$ is preferably a divalent group. In other words, n1 is preferably 1 in the formula (C1-4). Suitable specific examples of the divalent group as $X^{c1}$ include divalent groups included in Group B mentioned above.

In (C1-4) mentioned above, a suitable specific examples of the hydrocarbon group as $X^{c2}$ include cyclic hydrocarbon groups in which (n2+1) hydrogen atoms are removed from aromatic hydrocarbon rings such as a benzene ring, a naphthalene ring, a biphenyl ring, an anthracene ring and a phenanthrene ring; aliphatic hydrocarbon rings such as a cyclopentane ring, a cyclohexane ring, a cycloheptane ring, a cyclooctane ring, a cyclononane ring, a cyclodecane ring, a cycloundecane ring, a cyclododecane ring, a decalin ring, a hydrindane ring, an adamantane ring, a norbornane ring, a norbornene ring, an isobornane ring, a tricyclodecane ring and a tetracyclododecane ring; and rings composed of aliphatic hydrocarbon rings and aromatic hydrocarbon rings such as a tetralin ring, an indane ring, a cyclopentylbenzene ring and a cyclohexylbenzene ring. The chain aliphatic hydrocarbon group is also preferred as $X^{c2}$. The chain aliphatic hydrocarbon group as $X^{c2}$ may be either linear or branched, and may have one or more unsaturated bonds. $X^{c2}$ is preferably a divalent group. In other words, n1 is preferably 1 in the formula (C1-4).

Suitable specific examples of the divalent group as $X^{c2}$ include an o-phenylene group, a naphthalene-1,2-diyl group, a naphthalene-2,3-diyl group, a naphthalene-1,8-diyl group, a cyclohexane-1,2-diyl group, a 5-norbornene-2,3-diyl group, and an alkylene group having 1 or more and 6 or less carbon atoms (e.g., a methyl group, an ethane-1,2-diyl group, a propane-1,3-diyl group, a butane-1,4-diyl group, a pentane-1,5-diyl group, a hexane-1,6-diyl group).

When $X^{c2}$ is an aromatic hydrocarbon group, the aromatic hydrocarbon group is preferably substituted with an electron withdrawing group. The electron withdrawing group is not particularly limited as long as it is a group which is generally recognized as an electron withdrawing group by a person with an ordinary skill in the art. Typically, the electron withdrawing group is defined as a substituent whose Hammett's substituent constant σm value is positive. The Hammett's σm value is described in detail in, for example, a review written by Yuho TSUNO (Synthetic Organic Chemistry, Vol. 23, No. 8 (1965) pp. 631-642), "Cram, Organic Chemistry [II], 4th edition" p. 656 translated by Yasuhide YUKAWA (Hirokawa-Shoten Ltd.).

Examples of the electron withdrawing group whose σm value is positive include alkoxy groups such as a methoxy group (σm value: 0.12); a hydroxyl group (σm value: 0.12); halogen atoms such as a fluorine atom (σm value: 0.34), a chlorine atom (σm value: 0.37), a bromine atom (σm value: 0.39) and an iodine atom (σm value: 0.35); halogenated alkyl groups such as a trifluoromethyl group (σm value: 0.43); acyloxy groups such as an acetoxy group (σm value: 0.37); acyl groups such as an acetyl group (σm value: 0.38); alkoxycarbonyl groups such as a methoxycarbonyl group (σm value: 0.37); a cyano group (σm value: 0.56); a nitro group (σm value: 0.71); and sulfonyl groups such as a methylsulfonyl group (σm value: 0.60).

The alkoxy group may be either linear or branched. The number of carbon atoms of the alkoxy group is not particularly limited, and is preferably 1 or more and 20 or less, more preferably 1 or more and 10 or less, and particularly preferably 1 or more and 6 or less. Specific examples of the alkoxy group include a methoxy group, an ethoxy group, an n-propyloxy group, an isopropyloxy group, an n-butyloxy group, a sec-butyloxy group, a tert-butyloxy group, an n-pentyloxy group, an isopentyloxy group, a neopentyloxy group and a 2-methylbutyloxy group.

The acyl group may be an aliphatic acyl group, an aromatic acyl group, or an acyl group including an aliphatic group and an aromatic group. The number of carbon atoms of the acyl group is not particularly limited, and is preferably 2 or more and 20 or less, more preferably 2 or more and 10 or less, and particularly preferably 2 or more and 6 or less. Specific examples of the acyl group include an acetyl group, a propionyl group, a butanoyl group, a pivaloyl group and a benzoyl group.

The halogenated alkyl group may be either linear or branched. The number of carbon atoms of the halogenated alkyl group is not particularly limited, and is preferably 1 or more and 20 or less, more preferably 1 or more and 10 or less, and particularly preferably 1 or more and 6 or less. Examples of the halogen atom included in the halogenated alkyl group include a fluorine atom, a chlorine atom, a bromine atom and an iodine atom. The halogen atom is preferably a fluorine atom, a chlorine atom and a bromine atom, and more preferably a fluorine atom and a chlorine atom. The halogenated alkyl group may include a combination of two or more plural halogen atoms. The halogenated alkyl group may be either a group in which halogen atom(s) in the alkyl group are partially substituted with a halogen atom, or a group in which halogen atom(s) in the alkyl group are entirely substituted with a halogen atom. Specific examples of the halogenated alkyl group include a chloromethyl group, a dichloromethyl group, a trichloromethyl group, a bromomethyl group, a dibromomethyl group, a tribromomethyl group, a fluoromethyl group, a difluoromethyl group, a trifluoromethyl group, a 2,2,2-trifluoroethyl group, a pentafluoroethyl group, a heptafluoropropyl group, a perfluorobutyl group, a perfluoropentyl group, a perfluorohexyl group, a perfluoroheptyl group, a perfluorooctyl group, a perfluorononyl group and a perfluorodecyl group.

Examples of the halogen atom include a fluorine atom, a chlorine atom, a bromine atom and an iodine atom.

The acyloxy group may be an aliphatic acyloxy group, an aromatic acyloxy group, or an acyloxy group including an aliphatic group and an aromatic group. The number of carbon atoms of the acyloxy group is not particularly limited, and is preferably 2 or more and 20 or less, more preferably 2 or more and 10 or less, and particularly preferably 2 or more and 6 or less. Specific examples of the acyloxy group include an acetyloxy group, a propionyloxy group, a butanoyloxy group, a pivaloyloxy group and a benzoyloxy group.

The sulfonyl group may be an aliphatic sulfonyl group, an aromatic sulfonyl group, or a sulfonyl group including an aliphatic group and an aromatic group. The number of carbon atoms of the sulfonyl group is not particularly limited, and is preferably 1 or more and 20 or less, more preferably 1 or more and 10 or less, and particularly preferably 1 or more and 6 or less. Specific examples of the sulfonyl group include a methanesulfonyl group, a benzenesulfonyl group, a toluenesulfonyl group, a trifluoromethanesulfonyl group and a difluoromethanesulfonyl group.

Among the electron withdrawing groups described above, at least one selected from the group consisting of a halogen atom, a cyano group, a nitro group, a halogenated alkyl group and a group represented by —CO—O—$Y^c$ is exemplified in view of the fact that the compound represented by the formula (C1-4) has not excessively large molecular weight, satisfactory effect is easily obtained even when using a small amount of the compound represented by the formula (C1-4), and the compound represented by the formula (C1-4) in the photosensitive resin composition has satisfactory solubility. Among these electron withdrawing groups, a halogen atom is preferred and a fluorine atom is more preferred.

$Y^c$ mentioned above is a hydrocarbon group having 1 or more and 10 or less carbon atoms, and specific examples of the hydrocarbon group include alkyl groups such as a methyl group, an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group, an n-heptyl group, an n-octyl group, an n-nonyl group and an n-decyl group; cycloalkyl groups such as a cyclopropyl group, a cyclobutyl group, a cyclopentyl group, a cyclohexyl group, a cycloheptyl group, a cyclooctyl group, a cyclononyl group and a cyclodecyl group; aromatic hydrocarbon groups such as a phenyl group, a naphthalen-1-yl group and a naphthalen-2-yl group; and aralkyl groups such as a benzyl group and a phenethyl group.

In the above formula (C1-4), the linking group composed of $X^{c1}$ and $X^{c2}$ is preferably a divalent or trivalent group included in Group B to Group I mentioned above, and more preferably a divalent group included in Group B to Group I mentioned above.

Suitable specific examples of the mercapto compound represented by the formula (C1-4) include the following mercaptocarboxylic acid compound, or a compound in which a carboxy group in the following mercaptocarboxylic acid is protected with an acid dissociable group. Other suitable specific examples of the mercapto compound represented by the formula (C1-4) include compound in which, in the divalent group included in Group C to Group I, a mercapto group is bonded to one atomic bonding at a heterocyclic group side, and a carboxy group or a carboxy group protected with an acid dissociable group is bonded to the other atomic bonding.

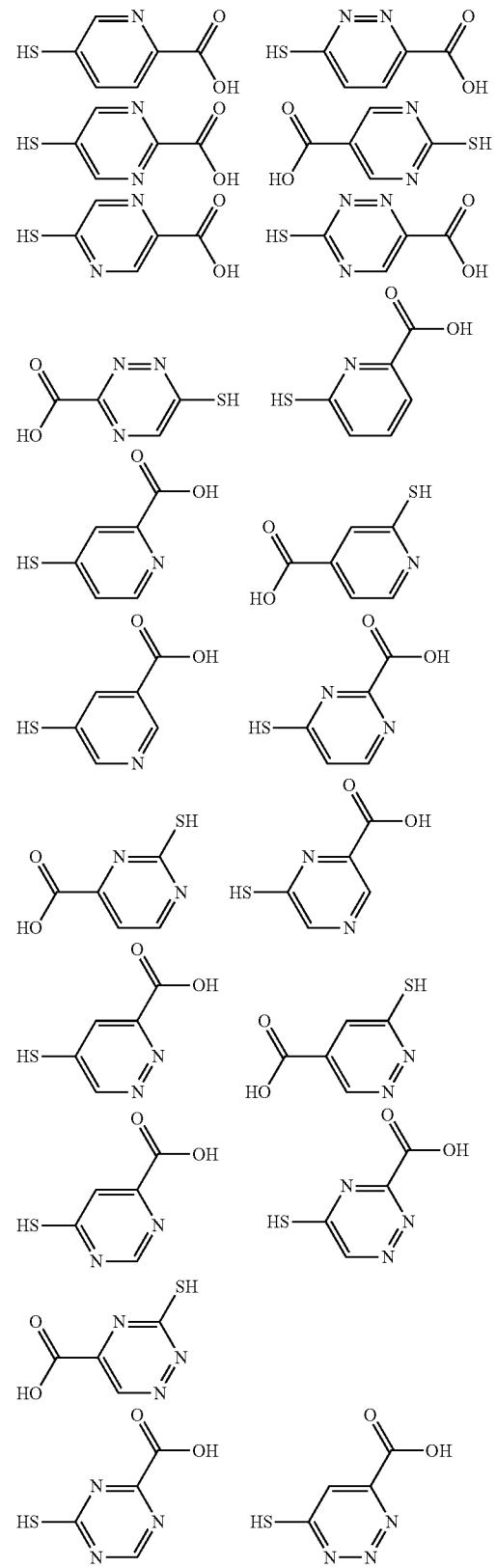

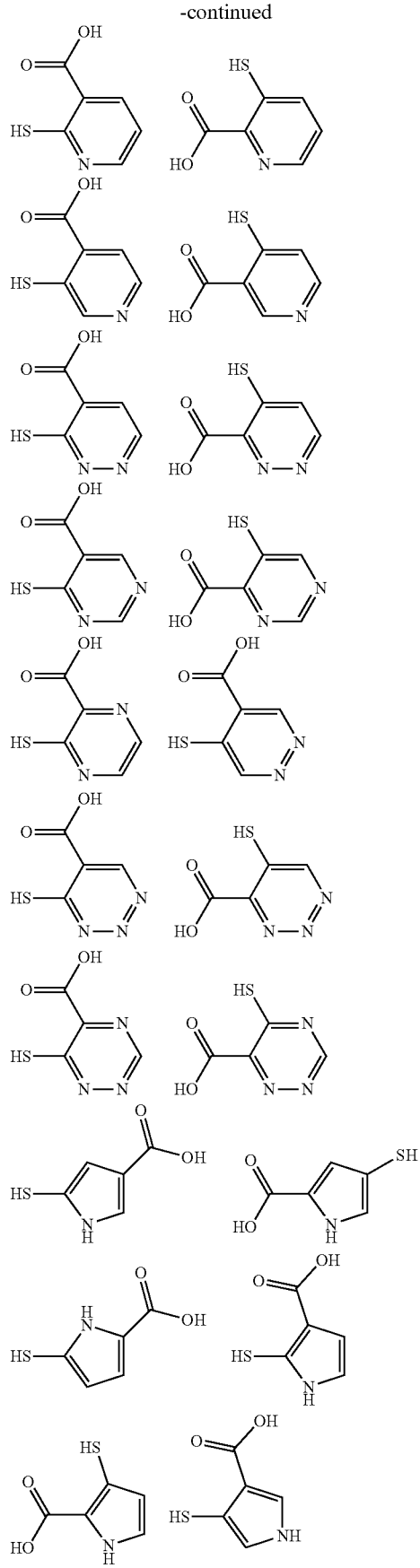
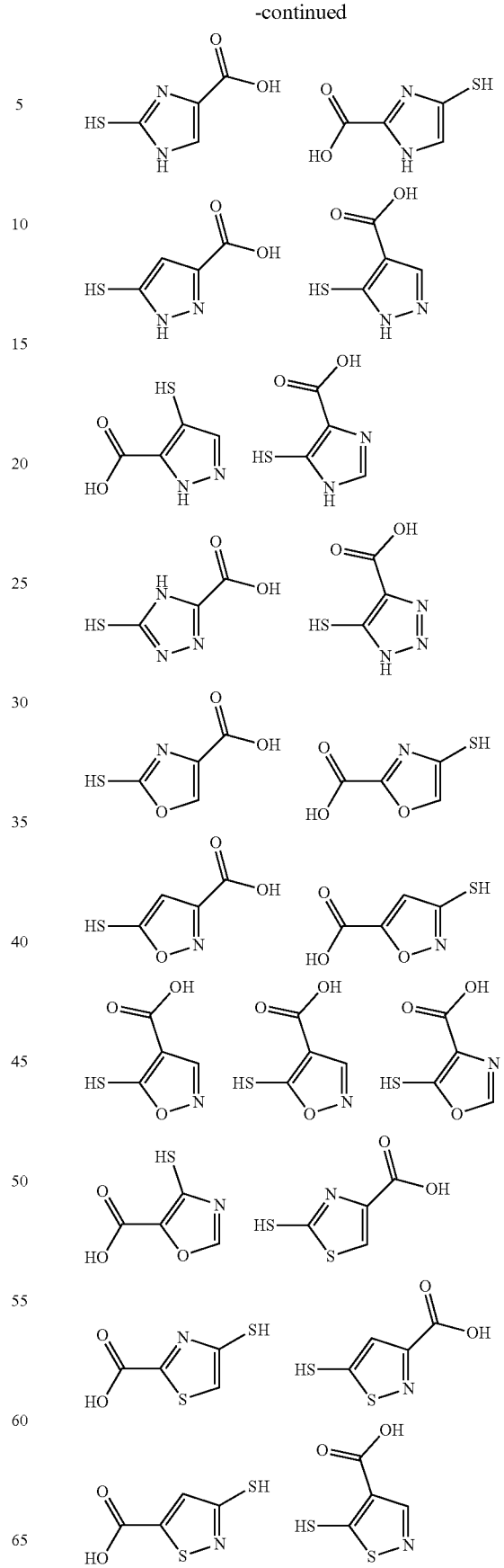

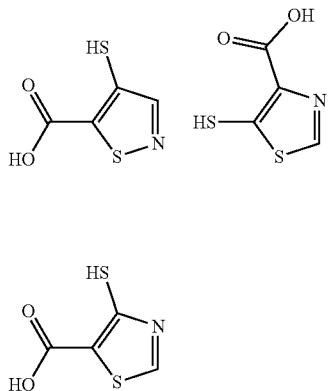

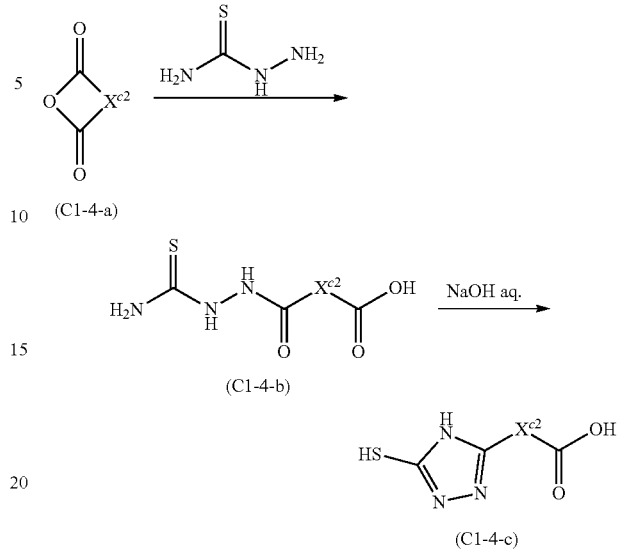

There is no particular limitation on the method of producing a compound represented by the formula (C1-4). For example, when $X^{c2}$ is a single bond, a compound represented by the formula (C1-4) can be produced by applying a known reaction of introducing a carboxy group into a nitrogen-containing heterocyclic compound as a raw material, or a known reaction of introducing a mercapto group. The reaction of introducing a carboxy group includes, for example, a method of lithiating a nitrogen-containing compound substituted with a halogen atom such as bromine and then reacting with a carbon dioxide gas, a method of hydrolyzing a cyano group to be bonded to a nitrogen-containing heterocyclic ring, a Reissert reaction and the like. Examples of the method of introducing a mercapto group include a method of preparing a Grignard reagent from a nitrogen-containing compound substituted with a halogen atom such as bromine and reacting the resulting Grignard reagent with sulfur, a method of reacting a nitrogen-containing heterocyclic compound substituted with a halogen atom such as chlorine with thiourea to form a thiouronium salt and then decomposing the thiouronium salt with ammonia and the like. The reaction of introducing a carboxyl group and the reaction of introducing a mercapto group are not limited thereto.

When $X^{c2}$ is an optionally substituted hydrocarbon group, a compound represented by the formula (C1-4) can be produced by introducing a carboxy group and a mercapto group into a compound having a group composed of $X^{c1}$ and $X^{c2}$ as a main skeleton using various methods.

When $X^{c2}$ is an optionally substituted hydrocarbon group, a compound represented by the formula (C1-4) can be produced by a method including forming $X^{c1}$ as a nitrogen-containing heterocyclic group formed by ring closure of a raw material compound including $X^{c2}$ or an intermediate. The structure of the raw material compound or intermediate to be subjected to a ring-closing reaction is appropriately selected according to the types of the nitrogen-containing heterocyclic group to be formed by ring closure.

As an example, when n1 and n2 are respectively 1 and $X^{c1}$ is a 1,2,4-triazole-3,5-diyl group, it is possible to obtain a compound represented by the formula (C1-4-c) as the compound represented by the formula (C1-4) by reacting dicarboxylic anhydride represented by the formula (C1-4a) with thiocarbamide to obtain an intermediate represented by the formula (C1-4-b), followed by ring closure of the intermediate in an aqueous sodium hydroxide solution.

As other examples, when n1 and n2 are respectively 1 and $X^1$ is a 1,3,4-oxadiazole-2,5-diyl group, it is possible to obtain a compound represented by the formula (C1-4-f) as the compound represented by the formula (C1-4), for example, by reacting a hydrazide compound represented by the formula (C1-4-d) with carbon disulfide to obtain an intermediate represented by the formula (C1-4-e) and reacting the intermediate with a base such as sodium hydroxide in the presence of water, followed by a reaction with an acid such as hydrochloric acid. $R^{c0}$ is a hydrogen atom, or an organic group (e.g., a methyl group or an ethyl group) which does not inhibit the following synthesis reaction. $R^{c0}$ may be an acid dissociable group. When $R^{c0}$ is an acid dissociable group, it is possible to use a compound represented by the formula (C1-4-e) as the compound represented by the formula (C1-4).

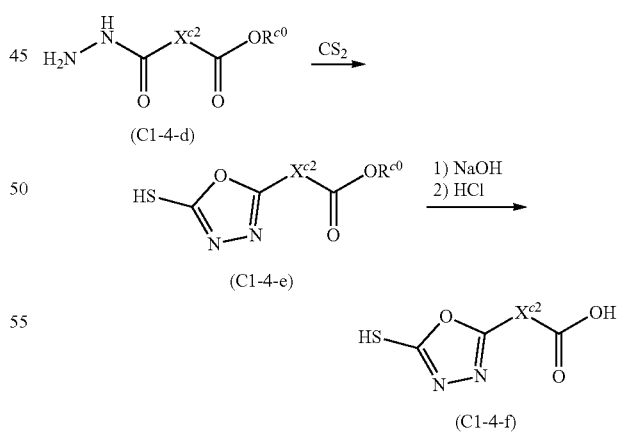

The photosensitive resin composition may include other mercapto compounds together with a mercapto compound (C) which is a mercapto compound represented by the formula (C1). Preferred examples of other mercapto compounds include a compound represented by the following formula (C2).

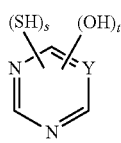

(c2)

In the above formula (c2), Y represents N or CH, s represents an integer of 1 to 3, t represents an integer of 0 to 2, and s+t is 2 or 3.

Specific examples of the compound represented by the above formula (c2) include 2,4-dimercapto-1,3,5-triazine, 2,4,6-trimercapto-1,3,5-triazine, 2,4-dimercapto-1,3,5-triazin-6-ol, 2-mercapto-1,3,5-triazine-4,6-diol, 2,4-dimercaptopyrimidine, 2-mercaptopyrimidin-4-ol, 2-mercaptopyrimidine-4,6-diol and the like.

The mercapto compound (C) is used in the amount in a range of 0.01 part by mass or more and 5 parts by mass or less, and particularly preferably 0.05 part by mass or more and 2 parts by mass or less, relative to 100 parts by mass of the total mass of the above resin (B) and an alkali soluble resin (D) mentioned later. When the amount of the mercapto compound (C) added is 0.01 part by mass or more, further effect tends to be exerted on suppression of the occurrence of footing and the generation of development residue. Meanwhile, when the amount is 5 parts by mass or less, it is possible to form a satisfactory plated article.

<Alkali-Soluble Resin (D)>

It is preferred that the photosensitive resin composition further contains an alkali-soluble resin (D) in order to improve crack resistance. The alkali-soluble resin as referred to herein may be determined as follows. A solution of the resin having a resin concentration of 20% by mass (solvent: propylene glycol monomethyl ether acetate) is used to form a resin film having a thickness of 1 μm on a substrate, and immersed in an aqueous 2.38% by mass TMAH solution for 1 min. When the resin was dissolved in an amount of 0.01 μm or more, the resin is defined as being alkali soluble. The alkali-soluble resin (D) is preferably at least one selected from the group consisting of novolak resin (D1), polyhydroxystyrene resin (D2), and acrylic resin (D3).

[Novolak Resin (D1)]

A novolak resin is prepared by addition condensation of, for example, aromatic compounds having a phenolic hydroxy group (hereinafter, merely referred to as "phenols") and aldehydes in the presence of an acid catalyst.

Examples of the above phenols include phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 2,6-xylenol, 3,4-xylenol, 3,5-xylenol, 2,3,5-trimethyl phenol, 3,4,5-trimethyl phenol, p-phenylphenol, resorcinol, hydroquinone, hydroquinone monomethyl ether, pyrogallol, phloroglycinol, hydroxydiphenyl, bisphenol A, gallic acid, gallic acid ester, α-naphthol, β-naphthol, and the like. Examples of the above aldehydes include formaldehyde, furfural, benzaldehyde, nitrobenzaldehyde, acetaldehyde, and the like. The catalyst used in the addition condensation reaction is not particularly limited, and examples thereof include hydrochloric acid, nitric acid, sulfuric acid, formic acid, oxalic acid, acetic acid, etc., for acid catalyst.

The flexibility of the novolak resins can be enhanced more when o-cresol is used, a hydrogen atom of a hydroxyl group in the resins is substituted with other substituents, or bulky aldehydes are used.

The mass average molecular weight of novolac resin (D1) is not particularly limited as long as the purpose of the present invention is not impaired, but the mass average molecular weight is preferably 1,000 or more and 50,000 or less.

[Polyhydroxystyrene Resin (D2)]

The hydroxystyrene compound to constitute the polyhydroxystyrene resin (D2) is exemplified by p-hydroxystyrene, α-methylhydroxystyrene, α-ethylhydroxystyrene, and the like. Furthermore, the polyhydroxystyrene resin (D2) is preferably prepared to give a copolymer with a styrene resin. The styrene compound to constitute the styrene resin is exemplified by styrene, chlorostyrene, chloromethylstyrene, vinyltoluene, α-methylstyrene, and the like.

The mass average molecular weight of the polyhydroxystyrene resin (D2) is not particularly limited as long as the purpose of the present invention is not impaired, but the mass average molecular weight is preferably 1,000 or more and 50,000 or less.

[Acrylic Resin (D3)]

It is preferable that the acrylic resin (D3) includes a constituent unit derived from a polymerizable compound having an ether bond and a constituent unit derived from a polymerizable compound having a carboxyl group.

Examples of the above polymerizable compound having an ether bond include (meth)acrylic acid derivatives having an ether bond and an ester bond such as 2-methoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolypropylene glycol (meth)acrylate, tetrahydrofurfuryl (meth)acrylate, and the like. The above polymerizable compound having an ether bond is preferably, 2-methoxyethyl acrylate, and methoxytriethylene glycol acrylate. These polymerizable compounds may be used alone, or in combinations of two or more.

Examples of the above polymerizable compound having a carboxy group include monocarboxylic acids such as acrylic acid, methacrylic acid and crotonic acid; dicarboxylic acids such as maleic acid, fumaric acid and itaconic acid; compounds having a carboxy group and an ester bond such as 2-methacryloyloxyethyl succinic acid, 2-methacryloyloxyethyl maleic acid, 2-methacryloyloxyethyl phthalic acid, 2-methacryloyloxyethyl hexahydrophthalic acid and the like. The above polymerizable compound having a carboxy group is preferably, acrylic acid and methacrylic acid. These polymerizable compounds may be used alone, or in combinations of two or more thereof.

The mass average molecular weight of the acrylic resin (D3) is not particularly limited as long as the purpose of the present invention is not impaired, but the mass average molecular weight is preferably 50,000 or more and 800,000 or less.

The content of the alkali-soluble resin (D) is such that when the total amount of the above resin (B) and the alkali-soluble resin (D) is taken as 100 parts by mass, the content is preferably 0 parts by mass or more and 80 parts by mass or less, and more preferably 0 parts by mass or more and 60 parts by mass or less. By setting the content of the alkali-soluble resin (D) to the range described above, there is a tendency for resistance to cracking to increase, and film loss at the time of development can be prevented.

<Acid Diffusion Control Agent (E)>

In order to improve the configuration of resist pattern used as a template, the post-exposure delay stability of photosensitive resin film and the like, it is preferable that the photosensitive resin composition further contains an acid diffusion control agent (E). The acid diffusion control agent (E) is preferably a nitrogen-containing compound (E1), and an organic carboxylic acid, or an oxo acid of phosphorus or a derivative thereof (E2) may be further included as needed.

[Nitrogen-Containing Compound (E1)]

Examples of the nitrogen-containing compound (E1) include trimethylamine, diethylamine, triethylamine, di-n-propylamine, tri-n-propylamine, tri-n-pentylamine, tribenzylamine, diethanolamine, triethanolamine, n-hexylamine, n-heptyl amine, n-octyl amine, n-nonyl amine, ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, formamide, N-methylformamide, N,N-dimethylformamide, acetamide, N-methylacetamide, N,N-dimethylacetamide, propionamide, benzamide, pyrrolidone, N-methylpyrrolidone, methylurea, 1,1-dimethylurea, 1,3-dimethylurea, 1,1,3,3,-tetramethylurea, 1,3-diphenylurea, imidazole, benzimidazole, 4-methylimidazole, 8-oxyquinoline, acridine, purine, pyrrolidine, piperidine, 2,4,6-tri(2-pyridyl)-S-triazine, morpholine, 4-methylmorpholine, piperazine, 1,4-dimethylpiperazine, 1,4-diazabicyclo[2.2.2]octane and pyridine, and substituted pyridines such as 2,6-di-tert-butylpyridine and 2,6-diphenylpyridine. It is also possible to use, as the nitrogen-containing compound (E1), tetrakis(1,2,2,6,6-pentamethyl-4-piperidyl)1,2,3,4-butanetetracarboxylate, a condensate of 1,2,3,4-butanetetracarboxylic acid, 1,2,2,6,6,-pentamethyl-4-piperidinol and β,β,β',β'-tetramethyl-3,9-(2,4,8,10-tetraoxaspiro[5,5]undecane)-diethanol, a hindered amine compound of dimethyl succinate and a polymer of 4-hydroxy-2,2,6,6-tetramethyl-1-piperidineethanol. These may be used alone, or in combinations of two or more thereof.

The nitrogen-containing compound (E1) may be used in an amount typically in the range of 0 parts by mass or more and 5 parts by mass or less, and particularly preferably in the range of 0 parts by mass or more and 3 parts by mass or less, with respect to 100 parts by mass of total mass of the above resin (B) and the above alkali-soluble resin (D).

[Organic Carboxylic Acid or Oxo Acid of Phosphorus or Derivative Thereof (E2)]

Among the organic carboxylic acid, or the oxo acid of phosphorus or the derivative thereof (E2), specific preferred examples of the organic carboxylic acid include malonic acid, citric acid, malic acid, succinic acid, benzoic acid, salicylic acid and the like, and salicylic acid is particularly preferred.

Examples of the oxo acid of phosphorus or derivatives thereof include phosphoric acid and derivatives such as esters thereof such as phosphoric acid, phosphoric acid di-n-butyl ester, and phosphoric acid diphenyl ester; phosphonic acid and derivatives such as esters thereof such as phosphonic acid, phosphonic acid dimethyl ester, phosphonic acid di-n-butyl ester, phenylphosphonic acid, phosphonic acid diphenyl ester, and phosphonic acid dibenzyl ester; and phosphinic acid and derivatives such as esters thereof such as phosphinic acid and phenylphosphinic acid; and the like. Among these, phosphonic acid is particularly preferred. These may be used alone, or in combinations of two or more thereof.

The organic carboxylic acid or oxo acid of phosphorus or derivative thereof (E2) may be used in an amount usually in the range of 0 parts by mass or more and 5 parts by mass or less, and particularly preferably in the range of 0 parts by mass and 3 parts by mass or less, with respect to 100 parts by mass of total mass of the above resin (B) and the above alkali-soluble resin (D).

Moreover, in order to form a salt to allow for stabilization, the organic carboxylic acid, or the oxo acid of phosphorous or the derivative thereof (E2) is preferably used in an amount equivalent to that of the above nitrogen-containing compound (E1).

<Organic Solvent (S)>

The photosensitive resin composition contains an organic solvent (S). There is no particular limitation on the types of the organic solvent (S) as long as the objects of the present invention are not impaired, and an organic solvent appropriately selected from those conventionally used for positive-type photosensitive resin compositions can be used.

Specific examples of the organic solvent (S) include ketones such as acetone, methyl ethyl ketone, cyclohexanone, methyl isoamyl ketone, and 2-heptanone; polyhydric alcohols and derivatives thereof, like monomethyl ethers, monoethyl ethers, monopropyl ethers, monobutyl ethers and monophenyl ethers, such as ethylene glycol, ethylene glycol monoacetate, diethylene glycol, diethylene glycol monoacetate, propylene glycol, propylene glycol monoacetate, dipropylene glycol and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, methyl pyruvate, ethylethoxy acetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanate, 3-methoxybutyl acetate and 3-methyl-3-methoxybutyl acetate; aromatic hydrocarbons such as toluene and xylene; and the like. These may be used alone, or as a mixture of two or more thereof.

There is no particular limitation on the content of the organic solvent (S) as long as the objects of the present invention are not impaired. In a case where a photosensitive resin composition is used for a thick-film application such that a photosensitive resin layer obtained by the spin coating method and the like has a film thickness of 10 μm or more, the organic solvent (S) is preferably used in a range where the solid content concentration of the photosensitive resin composition is 30% by mass or more and 55% by mass or less.

<Other Components>

The photosensitive resin composition may further contain a polyvinyl resin for improving plasticity. Specific examples of the polyvinyl resin include polyvinyl chloride, polystyrene, polyhydroxystyrene, polyvinyl acetate, polyvinylbenzoic acid, polyvinyl methyl ether, polyvinyl ethyl ether, polyvinyl alcohol, polyvinyl pyrrolidone, polyvinyl phenol, and copolymers thereof, and the like. The polyvinyl resin is preferably polyvinyl methyl ether in view of lower glass transition temperatures.

Further, the photosensitive resin composition may also contain an adhesive auxiliary agent in order to improve the adhesiveness between a template formed with the photosensitive resin composition and a metal substrate.

Also, the photosensitive resin composition may further contain a surfactant for improving coating characteristics, defoaming characteristics, leveling characteristics, and the like. As the surfactant, for example, a fluorine-based surfactant or a silicone-based surfactant is preferably used. Specific examples of the fluorine-based surfactant include commercially available fluorine-based surfactants such as BM-1000 and BM-1100 (both manufactured by B.M-Chemie Co., Ltd.), Megafac F142D, Megafac F172, Megafac F173 and Megafac F183 (all manufactured by Dainippon Ink And Chemicals, Incorporated), Flolade FC-135, Flolade FC-170C, Flolade FC-430 and Flolade FC-431 (all manufactured by Sumitomo 3M Ltd.), Surflon S-112, Surflon S-113, Surflon S-131, Surflon S-141 and Surflon S-145 (all manufactured by Asahi Glass Co., Ltd.), SH-28PA, SH-190, SH-193, SZ-6032 and SF-8428 (all manufactured by Toray Silicone Co., Ltd.) and the like, but not limited thereto. As the silicone-based surfactant, an unmodified silicone-based surfactant, a polyether modified silicone-based surfactant, a polyester modified silicone-based surfactant, an alkyl modified silicone-based surfactant, an aralkyl modified silicone-based surfactant, a reactive silicone-based surfactant, and the like, can be preferably used. As the silicone-based surfactant, commercially available silicone-based surfactant can be used. Specific examples of the commercially available silicone-based surfactant include Paintad M (manufactured by Dow Corning Toray Co., Ltd.), Topica K1000, Topica K2000, and Topica K5000 (all manufactured by Takachiho Industry Co., Ltd.), XL-121 (polyether modified silicone-based surfactant, manufactured by Clariant Co.), BYK-310 (polyester modified silicone-based surfactant, manufactured by BYK), and the like.

Additionally, in order to finely adjust the solubility in a developing solution, the photosensitive resin composition may further contain an acid, an acid anhydride, or a solvent having a high boiling point.

Specific examples of the acid and acid anhydride include monocarboxylic acids such as acetic acid, propionic acid, n-butyric acid, isobutyric acid, n-valeric acid, isovaleric acid, benzoic acid, and cinnamic acid; hydroxymonocarboxylic acids such as lactic acid, 2-hydroxybutyric acid, 3-hydroxybutyric acid, salicylic acid, m-hydroxybenzoic acid, p-hydroxybenzoic acid, 2-hydroxycinnamic acid, 3-hydroxycinnamic acid, 4-hydroxycinnamic acid, 5-hydroxyisophthalic acid, and syringic acid; polyvalent carboxylic acids such as oxalic acid, succinic acid, glutaric acid, adipic acid, maleic acid, itaconic acid, hexahydrophthalic acid, phthalic acid, isophthalic acid, terephthalic acid, 1,2-cyclohexanedicarboxylic acid, 1,2,4-cyclohexanetricarboxylic acid, butanetetracarboxylic acid, trimellitic acid, pyromellitic acid, cyclopentanetetracarboxylic acid, butanetetracarboxylic acid, and 1,2,5,8-naphthalenetetracarboxylic acid; acid anhydrides such as itaconic anhydride, succinic anhydride, citraconic anhydride, dodecenylsuccinic anhydride, tricarbanilic anhydride, maleic anhydride, hexahydrophthalic anhydride, methyltetrahydrophthalic anhydride, Himic anhydride, 1,2,3,4-butanetetracarboxylic anhydride, cyclopentanetetracarboxylic dianhydride, phthalic anhydride, pyromellitic anhydride, trimellitic anhydride, benzophenonetetracarboxylic anhydride, ethylene glycol bis anhydrous trimellitate, and glycerin tris anhydrous trimellitate; and the like.

Furthermore, specific examples of the solvent having a high boiling point include N-methylformamide, N,N-dimethylformamide, N-methylformanilide, N-methylacetamide, N,N-dimethlyacetamide, N-methylpyrrolidone, dimethyl sulfoxide, benzyl ethyl ether, dihexyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, phenyl cellosolve acetate, and the like.

Moreover, the photosensitive resin composition may further contain a sensitizer for improving the sensitivity.

<Method of Preparing Chemically Amplified Positive-Type Photosensitive Resin Composition>

A chemically amplified positive-type photosensitive resin composition is prepared by mixing and stirring the above components by the common method. Machines which can be used for mixing and stirring the above components include dissolvers, homogenizers, 3-roll mills and the like. After uniformly mixing the above components, the resulting mixture may be filtered through a mesh, a membrane filter and the like.

<<Photosensitive Dry Film>>

A photosensitive dry film includes a substrate film, and a photosensitive resin layer formed on the surface of the substrate film. The photosensitive resin layer is made of the above-mentioned photosensitive resin compositions.

As the substrate film, a film having optical transparency is preferable. Specifically, a polyethylene terephthalate (PET) film, a polypropylene (PP) film, a polyethylene (PE) film, and the like. In view of excellent balance between the optical transparency and the breaking strength, a polyethylene terephthalate (PET) film is preferable.

The above-mentioned photosensitive resin composition is applied on the substrate film to form a photosensitive resin layer, and thereby a photosensitive dry film is manufactured. When the photosensitive resin layer is formed on the substrate film, a photosensitive resin composition is applied and dried on the substrate film using an applicator, a bar coater, a wire bar coater, a roller coater, a curtain flow coater, and the like, so that a film thickness after drying is preferably 0.5 μm or more and 300 μm or less, more preferably 1 μm or more and 300 μm or less, and particularly preferably 3 μm or more and 100 μm or less.

The photosensitive dry film may have a protective film on the photosensitive resin layer. Examples of the protective film include a polyethylene terephthalate (PET) film, a polypropylene (PP) film, a polyethylene (PE) film, and the like.

<<Patterned Resist Film, and Method of Producing Substrate with Template>>

There is no particular limitation on a method of forming a patterned resist film on a metal surface of a substrate having the metal surface using the photosensitive resin composition described above. Such a patterned resist film is suitably used as a template for forming a plated article. A suitable method includes a manufacturing method of a patterned resist film that includes:

laminating a photosensitive resin layer on a metal surface of a substrate having a metal surface, the layer including the chemically amplified positive-type photosensitive resin composition, exposing the photosensitive resin layer through irradiation with an active ray or radiation in a position-selective manner, and developing the exposed photosensitive resin layer.

A method of producing a substrate with a template for forming a plated article is the same as the method of producing a patterned resist film, except that a template for forming a plated article is formed by development in the developing.

There is no particular limitation for the substrate on which a photosensitive resin layer is laminated, and conventionally known substrates can be used. Examples include substrates for electronic part, substrates having a predetermined wire pattern formed thereon, and the like. Substrates having a metal surface are used as the above substrate. As metal species constituting a metal surface, copper, gold and aluminum are preferred, and copper is more preferred.

The photosensitive resin layer is laminated on the substrate, for example, as follows. In other words, a liquid photosensitive resin composition is coated onto a substrate, and the coating is heated to remove the solvent and thus to form a photosensitive resin layer having a desired thickness. The thickness of the photosensitive resin layer is not particularly limited as long as it is possible to form a resist pattern serving as a template which has a desired thickness. The thickness of the photosensitive resin layer is not particularly limited, but is preferably 0.5 µm or more, more preferably 0.5 µm or more and 300 µm or less, and particularly preferably 1 µm or more and 150 µm or less, and most preferably 3 µm or more and 100 µm or less.

As a method of applying a photosensitive resin composition onto a substrate, methods such as the spin coating method, the slit coat method, the roll coat method, the screen printing method and the applicator method can be employed. Pre-baking is preferably performed on a photosensitive resin layer. The conditions of pre-baking may differ depending on the components in a photosensitive resin composition, the blending ratio, the thickness of a coating film and the like. They are usually about 2 minutes or more and 120 minutes or less at 70° C. or more and 200° C. or less, and preferably 80° C. or more and 150° C. or less.

The photosensitive resin layer formed as described above is selectively irradiated (exposed) with an active ray or radiation, for example, an ultraviolet radiation or visible light with a wavelength of 300 nm or more and 500 nm or less through a mask having a predetermined pattern.

Low pressure mercury lamps, high pressure mercury lamps, super high pressure mercury lamps, metal halide lamps, argon gas lasers, etc. can be used for the light source of the radiation. The radiation may include micro waves, infrared rays, visible lights, ultraviolet rays, X-rays, γ-rays, electron beams, proton beams, neutron beams, ion beams, etc. The irradiation dose of the radiation may vary depending on the constituent of the photosensitive resin composition, the film thickness of the photosensitive resin layer, and the like. For example, when an ultra high-pressure mercury lamp is used, the dose may be 100 mJ/cm$^2$ or more and 10,000 mJ/cm$^2$ or less. The radiation includes a light ray to activate the acid generator (A) in order to generate an acid.

After the exposure, the diffusion of acid is promoted by heating the photosensitive resin layer using a known method to change the alkali solubility of the photosensitive resin layer at an exposed portion in the photosensitive resin film.

Subsequently, the exposed photosensitive resin layer is developed in accordance with a conventionally known method, and an unnecessary portion is dissolved and removed to form a predetermined resist pattern, or a template for forming a plated article. At this time, as the developing solution, an alkaline aqueous solution is used.

As the developing solution, an aqueous solution of an alkali such as, for example, sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, 1,8-diazabicyclo[5.4.0]-7-undecene or 1,5-diazabicyclo[4.3.0]-5-nonane can be used. Also, an aqueous solution prepared by adding an adequate amount of a water-soluble organic solvent such as methanol or ethanol, or a surfactant to the above aqueous solution of the alkali can be used as the developing solution.

The developing time may vary depending on the constituent of the photosensitive resin composition, the film thickness of the photosensitive resin layer, and the like. Usually, the developing time is 1 minute or more and 30 minutes or less. The method of the development may be any one of a liquid-filling method, a dipping method, a paddle method, a spray developing method, and the like.

After development, it is washed with running water for 30 seconds or more and 90 seconds or less, and then dried with an air gun, an oven, and the like. In this manner, it is possible to form a resist pattern which has been patterned in a predetermined pattern on a metal surface of a substrate having a metal surface. Furthermore, in this manner, it is possible to manufacture a substrate with a template having a resist pattern serving as a template on a metal surface of a substrate having a metal surface.

<<Method of Manufacturing Plated Article>>

A conductor such as a metal may be embedded, by plating, into a nonresist portion (a portion removed with a developing solution) in the template formed by the above method on the substrate to form a plated article, for example, like a contacting terminal such as a bump or a metal post. Note that there is no particular limitation on the method of plate processing, and various conventionally known methods can be used. As a plating liquid, in particular, a solder plating liquid, a copper plating liquid, a gold plating liquid and a nickel plating liquid are suitably used. Finally, the remaining template is removed with a stripping liquid and the like in accordance with a conventional method.

According to the above method, a resist pattern serving as a template is formed while suppressing the occurrence of "footing" in which the width of the bottom (surface side of the support) becomes narrower than that of the top (front surface side of the resist layer) in the nonresist portion and the generation of development residue. Use of the thus produced substrate with a template whose footing is suppressed enables production of a plated article excellent in adhesion to the substrate.

<<Mercapto Compound>>

The present invention provides, as a novel mercapto compound, a compound represented by the following formula (C1-1) in which n2 is 2. A mercapto compound represented by the formula (C1-1) is included in the above mercapto compound (C) as a component of the photosensitive resin composition. As mentioned above, the mercapto compound represented by the formula (C1-1) is useful for suppressing the occurrence of footing and the generation of residue after development in the chemically amplified positive-type photosensitive resin composition, like the mercapto compound (C). The mercapto compound represented by the formula (C1-1) is the same as the mercapto compound represented by the formula (C1-1) described about the photosensitive resin composition, except that n2 is 2.

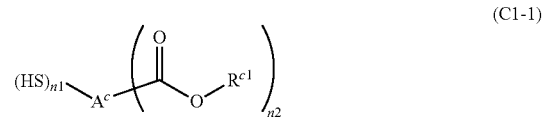

(C1-1)

In the formula (C1-1), $A^c$ is an (n1+n2)-valent aliphatic cyclic group which optionally has one or more substituents and optionally includes one or more heteroatoms, $R^{c1}$ each independently represent a hydrogen atom, a hydrocarbon group or an acid dissociable group, n1 is an integer of 1 or more and 4 or less, n2 is 2, and at least one of $R^{c1}$s is a hydrogen atom or an acid dissociable group.

The mercapto compound represented by the above formula (C1-1) is preferably a mercapto compound represented by the following formula (C1-3).

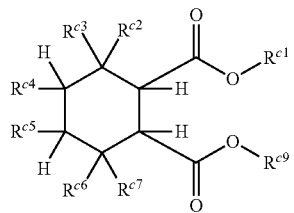

(C1-3)

(In the formula (C1-3), $R^{c1}$ is the same as that in the formula (C1-1), $R^{c2}$ and $R^{c6}$ are each independently a hydrogen atom or an alkyl group, or $R^{c2}$ and $R^{c6}$ may be bonded to each other to form a divalent group selected from the group consisting of —O—, —S—, —CH$_2$— and —C(CH$_3$)$_2$—, $R^3$, $R^{c4}$, $R^{c5}$ and $R^{c7}$ are each independently a hydrogen atom or a mercapto group, $R^{c9}$ is a hydrogen atom, a hydrocarbon group or an acid dissociable group, at least one of $R^{c1}$ and $R^{c9}$ is a hydrogen atom or an acid dissociable group, and at least one of $R^{c3}$, $R^{c4}$, $R^{c5}$ and $R^{c7}$ is a mercapto group.)

In the above formula (C1-3), $R^{c9}$ is the same as $R^{c1}$.

Suitable specific examples of the mercapto compound represented by the above formula (C1-1) in which n2 is 2 include the following compounds.

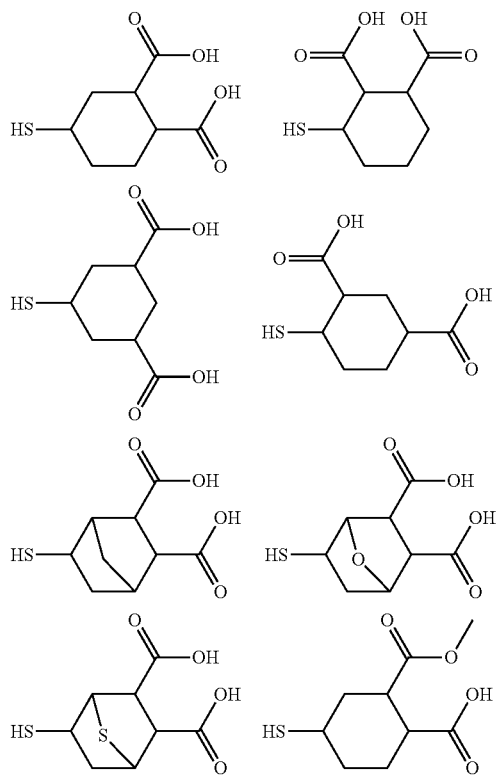

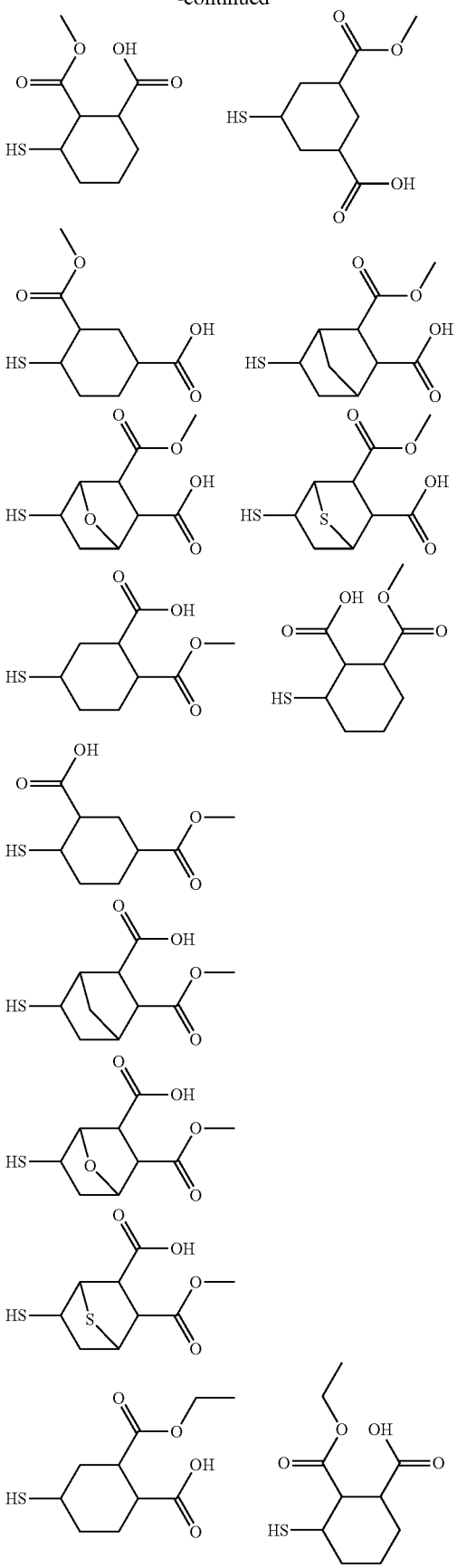

-continued

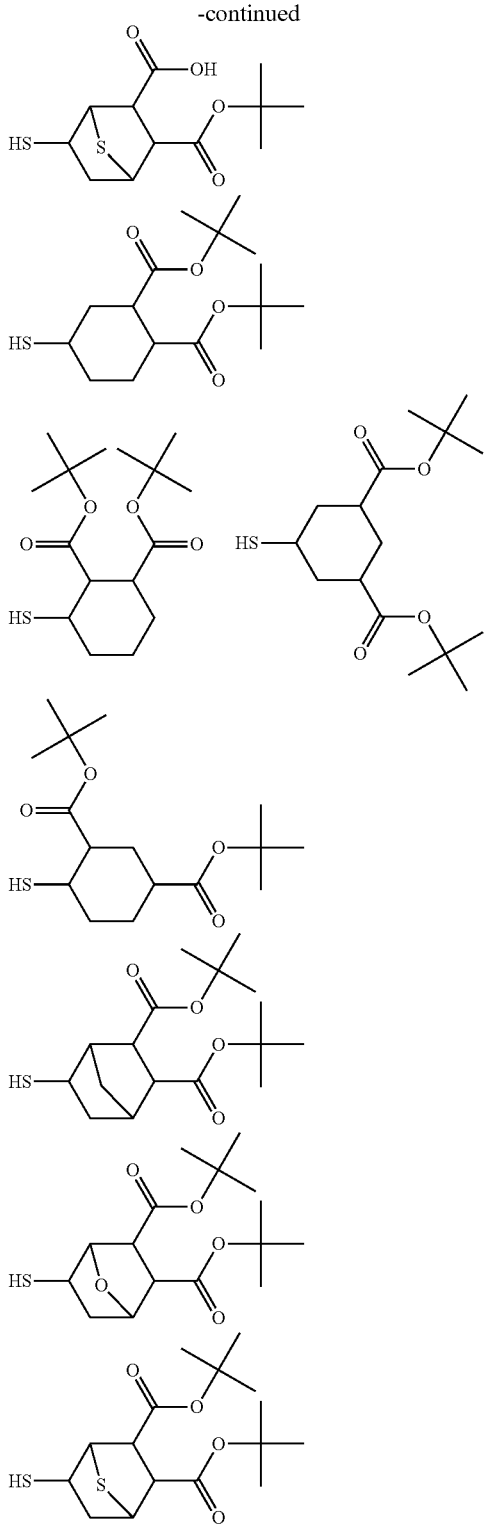

The present invention also provides, as a novel mercapto compound, a compound represented by the following formula (C1-5). A mercapto compound represented by the formula (C1-5) is included in the above mercapto compound (C) as a component of the photosensitive resin composition. As mentioned above, the mercapto compound represented by the formula (C1-5) is useful for suppressing the occurrence of footing and the generation of residue after development in the chemically amplified positive-type photosensitive resin composition, like the mercapto compound (C). The mercapto compound represented by the formula (C1-5) is the same as the mercapto compound represented by the formula (C1-4) described about the photosensitive resin composition, except that $X^{c2}$ is limited to $X^{c3}$ which is an (n2+1)-valent aromatic hydrocarbon group substituted with an electron withdrawing group.

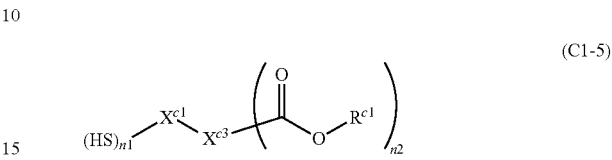

(In the formula (C1-5), $R^{c1}$s each independently represent a hydrogen atom, a hydrocarbon group or an acid dissociable group, n1 is an integer of 1 or more and 4 or less, n2 is 1 or 2, at least one of $R^{c1}$s is a hydrogen atom or an acid dissociable group, $X^{c1}$ is an (n1+1)-valent nitrogen-containing heterocyclic group, and $X^{c3}$ is an (n2+1)-valent aromatic hydrocarbon group substituted with one or more electron withdrawing groups.)

In the formula (C1-5), each of n1 and n2 are preferably 1. In the formula (C1-5), it is preferred that $X^{c1}$ and a mercapto group are bonded to each other by a C—S bond, and $X^{c3}$ and a group represented by —CO—O—$R^{c1}$ are bonded to each other by a C—C bond.

Suitable specific examples of the mercapto compound represented by the above formula (C1-5) in which n1 and n2 are respectively 1 include the following compounds.

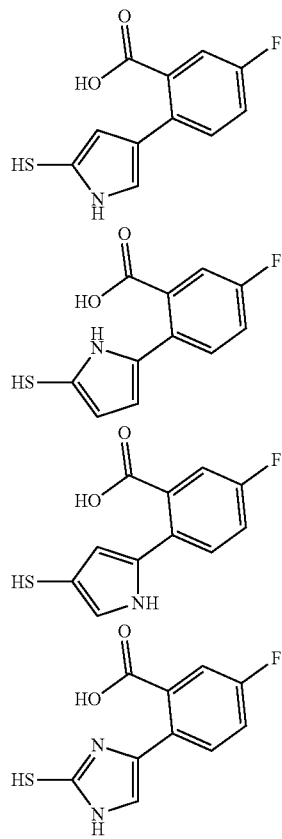

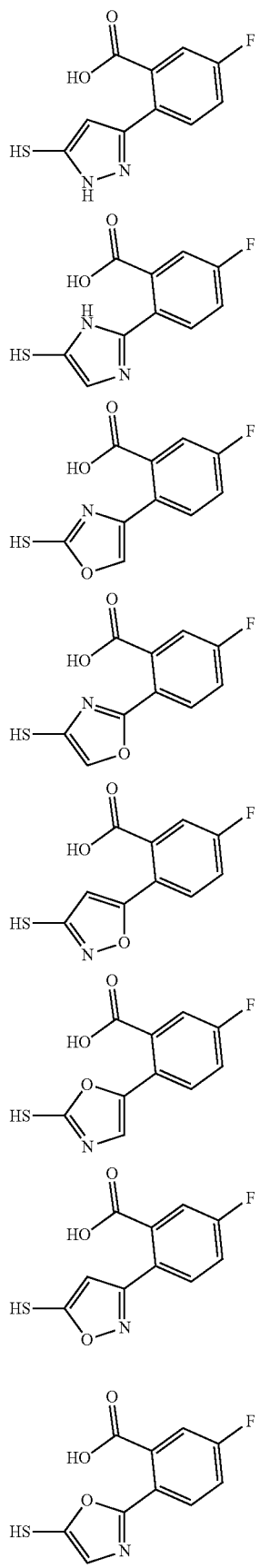
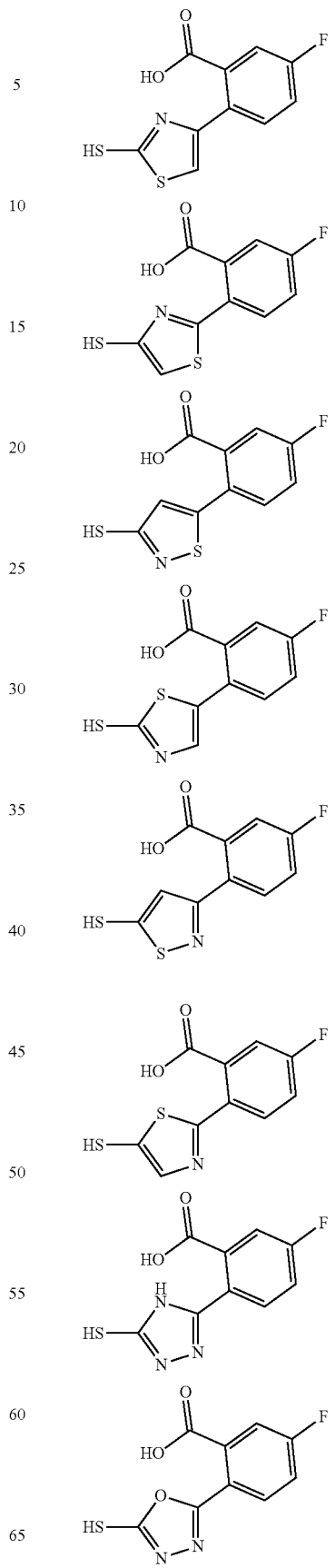

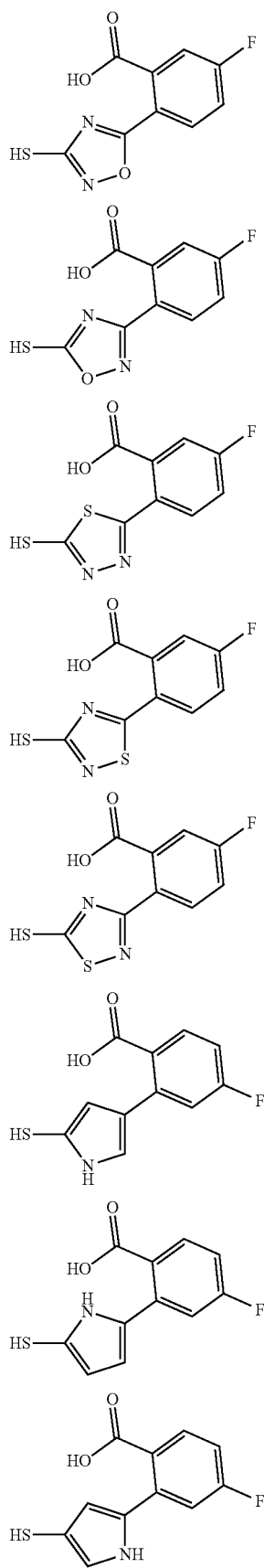
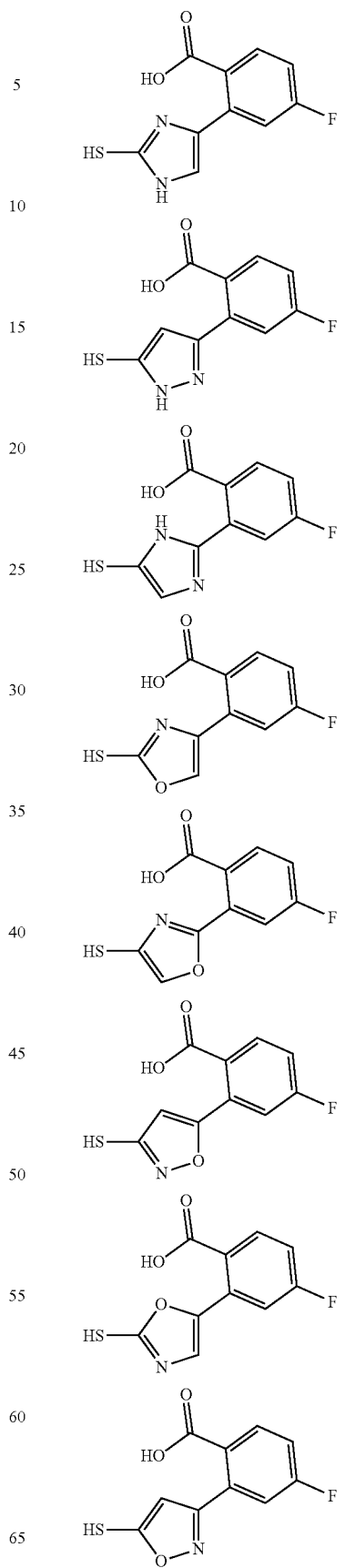

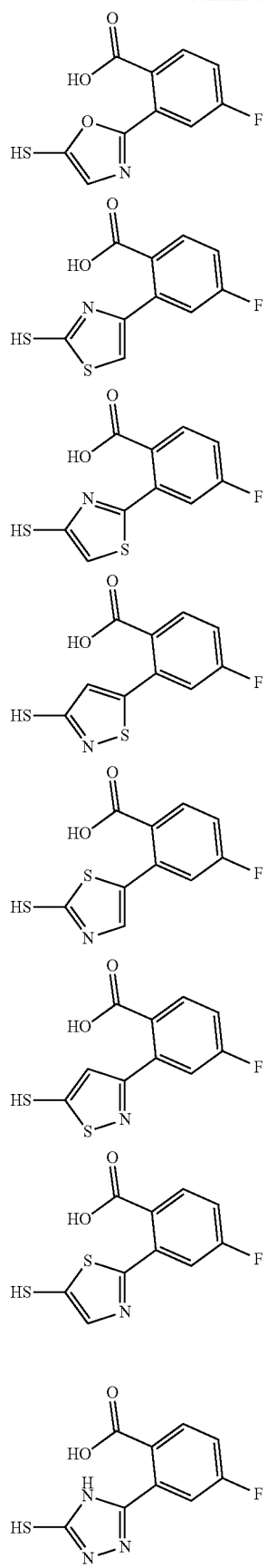
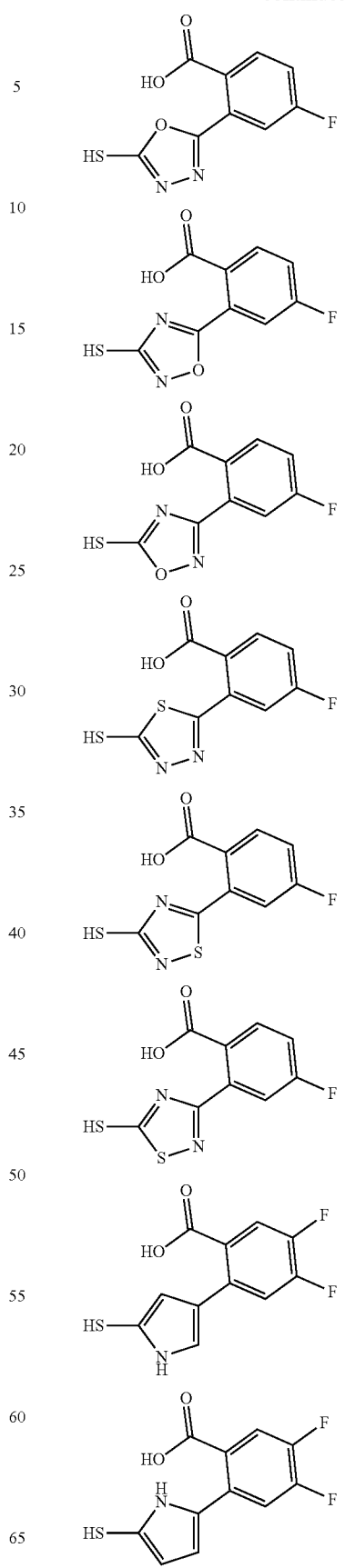

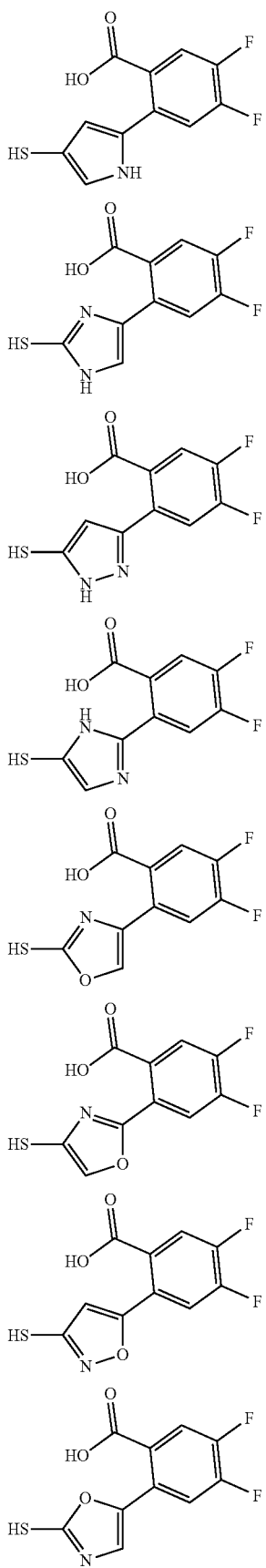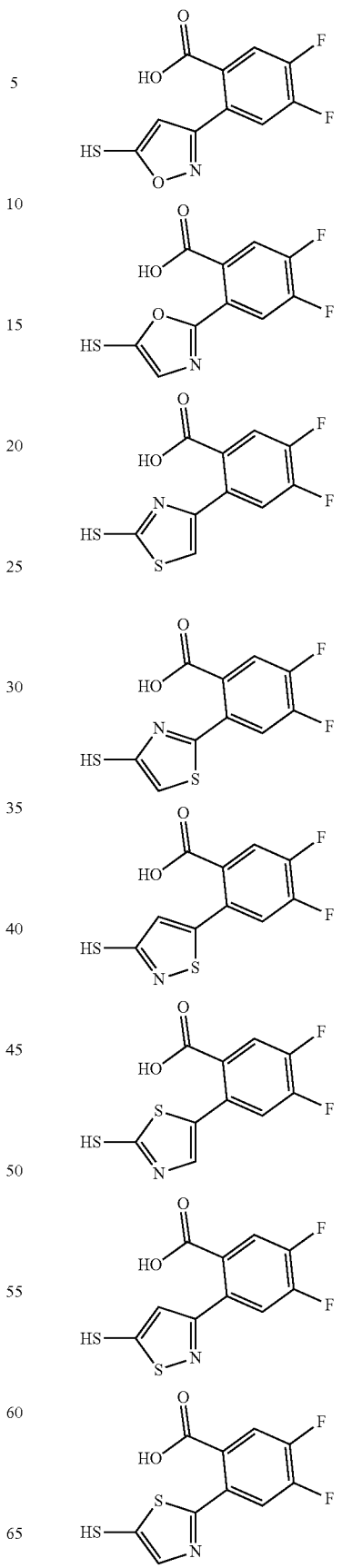

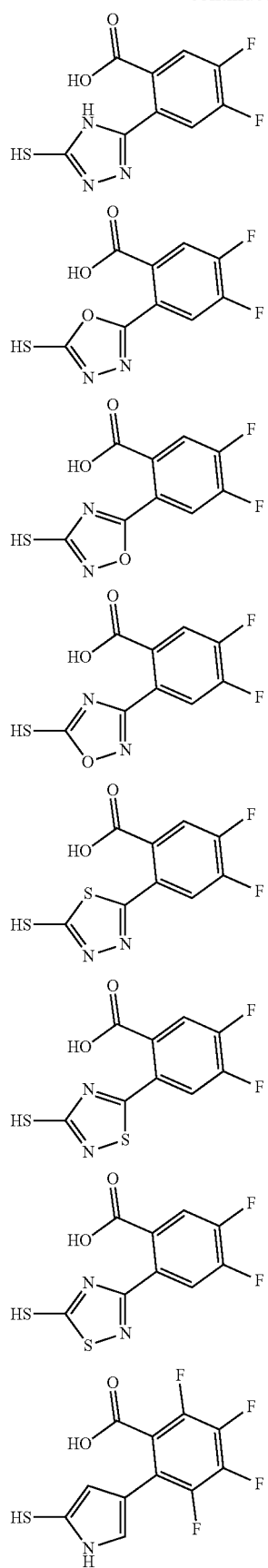
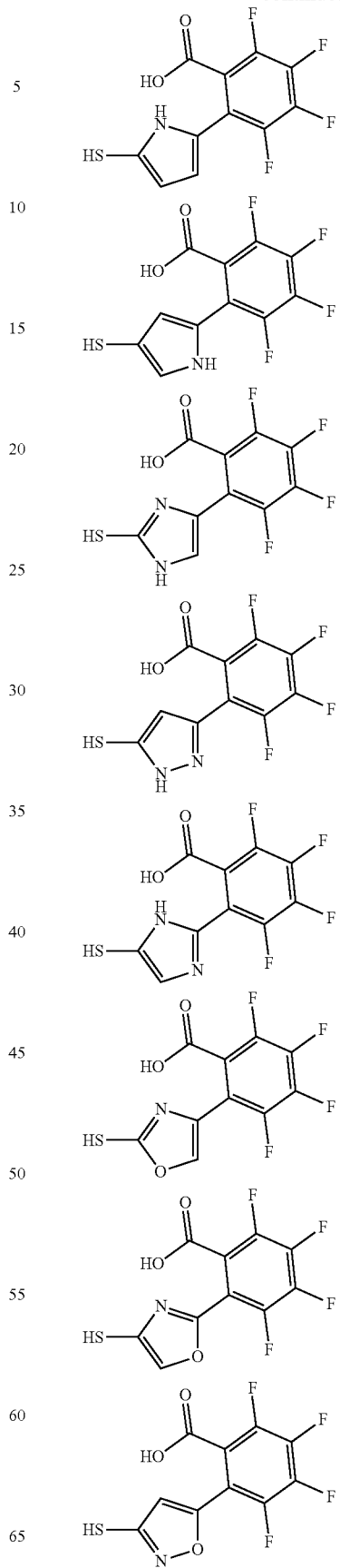

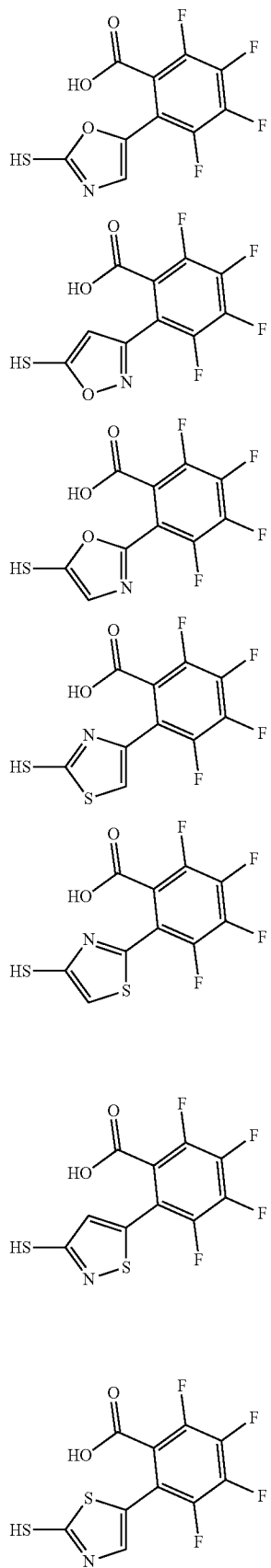
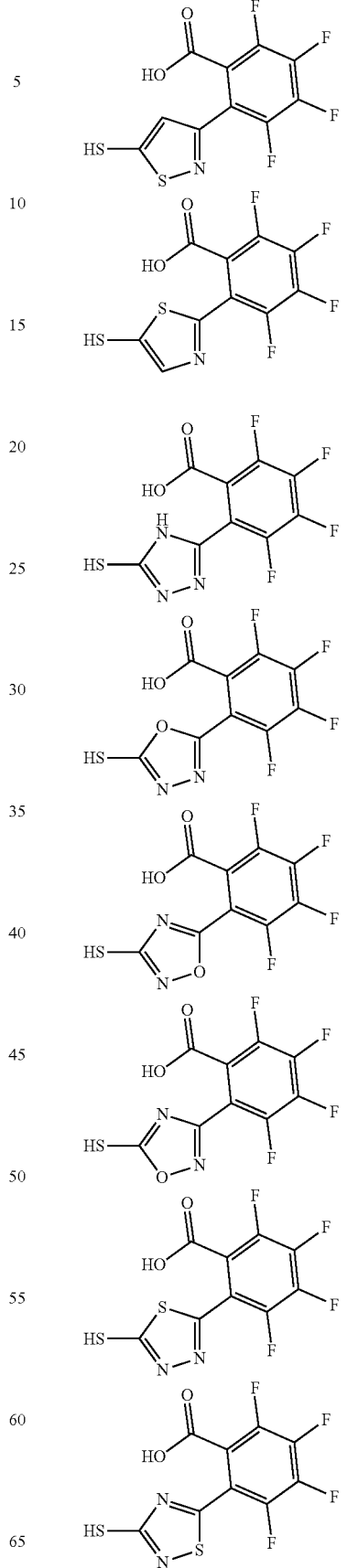

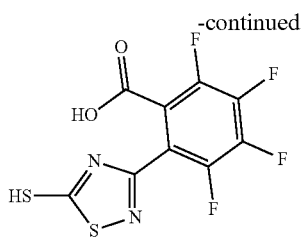

EXAMPLES

The present invention will be described in more detail below by way of Examples, but the present invention is not limited to these Examples.

Preparation Example 1

(Synthesis of Mercapto Compound C2)
In Preparation Example 1, a mercapto compound C2 having the following structure was synthesized.

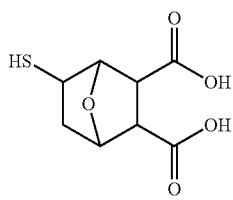

In a flask, 15.00 g of 7-oxanorborna-5-ene-2,3-dicarboxylic anhydride and 150.00 g of tetrahydrofuran were added, followed by stirring. Subsequently, 7.64 g of thioacetic acid (AcSH) was added in a flask, followed by stirring at room temperature for 3.5 hours. Then, the reaction solution was concentrated to obtain 22.11 g of 5-acetyl thio-7-oxanorbornane-2,3-dicarboxylic anhydride. In a flask, 22.11 g of 5-acetylthio-7-oxanorbornane-2,3-dicarboxylic anhydride and 30.11 g of an aqueous sodium hydroxide solution having the concentration of 10% by mass were added, and then contents in the flask were stirred at room temperature for 2 hours. Subsequently, hydrochloric acid (80.00 g) having the concentration of 20% by mass was added in the flask to acidify the reaction solution. Then, extraction with 200 g of ethyl acetate was performed four times to obtain an extraction liquid including a mercapto compound C2. The extraction liquid was concentrated and the collected residue was dissolved by adding 25.11 g of tetrahydrofuran (THF). Heptane was added dropwise to the THF solution to precipitate the mercapto compound C2, and the precipitated mercapto compound C2 was collected by filtration. The measurement results of $^1$H-NMR of the mercapto compound C2 are shown below.

$^1$H-NMR (DMSO-d6): δ12.10 (s, 2H), 4.72 (d, 1H), 4.43 (s, 1H), 3.10 (t, 1H), 3.01 (d, 1H), 2.85 (d, 1H), 2.75 (d, 1H), 2.10 (t, 1H), 1.40 (m, 1H)

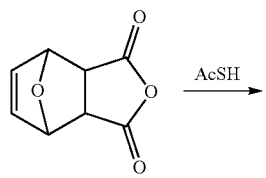

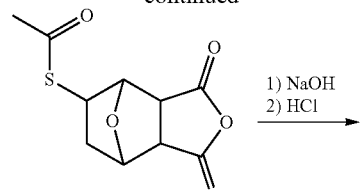

Preparation Example 2

(Synthesis of Mercapto Compound C3)
In Preparation Example 2, a mercapto compound C3 having the following structure was synthesized.

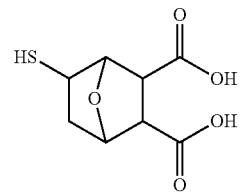 [SMILES: O=C(O)C1C2CC(S)C(O2)C1C(=O)O]

Mixture of the following compounds

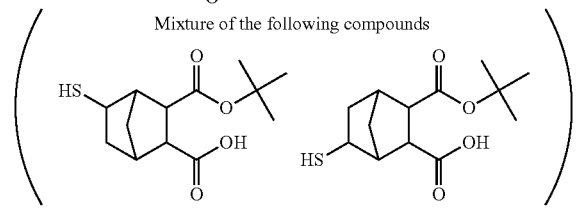

In a flask, 43.4 mL of lithium diisopropylamide (LDA)/n-hexane-tetrahydrofuran (THF) solution (1.13M, manufactured by Kanto Chemical Co., Inc.) was added, followed by cooling to −20° C. After cooling, a solution of 3.612 g of tert-butyl alcohol (tBuOH) and 36.00 g of THF was added dropwise in the flask over 20 minutes. After dropwise addition, contents in the flask were stirred for 30 minutes, and then a solution of 8.00 g of norborna-5-ene-2,3-dicarboxylic anhydride and 80 g of THF was added dropwise in the flask over 40 minutes. After raising the inner temperature of the flask to room temperature, contents in the flask were stirred for 4 hours. Then, 60 g of pure water was added in the flask, and the aqueous layer was collected by separation. The thus obtained aqueous layer was washed three times with tert-butyl methyl ether (TBME). To the thus washed aqueous layer, hydrochloric acid having the concentration of 10% by mass was added to adjust the pH to 1. Subsequently, extraction with 90 g of methylene chloride was performed three times and 2-tert-butoxycarbonyl-3-carboxynorborna-5-ene was extracted from the aqueous layer. After the extraction liquid was washed twice with 50 g of pure water, methylene chloride was distilled off from the extraction liquid to obtain 8.02 g of 2-tert-butoxycarbonyl-3-carboxynorborna-5-ene. After adding 8.02 g of 2-tert-butoxycarbonyl-3-carboxynorborna-5-ene, 6.98 g of thioacetic acid and 25 g of THF in the flask, contents in the flask were stirred at room temperature for 2 hours. Subsequently, the contents in the flask were concentrated. To the thus obtained concentrated liquid, 15.00 g of an aqueous sodium hydroxide solution having the concentration of 10% by mass was added, followed by stirring at room temperature for 2 hours. Then, 40.00 g of hydrochloric acid having the concentration of 20% by mass was added in the flask. Extraction with 100 g of ethyl acetate was performed four times to extract a mercapto compound C3 from the contents in the flask. Ethyl acetate was distilled off from the thus obtained extraction liquid to obtain 2.11 g of a mercapto compound C3 as an isomer mixture. The measurement results of $^1$H-NMR of the mercapto compound C3 are shown below.

$^1$H-NMR (DMSO-d6): δ11.34 (s, 1H), 3.00 (m, 1H), 2.65 (m, 1H), 2.56 (m, 1H), 2.44 (m, 1H), 1.82 (m, 1H), 1.79 (d, 1H), 1.73 (m, 2H), 1.43 (m, 2H), 1.40 (s, 9H)

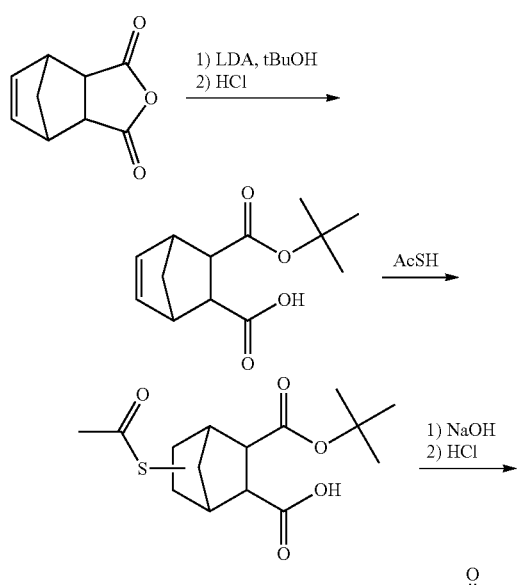

Preparation Example 3

(Synthesis of Mercapto Compound C4)

In Preparation Example 3, a mercapto compound C4 having the following structure was synthesized.

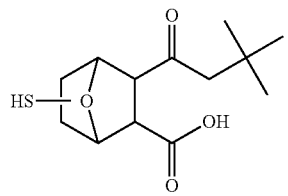

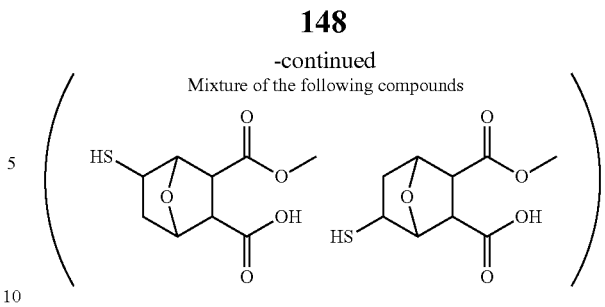

First, 5-acetyl thio-7-oxanorbornane-2,3-dicarboxylic anhydride was obtained in the same manner as in Preparation Example 1. In a flask, 10.00 g of 5-acetyl thio-7-oxanorbornane-2,3-dicarboxylic anhydride and 15.00 g of a solution having the concentration of 10% by mass (methanol/water=1/1) of sodium methoxide (NaOMe) were added, and then contents in the flask were stirred at room temperature for 2 hours. Subsequently, hydrochloric acid (40.00 g) having the concentration of 20% by mass was added in the flask to acidify the reaction solution. Then, extraction with 200 g of ethyl acetate was performed four times to obtain an extraction liquid including a mercapto compound C4. Ethyl acetate was distilled off from the extraction liquid to obtain 3.41 g of a mercapto compound C4 as an isomer mixture. The measurement results of $^1$H-NMR of the mercapto compound C4 are shown below.

$^1$H-NMR (DMSO-d6): δ12.00 (s, 1H), 4.68 (d, 1H), 4.06 (s, 1H), 3.67 (s, 3H), 3.34 (t, 1H), 2.99 (d, 1H), 2.90 (d, 1H), 2.75 (d, 1H), 2.07 (t, 1H), 1.70 (m, 1H)

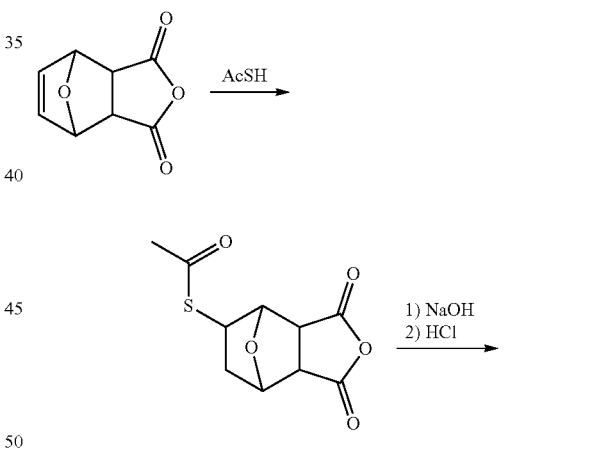

Preparation Example 4

(Synthesis of Mercapto Compound C5)

In Preparation Example 4, a mercapto compound C5 having the following structure was synthesized.

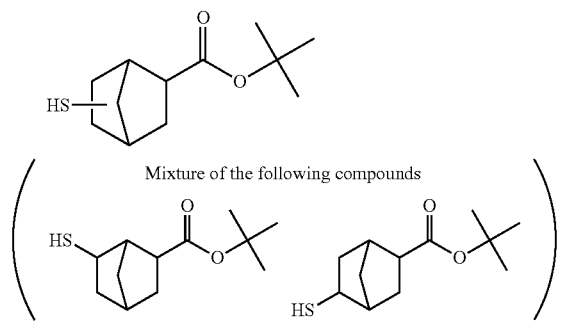

In a flask, 5.00 g of 2-tert-butoxycarbonylnorborn-5-ene and 5.00 g of tetrahydrofuran were added, followed by stirring. Subsequently, 9.79 g of thioacetic acid (AcSH) was added in the flask, followed by stirring at room temperature for 3.5 hours. Then, the reaction solution was concentrated to obtain 5.57 g of a mixture of 2-tert-butoxycarbonyl-5-acetylthionorbornane and 2-tert-butoxycarbonyl-6-acetyl-thionorbornane. In the flask, 5.00 g of the thus obtained and 15.00 g of an aqueous sodium hydroxide solution having the concentration of 10% by mass were added, and then contents in the flask were stirred at room temperature for 2 hours. Subsequently, hydrochloric acid (40.00 g) having the concentration of 20% by mass was added in the flask to acidify the reaction solution. Then, extraction with 100 g of ethyl acetate was performed four times to obtain an extraction liquid including a mercapto compound C5. Ethyl acetate was distilled off from the extraction liquid to obtain 3.76 g of a mercapto compound C5 as an isomer mixture. The measurement results of $^1$H-NMR of the mercapto compound C5 are shown below.

$^1$H-NMR (DMSO-d6): δ2.56 (m, 1H), 2.44 (m, 1H), 2.33 (m, 1H), 1.82 (m, 2H), 1.79 (d, 1H), 1.73 (m, 2H), 1.43 (m, 2H), 1.42 (s, 9H), 2.07 (t, 1H), 1.70 (m, 1H)

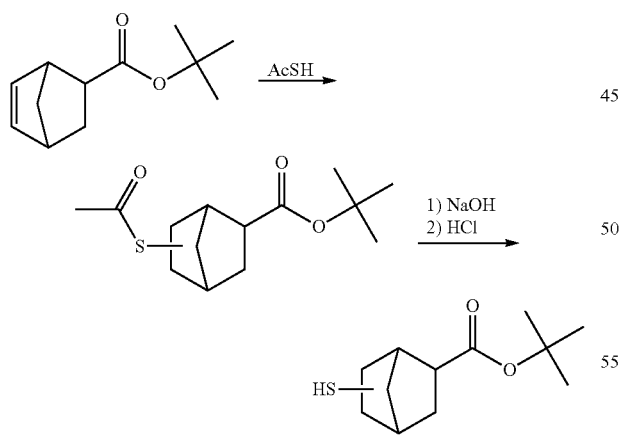

Examples 1 to 16, and Comparative Examples 1 to 10

In Examples 1 to 16 and Comparative Examples 1 to 10, the following compounds were used as the acid generator (A).

In Example 1 to 16, and Comparative Example 1 to 10, the following resins B1 and B2 were used as the resin whose solubility in alkali increases under the action of acid (resin (B)). The number at the lower right of the parentheses in each constituent unit in the following structural formula represents the content (% by mass) of the constituent unit in each resin. The resin B1 has a mass average molecular weight Mw of 40,000 and dispersibility (Mw/Mn) of 2.6. The resin B2 has a mass average molecular weight Mw of 40,000 and dispersibility (Mw/Mn) of 2.6.

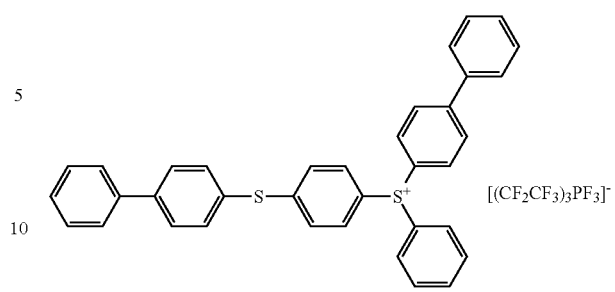

Resin B1

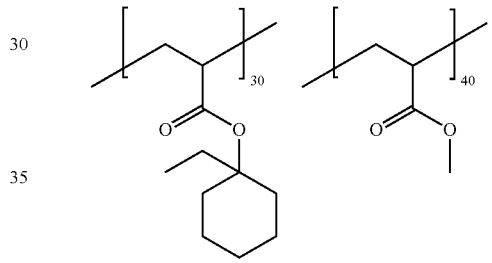

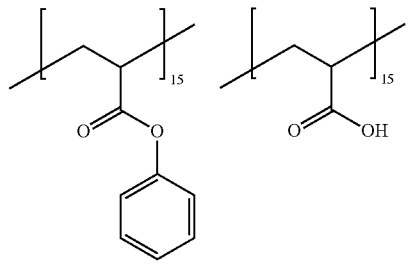

Resin B2

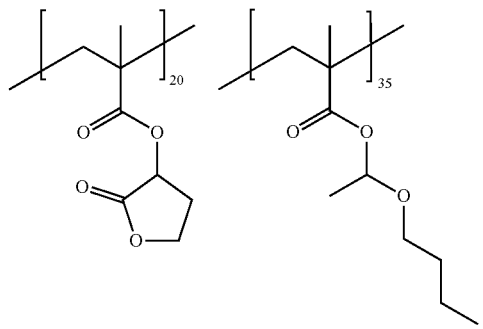

-continued

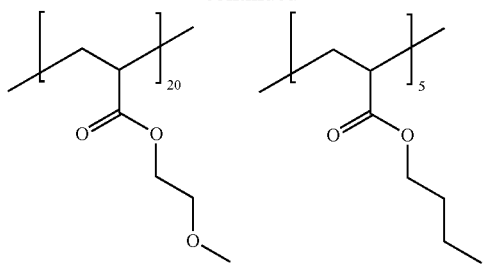

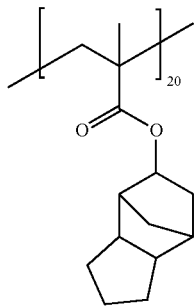

In Examples 1 to 16, the above-mentioned mercapto compounds C2 to C5 and the following C1 and C6 were used as the mercapto compound (C). The mercapto compound C1 was obtained in the same manner as in Preparation Example 1. Thiosalicylic acid, which is sold as a reagent, was used as the mercapto compound C6. In Comparative Examples 2 to 5 and Comparative Examples 7 to 10, 3-mercapto propionic acid was used as the mercapto compound C7, ethyl 3-mercapto propionate was used as the mercapto compound C8, and the following compounds were used as the mercapto compounds C9 and C10.

C1
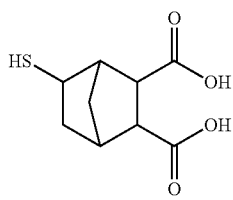

C6
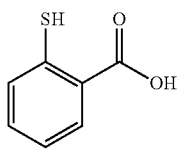

C9
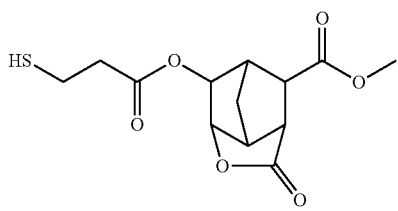

-continued

C10
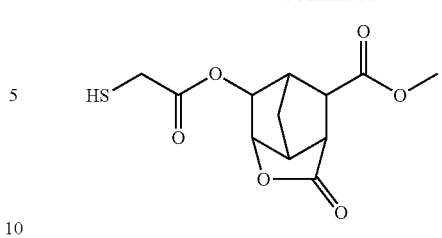

As the alkali-soluble resin (D), the following resins D1 and D2 were used. D1: polyhydroxystyrene resin (copolymer of p-hydroxystyrene:styrene=85:15 (mass ratio), mass average molecular weight (Mw): 2,500, dispersibility (Mw/Mn): 2.4) D2: novolac resin (m-cresol single condensate (mass average molecular weight (Mw): 8,000)

The resin (B), the mercapto compound (C) and the alkali soluble resin (D) in types and amounts shown in Table 1 as well as 2.0 parts by mass of the acid generator (A) and 0.02 part by mass of tripentyl amine were dissolved in methoxybutyl acetate such that the solid component concentration became 53% by mass to obtain photosensitive resin compositions of Examples and Comparative Examples.

Using the thus obtained photosensitive resin composition, footing, development residue and substrate modification were evaluated according to the following method. These evaluation results are shown in Table 1. Regarding Comparative Examples 3 to 5 and Comparative Examples 8 to 10, substrate modification was not evaluated for the following reasons. In Comparative Examples 3 to 5 and Comparative Examples 8 to 10, as shown in Table 1, residue was generated after development in the evaluation of development residue. If residue is generated on the substrate surface in the nonresist portion after development, it is difficult to confirm discoloration of the substrate surface by observation with an optical microscope.

[Evaluation of Footing]

Each of the photosensitive resin compositions of Examples and Comparative Examples was applied on a copper substrate having a diameter of 8 inches to form a photosensitive resin layer having a thickness of 55 μm. Then, the photosensitive resin layer was pre-baked at 100° C. for 5 minutes. After the pre-baking, using a mask having a square pattern with a diameter of 30 μm and an exposure device Prisma GHI (Ultratech Inc.), pattern exposure was performed with the ghi line at an exposure dose greater by 1.2 times than the minimum exposure dose capable of forming a pattern having a predetermined size. Subsequently, the substrate was placed on a hot plate and post-exposure baking (PEB) was performed at 100° C. for 3 minutes. Then, an aqueous 2.38% by weight solution of tetramethylammonium hydroxide (developing solution, NMD-3, manufactured by Tokyo Ohka Kogyo Co., Ltd.) was added dropwise to the exposed photosensitive resin layer, and allowed to stand at 23° C. for 60 seconds. This operation was repeated 4 times in total. Subsequently, the surface of the resist pattern was washed with running water, and blown with nitrogen to obtain a resist pattern. The cross-sectional shape of this resist pattern was observed by a scanning electron microscope to measure the amount of footing. Specifically, the amount of footing was measured by the following procedure. FIG. 1 shows a schematic diagram of a cross-section of a resist portion and a nonresist portion when measuring the amount of footing. In FIG. 1, a resist pattern having a resist portion 12 and a nonresist portion 13 (hole) is formed on a substrate 11. First, an inflexion point 15 at which footing on a side wall 14 starts was determined on the side wall 14 which is the interface between the resist portion 12 and the nonresist portion 13. A perpendicular line 16 was drawn down from the inflexion point 15 toward the surface of the substrate 11, and the intersection of the perpendicular line 16 and the surface of the substrate 11 was taken as a starting point of footing 17. Further, the intersection of the curve of the side wall 14 and the surface of the substrate 11 was taken as an endpoint of footing 18. A width Wf between the starting point of footing 17 and the endpoint of footing 18 defined in this way was taken as the amount of footing. The amount of footing is a value measured for any one of the side walls 14 at any one of the nonresist portions in the resist pattern. The degree of footing was evaluated in accordance with the following criteria based on the obtained value for the amount of footing.

<Criteria for Footing Evaluation>
O: 0 μm or more and 1.5 μm or less
Δ: more than 1.5 μm and 2.5 μm or less
X: more than 2.5 μm

[Evaluation of Development Residue]

With respect to the resist pattern formed in the evaluation of footing, it was confirmed whether or not development residue exists on a surface of a copper substrate exposed at a nonresist portion by an optical microscope. The case where no development residue existed was rated "O", whereas, the case where development residue existed was rated "X".

[Evaluation of Substrate Modification]

A resist pattern was formed in the same manner as in the evaluation of footing, except that the photosensitive resin layer is not formed on a part of the copper substrate. A comparison was made between hue of the copper substrate at the nonresist portion in the resist pattern and hue of the position where the photosensitive resin layer on the copper substrate was not formed, using an optical microscope. The case where clear difference between both hues is not recognized was rated "O", whereas, the case where clear difference between both hues is recognized was rated "X".

TABLE 1

| | Resin (B) Types/ Parts by mass | Alkali soluble resin (D) Types/ Parts by mass | Mercapto compound (C) Types/ Parts by mass | Footing | Development residue | Substrate modification |
|---|---|---|---|---|---|---|
| Example 1 | B1/40 | D1/20 | C1/0.05 | O | O | O |
| Example 2 | | D2/40 | C1/0.10 | O | O | O |
| Example 3 | | | C2/0.05 | O | O | O |
| Example 4 | | | C2/0.10 | O | O | O |
| Example 5 | | | C3/0.10 | O | O | O |
| Example 6 | | | C4/0.10 | O | O | O |
| Example 7 | | | C5/0.10 | O | O | O |
| Example 8 | | | C6/0.10 | O | O | O |
| Example 9 | B2/100 | — | C1/0.05 | O | O | O |
| Example 10 | | | C1/0.10 | O | O | O |
| Example 11 | | | C2/0.05 | O | O | O |
| Example 12 | | | C2/0.10 | O | O | O |
| Example 13 | | | C3/0.10 | O | O | O |
| Example 14 | | | C4/0.10 | O | O | O |
| Example 15 | | | C5/0.10 | O | O | O |
| Example 16 | | | C6/0.10 | O | O | O |
| Comparative Example 1 | B1/40 | D1/20 D2/40 | — | X | O | O |
| Comparative Example 2 | | | C7/0.05 | X | O | X |
| Comparative Example 3 | | | C8/0.05 | X | X | — |
| Comparative Example 4 | | | C9/0.05 | O | X | — |
| Comparative Example 5 | | | C10/0.05 | O | X | — |
| Comparative Example 6 | B2/100 | — | — | X | O | O |
| Comparative Example 7 | | | C7/0.05 | X | O | X |
| Comparative Example 8 | | | C8/0.05 | X | X | — |
| Comparative Example 9 | | | C9/0.05 | O | X | — |
| Comparative Example 10 | | | C10/0.05 | O | X | — |

As is apparent from Examples 1 to 16, when a resist pattern is formed using a positive-type photosensitive resin composition including the acid generator (A) which generates acid upon exposure to an irradiated active ray or radiation and the resin (B) whose solubility in alkali increases under the action of acid as well as the mercapto compound (C) represented by the above formula (C1), the occurrence of footing and the generation of development residue are suppressed in the resist pattern, and modification of a metal substrate does not easily occur.

Meanwhile, as is apparent from Comparative Examples 1 to 10, when the mercapto compound (C) having a structure represented by the formula (C1) is not included in the positive-type photosensitive resin composition, and a mercapto compound having a structure other than the structure represented by the formula (C1) is included, it is difficult to suppress the occurrence of footing, and development residue may be generated and modification of a metal substrate may occur.

Examples 17 to 22, and Comparative Examples 11 to 15

In Examples 17 to 22, and Comparative Examples 11 to 15, a compound of the following formula was used as the acid generator (A).

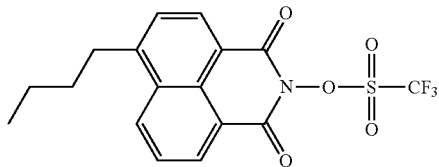 [SMILES: CCCCc1ccc2c3c(cccc13)C(=O)N(OS(=O)(=O)C(F)(F)F)C2=O]

In Examples 17 to 22 and Comparative Examples 11 to 15, the following resin 3 was used as the resin whose solubility in alkali increases under the action of acid (resin (B)). The number at the lower right of the parentheses in each constituent unit in the following structural formula represents the content (% by mass) of the constituent unit in each resin. The resin B3 has a number average molecular weight Mn of 103,000.

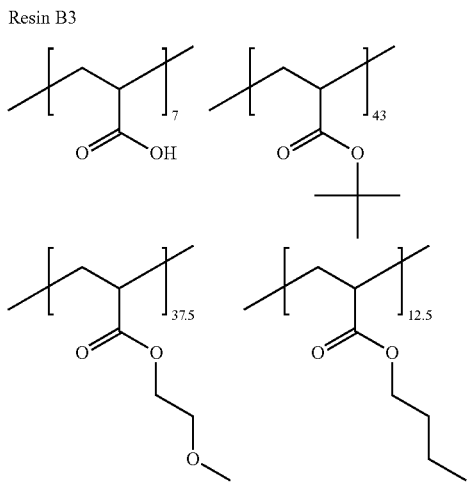

In Examples 17 to 22, the above-mentioned mercapto compounds C1 to C6 were used as the mercapto compound (C). In Comparative Examples 12 to 15, the above-mentioned mercapto compounds C7 to C10 were used.

The following resins D3, D4 and D5 were used as an alkali soluble resin (D). D3: polyhydroxystyrene resin (co-polymer of p-hydroxystyrene:styrene:tert-butyl acrylate=60: 15:25 (mass ratio), mass average molecular weight (Mw): 10,000)
D4: novolac resin (co-condensate obtained by condensing m-cresol and p-cresol with formaldehyde (m-cresol/p-cresol=40/60 (mass ratio)), mass average molecular weight (Mw): 5,000)
D5: novolac resin (co-condensate obtained by condensing m-cresol and p-cresol with formaldehyde (m-cresol/p-cresol=40/60 (mass ratio)), mass average molecular weight (Mw): 7,000)

The resin (B), the mercapto compound (C) and the alkali soluble resin (D) in types and amounts shown in Table 2 as well as 1.0 parts by mass of the acid generator (A) and 0.05 part by mass of the surfactant (BYK310, manufactured by BYK) were dissolved in a mixed solvent of methoxybutyl acetate (60% by mass) and propylene glycol monomethyl ether acetate (40% by mass) such that the solid component concentration became 40% by mass to obtain photosensitive resin compositions of Examples 17 to 22 and Comparative Examples 11 to 15.

Using the thus obtained photosensitive resin composition, footing, development residue and substrate modification were evaluated according to the following method. These evaluation results are shown in Table 2. In Comparative Examples 12 to 15, since residue was generated after development in the evaluation of development residue, substrate modification was not evaluated.
[Evaluation of Footing]

Each of the photosensitive resin compositions of Examples and Comparative Examples was applied on a copper substrate having a diameter of 8 inches to form a photosensitive resin layer having a film thickness of 11 μm. Then, the photosensitive resin layer was pre-baked at 130° C. for 5 minutes. After the pre-baking, using a mask having a line-and-space pattern with a line width of 5 μm and space width of 5 μm and an exposure device Prisma GHI (Ultratech Inc.), pattern exposure was performed with the ghi line at an exposure dose greater by 1.2 times than the minimum exposure dose capable of forming a pattern having a predetermined size. Subsequently, the substrate was placed on a hot plate and post-exposure baking (PEB) was performed at 90° C. for 1.5 minutes. Then, an aqueous 2.38% by weight solution of tetramethylammonium hydroxide (developing solution, NMD-3, manufactured by Tokyo Ohka Kogyo Co., Ltd.) was added dropwise to the exposed photosensitive resin layer, and allowed to stand at 23° C. for 30 seconds. This operation was repeated twice in total. Subsequently, the surface of the resist pattern was washed with running water, and blown with nitrogen to obtain a resist pattern. The cross-sectional shape of this resist pattern was observed by a scanning electron microscope to measure the amount of footing in the same manner as in Examples 1 to 16 and Comparative Examples 1 to 6. The degree of footing was evaluated in accordance with the following criteria based on the obtained value for the amount of footing.
<Criteria for Footing Evaluation>
O: 0 μm or more and 0.5 μm or less
Δ: more than 0.5 μm and 1.0 μm or less
X: more than 1.0 μm
[Evaluation of Development Residue]

With respect to the resist pattern formed in the evaluation of footing, it was confirmed whether or not development residue exists on a surface of a copper substrate exposed at a nonresist portion by an optical microscope. The case where no development residue existed was rated "O", whereas, the case where development residue existed was rated "X".
[Evaluation of Substrate Modification]

A resist pattern was formed in the same manner as in the evaluation of footing, except that the photosensitive resin layer is not provided on a part of the copper substrate. A comparison was made between hue of the copper substrate at the nonresist portion in the resist pattern and hue of the position where the photosensitive resin layer on the copper substrate was not formed, using an optical microscope. The case where clear difference between both hues is not recognized was rated "O", whereas, the case where clear difference between both hues is recognized was rated "X".

TABLE 2

|  | Resin (B) Types/ Parts by mass | Alkali soluble resin (D) Types/ Parts by mass | Mercapto compound (C) Types/ Parts by mass | Footing | Development residue | Substrate modification |
|---|---|---|---|---|---|---|
| Example 17 | B3/35 | D3/10 | C1/0.10 | ○ | ○ | ○ |
| Example 18 |  | D4/27.5 | C2/0.10 | ○ | ○ | ○ |
| Example 19 |  | D5/27.5 | C3/0.10 | ○ | ○ | ○ |
| Example 20 |  |  | C4/0.10 | ○ | ○ | ○ |
| Example 21 |  |  | C5/0.10 | ○ | ○ | ○ |
| Example 22 |  |  | C6/0.10 | ○ | ○ | ○ |
| Comparative Example 11 |  |  | — | X | ○ | ○ |
| Comparative Example 12 |  |  | C7/0.10 | X | ○ | X |
| Comparative Example 13 |  |  | C8/0.10 | X | X | — |
| Comparative Example 14 |  |  | C9/0.10 | ○ | X | — |
| Comparative Example 15 |  |  | C10/0.10 | ○ | X | — |

As is apparent from Examples 17 to 22, even if the types of the resin (B), the types of the alkali soluble resin (D) and the thickness of the coated film during patterning are changed from those in Examples 1 to 16, when a resist pattern is formed using a positive-type photosensitive resin composition including the acid generator (A) which generates acid upon exposure to an irradiated active ray or radiation and the resin (B) whose solubility in alkali increases under the action of acid as well as the mercapto compound (C) represented by the above formula (C1), the occurrence of footing and the generation of development residue are suppressed in the resist pattern, and modification of a metal substrate does not easily occur.

Preparation Example 5

(Synthesis of Mercapto Compound C11)

In Preparation Example 5, a mercapto compound C11 having the following structure was synthesized.

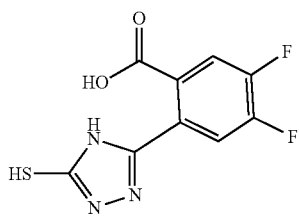 [SMILES: O=C(O)c1cc(F)c(F)cc1-c1nnc(S)[nH]1]

In a flask, 53.00 g of 4,5-difluorophthalic anhydride, 2.72 g of thiocarbamide and 50 g of acetonitrile were added, followed by stirring. Subsequently, the temperature of a suspension in the flask was raised to 85° C. and the suspension was stirred at the same temperature for 5 hours. Then, the suspension was cooled to room temperature and the solid was collected by filtration to obtain 5.31 g of an intermediate. The thus obtained intermediate was dissolved in an aqueous sodium hydroxide solution having the concentration of 20% by mass, and then the temperature of the thus obtained solution was raised to 100° C. The reaction solution was stirred for 6 hours and then cooled to room temperature. Subsequently, the pH of the reaction solution was adjusted to 1 with a hydrochloric acid solution having the concentration of 20% by mass to precipitate a product. The thus precipitated product was obtained by filtration and then dried to obtain 4.10 g of a mercapto compound C11. The product was subjected to LC/MS analysis (liquid chromatography-mass spectrometry). As a result, the analysis results corresponded with the molecular weight of the mercapto compound C11.

(m/z=258.01: [M+H]⁺, m/z=256.01: [M−H]⁻)

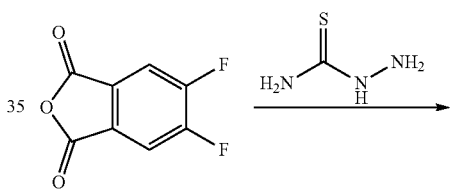

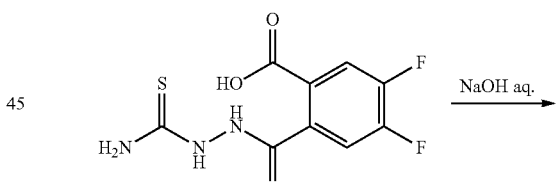

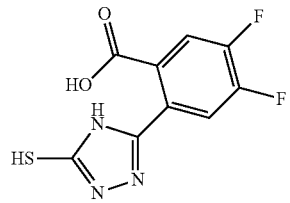

Preparation Example 6

(Synthesis of Mercapto Compound C12)

In Preparation Example 6, a mercapto compound C12 having the following structure was synthesized.

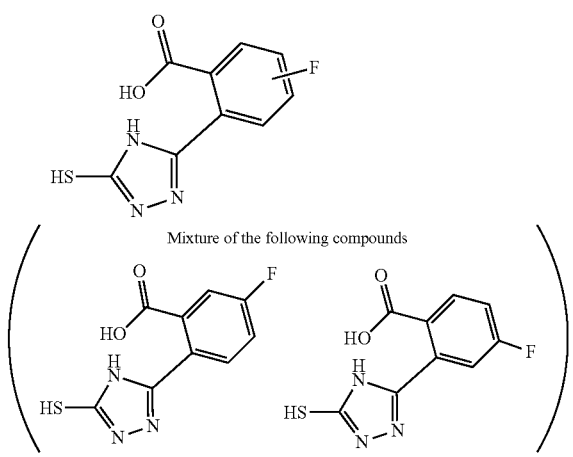

Mixture of the following compounds

In the same manner as in Preparation Example 5, except that 4,5-difluorophthalic anhydride was changed to 4-fluorophthalic anhydride, a mercapto compound C12 was obtained. The product was subjected to LC/MS analysis (liquid chromatography-mass spectrometry). As a result, the analysis results corresponded with the molecular weight of the mercapto compound C12.

(m/z=240.02: [M+H]$^+$, m/z=238.01: [M−H]$^+$)

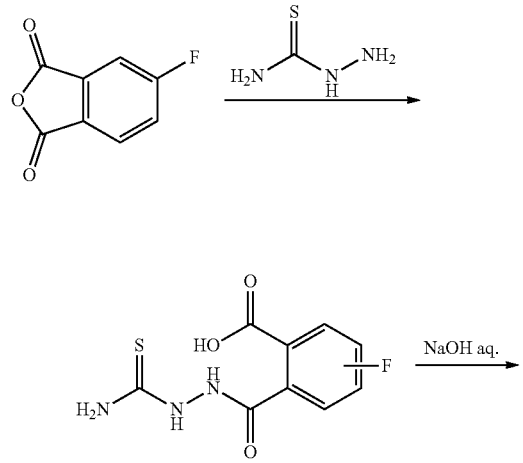

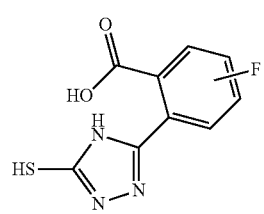

Preparation Example 7

(Synthesis of Mercapto Compound C13)

In Preparation Example 7, a mercapto compound C13 having the following structure was synthesized.

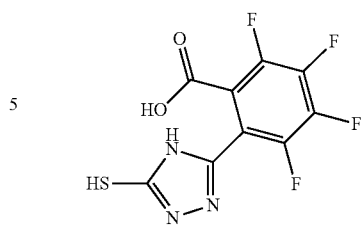

In the same manner as in Preparation Example 5, except that 4,5-difluorophthalic anhydride was changed to 3,4,5,6-tetrafluorophthalic anhydride, a mercapto compound C13 was obtained. The product was subjected to LC/MS analysis (liquid chromatography-mass spectrometry). As a result, the analysis results corresponded with the molecular weight of the mercapto compound C13.

(m/z=294.00: [M+H]$^+$, m/z=292.00: [M−H]$^-$)

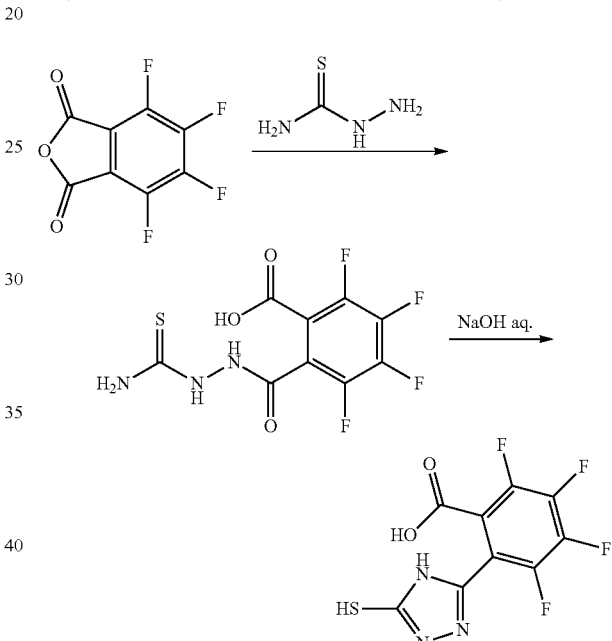

Examples 23 to 58, Comparative Example 16, and Comparative Example 17

In Examples 23 to 58, Comparative Example 16 and Comparative Example 17, the mercapto compounds C11 to C13 obtained in Preparation Examples 5 to 7, the following mercapto compounds C14 to C18, and the above mercapto compound C1 were used as the mercapto compound (C). With respect to components other than the mercapto compound (C), the materials used in Examples 1 to 22 and Comparative Examples 1 to 15 were used.

C14

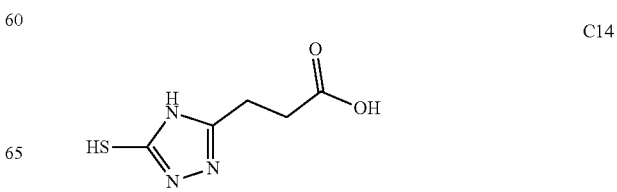

-continued

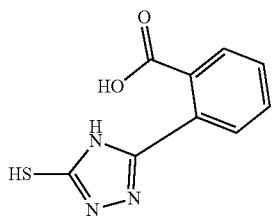
C15

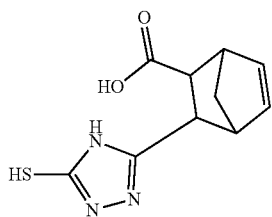
C16

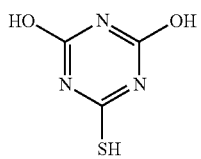
C17

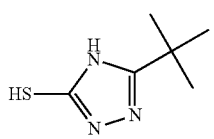
C18

The resin (B), the mercapto compound (C) and the alkali soluble resin (D) in types and amounts shown in Tables 3 and 4 as well as 4.0 parts by mass of the acid generator (A) which is the same as that used in Example 1, 0.2 part by mass of tripentylamine and 0.05 part by mass of the surfactant (BYK310, manufactured by BYK) were dissolved in a mixed solvent of methoxybutyl acetate (60% by mass) and propylene glycol monomethyl ether acetate (40% by mass) such that the solid content concentration became 40% by mass to obtain photosensitive resin compositions of Examples 23 to 58, Comparative Example 16 and Comparative Example 17.

The footing was evaluated according to the following method using the thus obtained photosensitive resin composition and the development residue was evaluated in the same manner as in Example 1. These evaluation results are shown in Tables 3 and 4.

[Evaluation of Footing]

The photosensitive resin compositions from Examples and Comparative Examples were each applied on a copper substrate with a diameter of 8 inches to form a photosensitive resin layer having a thickness of 7 μm. Then, the photosensitive resin layers were pre-baked at 130° C. for 5 minutes. After the pre-baking, using a mask having a line-and-space pattern with a line width of 2 μm and space width of 2 μm and an exposure device Prisma GHI (Ultratech Inc.), pattern exposure was performed with the ghi line at an exposure dose greater by 1.2 times than the minimum exposure dose capable of forming a pattern having a predetermined size. Subsequently, the substrate was placed on a hot plate and post-exposure baking (PEB) was performed at 90° C. for 1.5 minutes. Then, an aqueous 2.38% by weight solution of tetramethylammonium hydroxide (developing solution, NMD-3, produced by Tokyo Ohka Kogyo Co., Ltd.) was added dropwise to the exposed photosensitive resin layer, and allowed to stand at 23° C. for 30 seconds. This operation was repeated twice in total. Subsequently, the surface of the resist pattern was washed with running water, and blown with nitrogen to obtain a resist pattern. The cross-sectional shape of this resist pattern was observed under a scanning electron microscope to measure the amount of footing in the same manner as in Example 1. The degree of footing was evaluated in accordance with the following criteria based on the obtained value for the amount of footing.

<Evaluation Criteria of Footing>

◯: 0 μm or more and 1.5 μm or less

Δ: more than 0.5 μm and 1.0 μm or less

X: more than 1.0 μm

TABLE 3

| | Resin(B) Types/ Parts by mass | Alkali soluble resin(D) Types/ Parts by mass | Mercapto compound(C) Types/ Parts by mass | Footing | Development residue |
|---|---|---|---|---|---|
| Example 23 | B1/40 | D1/20 | C11/0.10 | ◯ | ◯ |
| Example 24 | | D2/40 | C12/0.10 | ◯ | ◯ |
| Example 25 | | | C13/0.10 | ◯ | ◯ |
| Example 26 | | | C11/0.10 C1/0.10 | ◯ | ◯ |
| Example 27 | | | C12/0.10 C1/0.10 | ◯ | ◯ |
| Example 28 | | | C13/0.10 C1/0.10 | ◯ | ◯ |
| Example 29 | | | C11/0.10 C17/0.10 | ◯ | ◯ |
| Example 30 | | | C12/0.10 C17/0.05 | ◯ | ◯ |
| Example 31 | | | C13/0.10 C17/0.05 | ◯ | ◯ |
| Example 32 | | | C14/0.10 | ◯ | ◯ |
| Example 33 | | | C15/0.10 | ◯ | ◯ |
| Example 34 | | | C16/0.10 | ◯ | ◯ |
| Example 35 | | | C14/0.10 C1/0.10 | ◯ | ◯ |
| Example 36 | | | C15/0.10 C1/0.10 | ◯ | ◯ |
| Example 37 | | | C16/0.10 C1/0.10 | ◯ | ◯ |
| Example 38 | | | C14/0.10 C17/0.05 | ◯ | ◯ |
| Example 39 | | | C15/0.10 C17/0.05 | ◯ | ◯ |
| Example 40 | | | C16/0.10 C17/0.10 | ◯ | ◯ |
| Comparative Example 16 | | | C18/0.10 | X | X |

TABLE 4

| | Resin(B) Types/ Parts by mass | Alkali soluble resin(D) Types/ Parts by mass | Mercapto compound(C) Types/ Parts by mass | Footing | Development residue |
|---|---|---|---|---|---|
| Example 41 | B2/100 | — | C11/0.10 | ◯ | ◯ |
| Example 42 | | | C12/0.10 | ◯ | ◯ |
| Example 43 | | | C13/0.10 | ◯ | ◯ |
| Example 44 | | | C11/0.10 C1/0.10 | ◯ | ◯ |
| Example 45 | | | C12/0.10 C1/0.10 | ◯ | ◯ |
| Example 46 | | | C13/0.10 C1/0.10 | ◯ | ◯ |

TABLE 4-continued

| | Resin(B) Types/ Parts by mass | Alkali soluble resin(D) Types/ Parts by mass | Mercapto compound(C) Types/ Parts by mass | Footing | Development residue |
|---|---|---|---|---|---|
| Example 47 | | | C11/0.10<br>C17/0.10 | ○ | ○ |
| Example 48 | | | C12/0.10<br>C17/0.05 | ○ | ○ |
| Example 49 | | | C13/0.10<br>C17/0.05 | ○ | ○ |
| Example 50 | | | C14/0.10 | ○ | ○ |
| Example 51 | | | C15/0.10 | ○ | ○ |
| Example 52 | | | C16/0.10 | ○ | ○ |
| Example 53 | | | C14/0.10<br>C1/0.10 | ○ | ○ |
| Example 54 | | | C15/0.10<br>C1/0.10 | ○ | ○ |
| Example 55 | | | C16/0.10<br>C1/0.10 | ○ | ○ |
| Example 56 | | | C14/0.10<br>C17/0.05 | ○ | ○ |
| Example 57 | | | C15/0.10<br>C17/0.05 | ○ | ○ |
| Example 58 | | | C16/0.10<br>C17/0.10 | ○ | ○ |
| Comparative Example 17 | | | C18/0.10 | X | X |

As is apparent from Examples 23 to 58, when the resist pattern is formed using a positive-type photosensitive resin composition including the acid generator (A) which generates acid upon exposure to an irradiated active ray or radiation and the resin (B) whose solubility in alkali increases under the action of acid as well as the mercapto compound (C) represented by the aforementioned formula (C1), the occurrence of footing and the generation of development residue are suppressed in the resist pattern.

Meanwhile, as is apparent from Comparative Examples 16 and 17, when only a mercapto compound (C) having a structure other than the structure represented by the formula (C1) is included in the positive-type photosensitive resin composition, it is difficult to suppress the occurrence of footing, and development residue may be generated.

Examples 59 to 76, and Comparative Example 18

In Examples 59 to 76 and Comparative Example 18, the mercapto compound C1 and the mercapto compounds C11 to C18 used in Examples 23 to 58, Comparative Example 16 and Comparative Example 17 were used as the mercapto compound (C). In Examples 59 to 76 and Comparative Example 18, the resin B3 used in Example 17 was used as the resin (B). In Examples 59 to 76 and Comparative Example 18, the acid generator, which is the same as that used in Example 17, was used as the acid generator (A). With respect to materials other than the acid generator (A), the resin (B) and the mercapto compound (C), the materials used in Examples 1 to 22 and Comparative Examples 1 to 15 were used.

The resin (B), the mercapto compound (C) and the alkali soluble resin (D) in types and amounts shown in Table 5 as well as 1.0 parts by mass of the acid generator (A) which is the same as that used in Example 17, 0.2 part by mass of the acid diffusion suppressing agent (E) (LA63P, manufactured by ADEKA Corporation) and 0.05 part by mass of the surfactant (BYK310, manufactured by BYK) were dissolved in a mixed solvent of methoxybutyl acetate (60% by mass) and propylene glycol monomethyl ether acetate (40% by mass) such that the solid component concentration became 40% by mass to obtain photosensitive resin compositions of Examples 59 to 76 and Comparative Example 18.

Using the thus obtained photosensitive resin compositions, footing and development residue were evaluated in the same manner as in Example 1. These evaluation results are shown in Table 5.

TABLE 5

| | Resin(B) Types/ Parts by mass | Alkali soluble resin(D) Types/ Parts by mass | Mercapto compound(C) Types/ Parts by mass | Footing | Development residue |
|---|---|---|---|---|---|
| Example 59 | B1/35 | D1/10 | C11/0.10 | ○ | ○ |
| Example 60 | | D2/55 | C12/0.10 | ○ | ○ |
| Example 61 | | | C13/0.10 | ○ | ○ |
| Example 62 | | | C11/0.10<br>C1/0.10 | ○ | ○ |
| Example 63 | | | C12/0.10<br>C1/0.10 | ○ | ○ |
| Example 64 | | | C13/0.10<br>C1/0.10 | ○ | ○ |
| Example 65 | | | C11/0.10<br>C17/0.10 | ○ | ○ |
| Example 66 | | | C12/0.10<br>C17/0.05 | ○ | ○ |
| Example 67 | | | C13/0.10<br>C17/0.05 | ○ | ○ |
| Example 68 | | | C14/0.10 | ○ | ○ |
| Example 69 | | | C15/0.10 | ○ | ○ |
| Example 70 | | | C16/0.10 | ○ | ○ |
| Example 71 | | | C14/0.10<br>C1/0.10 | ○ | ○ |
| Example 72 | | | C15/0.10<br>C1/0.10 | ○ | ○ |
| Example 73 | | | C16/0.10<br>C1/0.10 | ○ | ○ |
| Example 74 | | | C14/0.10<br>C17/0.05 | ○ | ○ |
| Example 75 | | | C15/0.10<br>C17/0.05 | ○ | ○ |
| Example 76 | | | C16/0.10<br>C17/0.10 | ○ | ○ |
| Comparative Example 18 | | | C18/0.10 | X | X |

As is apparent from Examples 59 to 76, when a resist pattern is formed using a positive-type photosensitive resin composition including the acid generator (A) which generates acid upon exposure to an irradiated active ray or radiation and the resin (B) whose solubility in alkali increases under the action of acid as well as the mercapto compound (C) represented by the above formula (C1), the occurrence of footing and the generation of development residue are suppressed in the resist pattern.

Meanwhile, as is apparent from Comparative Example 18, when only a mercapto compound (C) having a structure other than the structure represented by the formula (C1) is included in the positive-type photosensitive resin composition, it is difficult to suppress the occurrence of footing, and development residue may be generated.

Example 77, and Comparative Example 19

With respect to the positive-type photosensitive resin compositions of Example 1 and Comparative Example 3, a plated article was formed using, as a template, a square pattern having a film thickness of 55 μm and a diameter of 30 μm used for evaluation of footing. A test using the positive-type photosensitive resin composition of Example 1 was taken as Example 77, and a test using the positive-type photosensitive resin composition of Comparative Example 3 was taken as Comparative Example 19. Before formation of the plated article, a surface treatment to the copper substrate was not particularly preformed.

Specifically, using a copper sulfate plating solution, plating was performed under the conditions of a liquid temperature of 25° C. and a cathode current density of 5ASD (A/dm$^2$) until the height of plating reached 50 μm to form a cuboid plated article on a surface made of copper in the substrate. After formation of the plated article, the plated article was rinsed with acetone to peel off a resist pattern used as the template for formation of the plated article. After peeling the resist pattern, the surface of the substrate was observed by an electron microscope, and presence or absence of position gap and collapse of the plated article as well as the shapes of the plated article were confirmed.

The results revealed that, in the test of Example 77 in which a template pattern was formed using the positive-type photosensitive resin composition of Example 1 to prepare a plated article, a plated article with a rectangular satisfactory cross-sectional shape could be formed, the plated article being satisfactorily adhered on the copper substrate without position gap. The results also revealed that, in the test of Comparative Example 19 in which a template pattern was formed using the positive-type photosensitive resin composition of Comparative Example 3 to prepare a plated article, position gap of the plated article occurs on the copper substrate, and the shape of the plated article is the shape in which the footing shape in the template pattern is traced. It is assumed that the position gap of the plated article in the test of Comparative Example 19 is caused by the generation of development residue on a copper substrate surface.

EXPLANATION OF REFERENCE NUMERALS

11 Substrate
12 Resist portion
13 Nonresist portion
14 Side wall
15 Inflexion point
16 Perpendicular line
17 Starting point of footing
18 Endpoint of footing

What is claimed is:

1. A chemically amplified positive-type photosensitive resin composition comprising:
an acid generator (A) which generates acid upon exposure to an irradiated active ray or radiation;
a resin (B) whose solubility in alkali increases under the action of acid; and
a mercapto compound (C) represented by the following formula (C1-1):

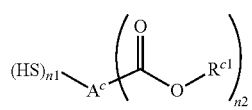

(C1-1)

wherein $R^{c1}$s each independently represent a hydrogen atom, a hydrocarbon group or an acid dissociable group, n1 is an integer of 1 or more and 4 or less, n2 is 1 or 2, at least one of $R^{c1}$ is a hydrogen atom or an acid dissociable group, and $A^c$ is an (n1+n2)-valent aliphatic cyclic group which optionally has one or more substituents and optionally includes one or more heteroatoms, or is represented by the following formula (C1-4):

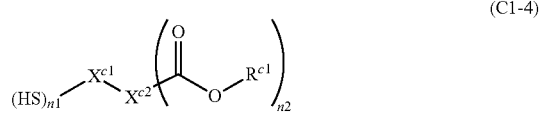

(C1-4)

wherein $R^{c1}$s each independently represent a hydrogen atom, a hydrocarbon group or an acid dissociable group, n1 is an integer of 1 or more and 4 or less, n2 is 1 or 2, at least one of $R^{c1}$ is a hydrogen atom or an acid dissociable group, $X^{c1}$ is an (n1+1)-valent nitrogen-containing heterocyclic group, and $X^{c2}$ is a single bond or an optionally substituted (n2+1)-valent hydrocarbon group.

2. The chemically amplified positive-type photosensitive resin composition according to claim 1, comprising, as the mercapto compound (C) a mercapto compound represented by the following formula (C1-1):

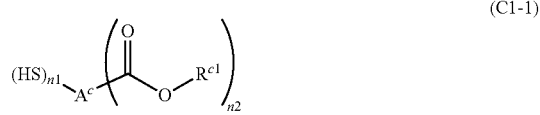

(C1-1)

wherein $R^{c1}$, n1 and n2 are the same as those in the formula (C1-1), and $A^c$ is an (n1+n2)-valent aliphatic cyclic group which optionally has one or more substituents and optionally includes one or more heteroatoms.

3. The chemically amplified positive-type photosensitive resin composition according to claim 1, wherein the mercapto compound (C) is represented by the following formula (C1-2):

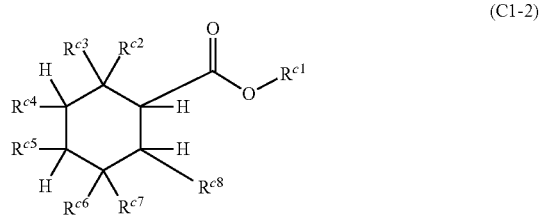

(C1-2)

wherein $R^{c1}$ is the same as that in the formula (C1-1), $R^{c2}$ and $R^{c6}$ are each independently a hydrogen atom or an alkyl group, or $R^{c2}$ and $R^{c6}$ may be bonded to each other to form a divalent group selected from the group consisting of —O—, —S—, —CH$_2$— and —C(CH$_3$)$_2$—, $R^{c3}$, $R^{c4}$, $R^{c5}$ and $R^{c7}$ are each independently a hydrogen atom or a mercapto group, $R^{c8}$ is a hydrogen atom or a group represented by —CO—O—$R^{c9}$, $R^{c9}$ is a hydrogen atom, a hydrocarbon group or an acid dissociable group, at least one of $R^{c1}$ and $R^{c9}$ is a hydrogen atom or an acid dissociable group, and at least one of $R^{c3}$, $R^{c4}$, $R^{c5}$ and $R^{c7}$ is a mercapto group.

4. The chemically amplified positive-type photosensitive resin composition according to claim 1, comprising, as the mercapto compound (C) is a compound represented by the following formula (C1-4):

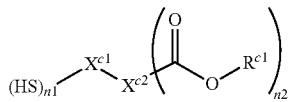
(C1-4)

wherein $R^{c1}$, n1 and n2 are the same as those in the formula (C1-1), $X^{c1}$ is an (n1+1)-valent nitrogen-containing heterocyclic group, and $X^{c2}$ is a single bond or an optionally substituted (n2+1)-valent hydrocarbon group.

5. The chemically amplified positive-type photosensitive resin composition according to claim 4, wherein $X^{c2}$ is an aromatic (n2+1)-valent hydrocarbon group substituted with one or more electron withdrawing groups.

6. The chemically amplified positive-type photosensitive resin composition according to claim 1, further comprising an alkali-soluble resin (D).

7. The chemically amplified positive-type photosensitive resin composition according to claim 6, wherein the alkali-soluble resin (D) comprises a resin selected from the group consisting of a novolak resin (D1), a polyhydroxystyrene resin (D2), and an acrylic resin (D3).

8. A photosensitive dry film comprising a substrate film, and a photosensitive resin layer formed on a surface of the substrate film, the photosensitive resin layer comprising the chemically amplified positive-type photosensitive resin composition according to claim 1.

9. A method of manufacturing a photosensitive dry film comprising applying the chemically amplified positive-type photosensitive resin composition according to claim 1 onto a substrate film to form a photosensitive resin layer.

10. A method of manufacturing a patterned resist film comprising:
   laminating a photosensitive resin layer on a substrate having a metal surface, the layer comprising the chemically amplified positive-type photosensitive resin composition according to claim 1;
   exposing the photosensitive resin layer through irradiation with an active ray or radiation in a position-selective manner; and
   developing the exposed photosensitive resin layer.

11. A method of manufacturing a substrate with a template comprising:
   laminating a photosensitive resin layer on a substrate having a metal surface, the layer comprising the chemically amplified positive-type photosensitive resin composition according to claim 1,
   exposing the photosensitive resin layer through irradiation with an active ray or radiation in a position-selective manner, and
   developing the exposed photosensitive resin layer to prepare a template for a plated article.

12. A method of manufacturing a plated article comprising plating the substrate with the template manufactured by the method according to claim 11 to form the plated article in the template.

13. A mercapto compound represented by the following formula (C1-1):

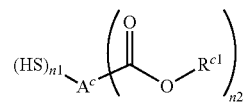
(C1-1)

wherein $A^c$ is an (n1+n2)-valent aliphatic cyclic group which optionally has one or more substituents and optionally includes one or more heteroatoms, $R^{c1}$ each independently represent a hydrogen atom, a hydrocarbon group or an acid dissociable group, n1 is an integer of 1 or more and 4 or less, n2 is 2, and at least one of $R^{c1}$s is a hydrogen atom or an acid dissociable group or represented by the following formula (C1-5):

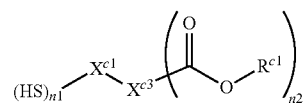
(C1-5)

wherein each $R^{c1}$ independently represent a hydrogen atom, a hydrocarbon group or an acid dissociable group, n1 is an integer of 1 or more and 4 or less, n2 is 1 or 2, at least one of $R^{c1}$s is a hydrogen atom or an acid dissociable group, $X^{c1}$ is an (n1+1)-valent nitrogen-containing heterocyclic group, and $X^{c3}$ is an aromatic (n2+1)-valent hydrocarbon group substituted with one or more electron withdrawing groups.

14. The mercapto compound according to claim 13, which is represented by the following formula (C1-3):

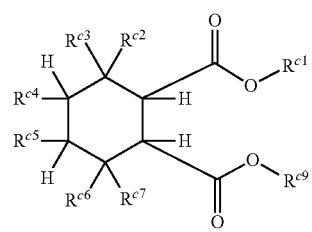
(C1-3)

wherein $R^{c1}$ is the same as that in the formula (C1-1), $R^{c2}$, and $R^{c6}$ are each independently a hydrogen atom or an alkyl group, or $R^{c2}$ and $R^{c6}$ may be bonded to each other to form a divalent group selected from the group consisting of —O—, —S—, —CH$_2$— and —C(CH$_3$)$_2$—, $R^{c3}$, $R^{c4}$, $R^{c5}$ and $R^{c7}$ are each independently a hydrogen atom or a mercapto group, $R^{c9}$ is a hydrogen atom, a hydrocarbon group or an acid dissociable group, at least one of $R^{c1}$ and $R^{c9}$ is a hydrogen atom or an acid dissociable group, and at least one of $R^{c3}$, $R^{c4}$, $R^{c5}$ and $R^{c7}$ is a mercapto group.

* * * * *